US010081798B2

(12) United States Patent
Wissing et al.

(10) Patent No.: US 10,081,798 B2
(45) Date of Patent: Sep. 25, 2018

(54) O-GLYCAN SIALYLATED RECOMBINANT GLYCOPROTEINS AND CELL LINES FOR PRODUCING THE SAME

(71) Applicant: Cevec Pharmaceuticals GmbH, Köln (DE)

(72) Inventors: Silke Wissing, Köln (DE); Jens Wölfel, Langenfeld (DE); Nicole Faust, Köln (DE)

(73) Assignee: Cevec Pharmaceuticals GmbH, Köln (DE)

(*) Notice: Subject to any disclaimer, the term of this patent is extended or adjusted under 35 U.S.C. 154(b) by 0 days.

(21) Appl. No.: 15/541,565

(22) PCT Filed: Dec. 15, 2015

(86) PCT No.: PCT/EP2015/002521

§ 371 (c)(1),
(2) Date: Jul. 5, 2017

(87) PCT Pub. No.: WO2016/110302

PCT Pub. Date: Jul. 14, 2016

(65) Prior Publication Data

US 2017/0342390 A1 Nov. 30, 2017

(30) Foreign Application Priority Data

Jan. 7, 2015 (EP) .................................... 15000016

(51) Int. Cl.
*C12N 9/10* (2006.01)
*C07K 14/81* (2006.01)
*C12P 21/00* (2006.01)
*C07K 14/475* (2006.01)

(52) U.S. Cl.
CPC ........ *C12N 9/1081* (2013.01); *C07K 14/4753* (2013.01); *C07K 14/8121* (2013.01); *C12P 21/005* (2013.01); *C12Y 204/99001* (2013.01); *C12Y 204/99004* (2013.01)

(58) Field of Classification Search
USPC .................. 435/188, 252.3, 320.1; 536/23.2
See application file for complete search history.

(56) References Cited

U.S. PATENT DOCUMENTS

2012/0322738 A1* 12/2012 Behrens ........... A61K 47/48215 514/14.1

FOREIGN PATENT DOCUMENTS

CN 101 613 678 A 12/2009
CN 101613678 A 12/2009
WO WO 2014140927 9/2014

OTHER PUBLICATIONS

Chica et al. Curr Opin Biotechnol. Aug. 2005;16(4):378-84.*
Singh et al. Curr Protein Pept Sci. 2017, 18, 1-11.*
Fukuta et al. Glycoconjugate Journal (2001), Dec. 2000, 17(12), 895-904.*
Schiedner et al. BMC Biotechnol. 2008; 8: 13. Published online Feb. 12, 2008.*
Antony et al. BMC Cancer. Dec. 2, 2014;14:901.*
Vallejo-Ruiz et al, Delineation of the minimal catalytic domain of human Galbetal-3GalNAc-alpha-2,3-sialyltransferase, 2001, Biochim Biophys Acta vol. 1549, pp. 161-173.
Dalziel et al., The relative activities of the C2GnT1 and ST3Gal-I glycosyltransferases determine the O-Glycan tumor . . . , 2000, J. Biol. Chem. vol. 276, pp. 11007-11015.
Whitehouse et al., A transfected sialyltransferase that is elevated in bresat cancer and localizes to the medial/trans-Golgi . . . , 1997, J. Cell Biol. vol. 137, pp. 1229-1241.
Shang et al, Molecular cloning and expression of Galb1,3GalNAc a2,3-sialyltransferase from human fetal liver, 1999, Eur. J. Biochem. vol. 265, pp. 580-588.
Blixt et al, Efficient chemoenzymatic synthesis of O-linked sialyl oligosaccharides, 2002, J. Am. Chem. Soc. vol. 124, pp. 5739-5746.
Priatel et al, The ST3Gal-1 Sialyltransferase controls CD8+ T-Lymphocyte homeostasis by modulating O-glycan biosynthesis, 2000, Immunity vol. 12, pp. 273-283.
Kono et al, Mouse beta-galactoside alpha-2,3-sialyltransferases: comparison of in vitro substrate . . . , 1997, Glycobiology, Oxford University Press, vol. 7, pp. 469-479.
Kojima et al, Kinetic properties and acceptor substrate preferences of two kinds of GalP1, 3GalNAc cu-2,3-sialyltransferase . . . , 1994, Biochemistry vol. 33, pp. 5772-5776.
Blixt et al., Efficient chemoenzymatic synthesis of O-linked sialyl oligosaccharides, 2002, J. Am. Chem. Soc. vol. 124, pp. 5739-5746.
Shang et al., Molecular cloning and expression of GalB1,3GalNAcalpha2,3 sialyltransferase from human fetal liver, 1999, Eur. J. Biochem. vol. 265, pp. 580-588.
Dolinski et al, Orthology and functional conservation in eukaryotes, 2007, Ann. Rev. Genet. vol. 41, pp. 465-507.
Gabaldon et al., Functional and evolutionary implications of gene orthology, 2013, Nature Reviews vol. 14, pp. 360-366.
Harduin-Lepers, Vertebrate sialyltransferases, Sialobiology: Structure, Biosynthesis and Function, Bentham Sci. Publ. 2013, pp. 139-187.
Kurosawa et al, Molecular cloning and expression of GalNAc alpha2,6-sialyltransferase, 1994, J. Biol. Chem. vol. 269, pp. 1402-1409.

(Continued)

*Primary Examiner* — Christian L Fronda
(74) *Attorney, Agent, or Firm* — HelixIP LLP

(57) ABSTRACT

The present invention relates to cell lines that are genetically modified to overexpress a β-galactoside α-2,3-sialyltransferase 1 (ST3Gal1), preferably human ST3Gal1, which can be used for the production of recombinant glycoproteins having highly or fully sialylated O-linked GalNAc glycans (GalNAc O-glycans), preferably core 1 GalNAc O-glycans, as well as to respective recombinant glycoproteins. Further, the present invention relates to respective methods of expressing recombinant glycoproteins, methods of increasing the degree of sialylation of recombinant glycoproteins, and methods of decreasing the micro-heterogeneity of GalNAc O-glycans. Finally, the present invention relates to respective uses of the above cell lines for the production of recombinant glycoproteins, for increasing the degree of sialylation of recombinant glycoproteins, and for decreasing the micro-heterogeneity of O-linked GalNAc glycans of recombinant glycoproteins.

8 Claims, 20 Drawing Sheets

Figure 1:
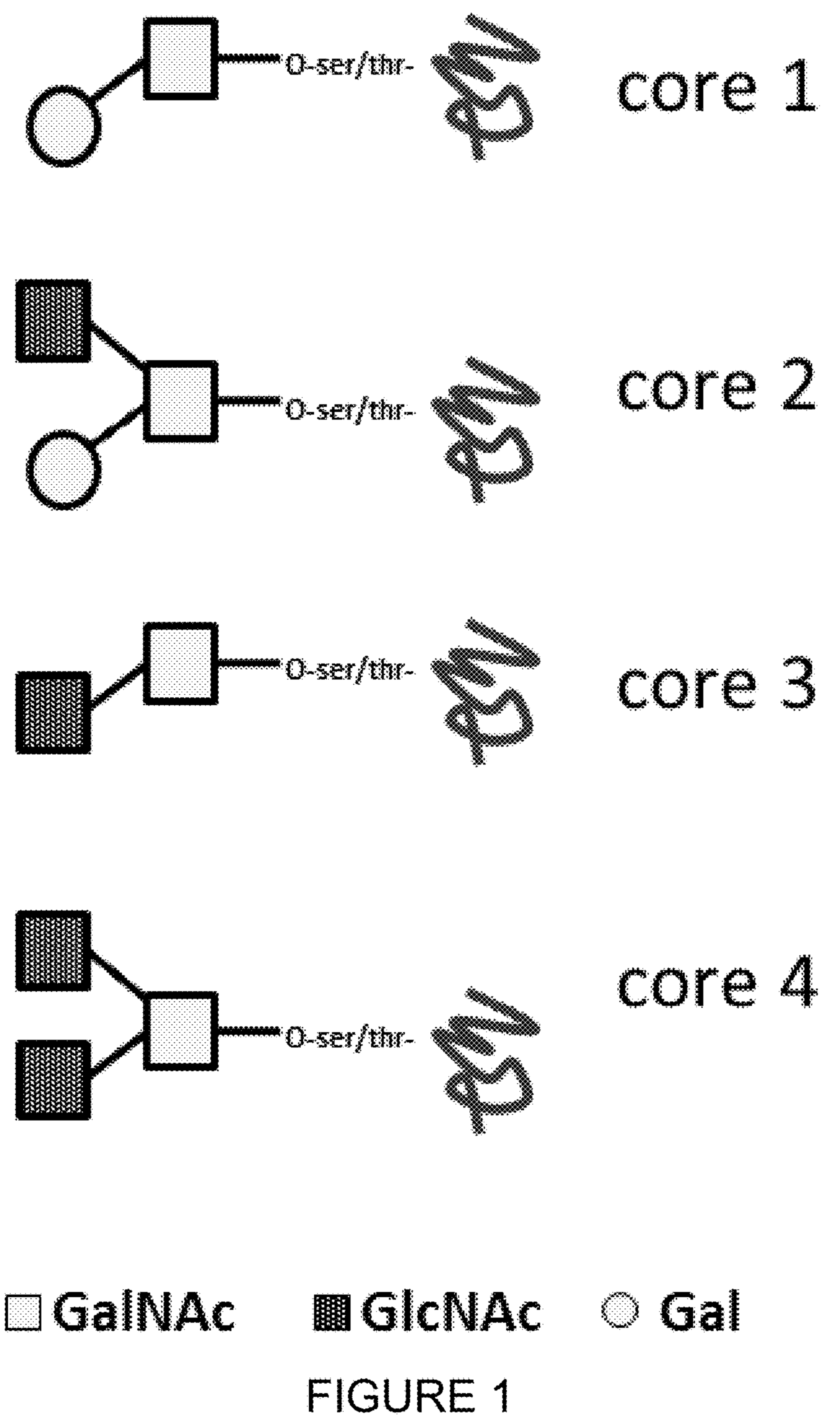

Specification includes a Sequence Listing.

(56) References Cited

OTHER PUBLICATIONS

Lee et al, Molecular cloning and expression of Galbeta1,3GalNAcalpha2,3-sialyltransferase from mouse brain, 1993, Eur. J. Biochem. vol. 216, pp. 377-385.

Backstrom et al., Recombinant MUC1 mucin with a breast cancer like O-glycosylation produced in large amounts in CHO cell, 2003, Biochem. J. vol. 376, pp. 677-686.

Fukuta et al., Genetic engineering of CHO cells producing human interferon-g by transfection of sialyltransferases, 2000, Glycoconjug. J. vol. 17, pp. 895-904.

Vallejo-Ruiz et al., Delineation of the minimal catalytic domain of human GalB1-3GalNAc a-2,3-sialyltransferase (hST3Gal1), 2001, Biochim Biophys Acta vol. 1549, pp. 161-173.

Blixt et al. Efficient chemoenzymatic synthesis of O-linked sialyl oligosaccharides, 2002, J. Am. Chem. Soc. vol. 124, pp. 5739-5746.

Fukuta et al. Genetic engineering of CHO cells producing human interferon-g by transfection of sialyltransferases, 2000, Glycoconjug J vol. 17, pp. 895-900.

* cited by examiner

O-GLYCAN SIALYLATED RECOMBINANT GLYCOPROTEINS AND CELL LINES FOR PRODUCING THE SAME

This application is a is a 371 of PCT/EP2015/002521, having an international filing date of Dec. 15, 2015, which claims the benefit of European Patent Application Ser. No. 15000016.4, filed Jan. 7, 2015, the content of which is incorporated by reference in its entirety.

The present invention relates to cell lines that are genetically modified to overexpress a β-galactoside α-2,3-sialyltransferase 1 (ST3Gal1), preferably human ST3Gal1, which can be used for the production of recombinant glycoproteins having highly or fully sialylated O-linked GalNAc glycans (GalNAc O-glycans), preferably core 1 GalNAc O-glycans, as well as to respective recombinant glycoproteins. Further, the present invention relates to respective methods of expressing recombinant glycoproteins, methods of increasing the degree of sialylation of recombinant glycoproteins, and methods of decreasing the micro-heterogeneity of GalNAc O-glycans. Finally, the present invention relates to respective uses of the above cell lines for the production of recombinant glycoproteins, for increasing the degree of sialylation of recombinant glycoproteins, and for decreasing the micro-heterogeneity of O-linked GalNAc glycans of recombinant glycoproteins.

Due to their clinical importance, the development of therapeutic proteins has accelerated immensely over the past years. However, the development of therapeutic proteins is often held up, in particular for complex glycosylated proteins, due to the difficulties in obtaining proteins with favorable glycosylation patterns. This often leads to suboptimal pharmacological properties such as e.g. reduced serum half-life or increased immunogenicity.

Another drawback is heterogeneity of the therapeutic proteins due to variations in the post-translational modification, in particular of the glycostructures. This can lead to inconsistencies in product quality between different production batches.

Therefore, in order to advance the development of therapeutic proteins, it is important to achieve homogenous post-translational modification.

Glycosylation is the most common post-translational modification. Nearly all biopharmaceuticals need to be correctly glycosylated in order to display the optimal therapeutic efficacy. In general, glycosylation refers to the covalent attachment of sugars to the protein surface, wherein the sugars are either connected to asparagine residues resulting in N-linked glycans (N-glycans) or serine or threonine residues resulting in O-linked glycans (O-glycans). The most common group of O-linked glycans are GalNAc O-glycans in which the serine or threonine is linked to N-acetyl-galactosamine (GalNAc) which in turn is linked to additional monosaccharides. As used herein, the terms "O-linked glycan" or "O-glycan" always relate to GalNAc O-glycans. As mentioned above, the glycosylation pattern can be very diverse from molecule to molecule as the attached forms can be different in monosaccharide order, branching pattern, and length (micro-heterogeneity). Additionally, not all glycosylation sites are fully occupied (macro-heterogeneity).

Glycosylation influences the solubility of proteins, their resistance to proteolysis, and their binding behavior to other proteins or to protein receptors such as e.g. the ASGPR (asialoglycoprotein receptor) and therefore influences the half-life of the glycoprotein in the plasma.

For small size proteins under about 50 kDa, clearance occurs mainly via renal clearance. Beside the size of a protein, also the protein surface charge has influence on the renal clearance, as the filtration of highly charged proteins in the kidney is decreased.

For large size proteins, clearance occurs mainly in the liver through specific and/or unspecific hepatic uptake. Examples for a specific uptake mediator would be the ASGPR, which binds specifically non-sialylated N-linked glycoproteins with a terminal galactose. Due to the action of this receptor, glycoproteins with terminal sialic acids covering the adjacent carbohydrate, galactose, have up to 100-fold increase in half-life as compared to their non-sialylated counterparts with terminal galactose residues on their N-linked glycans. Other receptors bind specifically to mannose, N-acetyl-glucosamine, or fucose and clear glycoproteins with these terminal sugars from the system.

From this perspective, a native N-glycosylation pattern including a high degree of terminal sialylation is crucial for therapeutic proteins since it determines the pharmacokinetic properties of the therapeutic protein. In addition, terminal sialic acids with the proper linkage on glycoproteins reduce the immunogenicity of the glycoproteins.

The foremost strategy to obtain nearly native glycostructures and a high degree of sialylation is to produce the recombinant proteins in cell lines capable of linking mammalian-like glycostructures to proteins, e.g. CHO cells (Chinese hamster ovary cells). However, CHO cells lack the enzyme needed to catalyze 2,6-linkage of sialic acids, and therefore they can only catalyze the 2,3-linkage. Moreover, in addition to N-acetylneuraminic acid (sialic acid; NeuAc), they also link N-glycolylneuraminic acid (NeuGc) to glycans, a sugar not synthesized in humans and therefore immunogenic when injected into humans. Therefore, a better strategy would be to generate therapeutic proteins from cell lines derived from human cells like CAP cells (derived from human amniocytes) or HEK293 cells (derived from human embryo kidney cells). However, sialylation of therapeutic proteins secreted from mammalian cell lines during fermentation is often incomplete.

Due to the importance of sialylation for the pharmacokinetic profile of a protein, a lot of efforts were undertaken to increase the degree of sialylation. The beneficial effect of complete sialylation of N-linked glycosylation is well understood, but relatively little is known about the effect of O-glycosylation. Therefore, so far all cell-engineering efforts directed at improving the sialylation take aim on N-linked glycostructures.

Figure 2:
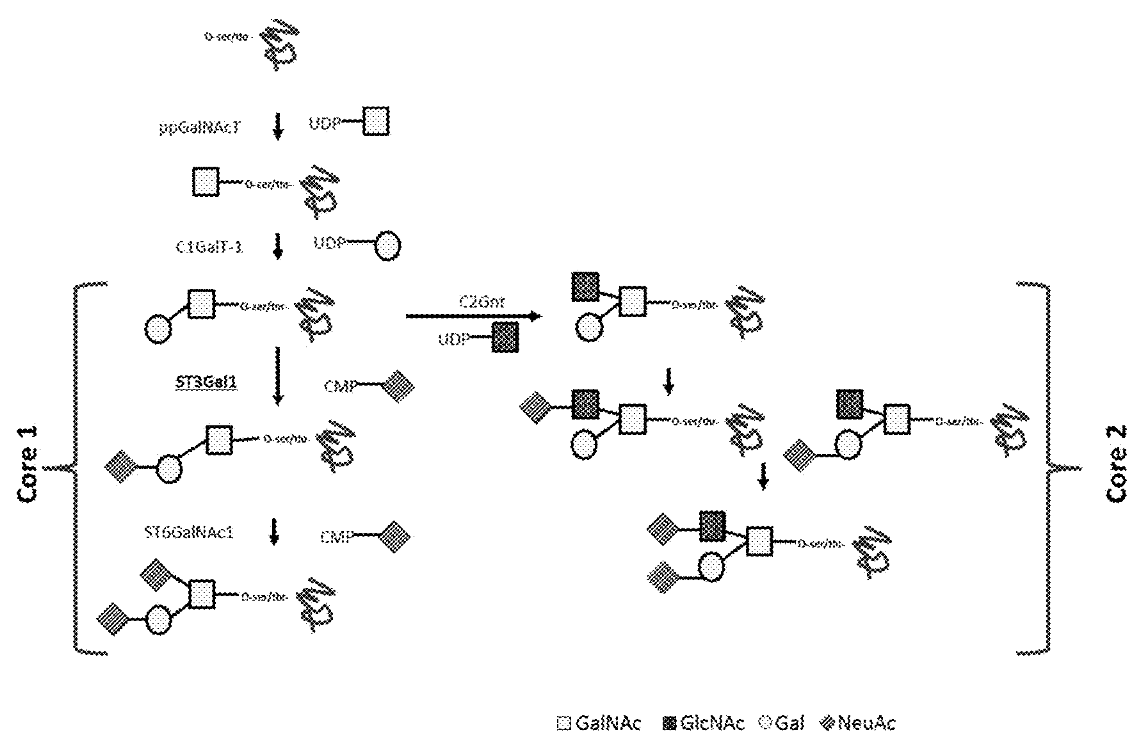

O-linked GalNAc glycans always have an α-linked N-acetylgalactosamine residue linked to serine or threonine. The GalNAc can be extended with residues like galactose, GlcNAc, fucose, or sialic acid. For O-linked GalNAc glycosylation, four principal core structures can be distinguished, core 1 (GalGalNAc), core 2 (GalGlcNAcGalNAc), core 3 (GlcNAcGalNAc), and core 4 (GlcNAc2GalNAc) (FIG. 1). The terminal ends are often further modified, e.g. with phosphates, sulfates, carboxylic acids, or sialic acids. O-linked GalNAc glycans play a role in maintaining structures of fully folded proteins, conferring protease stability. FIG. 2 shows the biosynthesis of core 1 and core 2 GalNAc O-glycans.

Although the dramatic positive impact of terminal sialic acids on N-linked glycans regarding increased half-life of therapeutic proteins is well established, the possible effect of terminal sialic acids at O-linked GalNAc glycans and the exact appearance of O-linked structures are not well understood.

Human insulin-like growth factor binding protein-6 (IGFBP6) has five O-linked glycosylation sites, and clearance from the blood is decreased for the O-glycosylated form in comparison to the deglycosylated one, indicating a general involvement of O-linked glycans while the role of sialic acids remains unclear. B cell-activating factor receptor 3 (BR3)-Fc has multiple O-linked glycosylation sites and sialylation levels vary in the manufacturing process. Separating the different forms, it could be shown that exposed galactose on the desialylated O-linked glycans of BR3-Fc was associated with rapid clearance due to uptake and degradation in the liver, in particular by non-parenchymal cell mediated clearance. Interestingly, the decrease in clearance rate that was associated with increased sialylated Gal was also observed with increased asialo GalNAc, indicating that the terminal asialo Gal might be the signal for the clearance. Adiponectin, an adipocyte-secreted, insulin-sensitizing hormone, has three putative O-linked glycosylation sites, which are not necessary for multimer formation but plasma clearance of the desialylated protein was accelerated compared with that of sialylated protein. So far, no methods have been described that will affect the sialylation or the structure of O-linked GalNAc glycans during recombinant expression of glycoproteins.

Accordingly, the technical problem underlying the present invention is to provide recombinant glycoproteins having highly or fully sialylated GalNAc O-glycans, as well as cell lines that are capable of recombinantly producing such proteins. Further, respective methods of expressing recombinant glycoproteins, increasing the degree of sialylation of recombinant glycoproteins, and decreasing the micro-heterogeneity of GalNAc O-linked glycans should be provided, as well as uses of the above cell lines for the production of recombinant glycoproteins, increasing the degree of sialylation of recombinant glycoproteins, and decreasing the micro-heterogeneity of GalNAc O-linked glycans.

The solution to the above technical problem is achieved by the embodiments characterized in the claims.

In particular, in a first aspect, the present invention relates to an animal cell line, preferably an insect, avian, or mammalian cell line, more preferably a mammalian, in particular human, cell line that is genetically modified to overexpress a β-galactoside α-2,3-sialyltransferase 1 (ST3Gal1).

The term "cell line genetically modified to overexpress a ST3Gal1" as used herein, also in the context of other transferases hereinafter, indicates that upon genetic modification, the individual cells of the cell line display a higher activity of the protein, e.g. the sialyltransferase, than they did before the genetic modification.

Genetic modifications that allow the overexpression of a given protein are not particularly limited and are known in the art. In a particular example, the cell line comprises an endogenous gene encoding a ST3Gal 1, such as e.g. human cell lines. In such cases, the cells can be genetically modified by inserting a promoter, enhancing element, and/or stabilizing element into the genome of the cells in a position suitable to cause overexpression of said nucleic acid. This can be done by homologous recombination using TALENS, Zn-finger proteins, CRISPR-CAS9, or other methods known in the art. Thus, in preferred embodiments, the cell line comprises an endogenous gene encoding ST3Gal1 and optionally endogenous genes encoding ST3Gal4 and/or ST6Gal1, and further has at least one genetic element, selected from the group consisting of a promoter, an enhancing element, and a stabilizing element inserted into the genome in one or more position(s) suitable to cause overexpression of ST3Gal1 and optionally ST3Gal4 and/or ST6Gal1. Suitable promoters, enhancing elements and stabilizing elements are not particularly limited and are known in the art. For example, promoters include constitutive promoters, e.g. a CMV, EF1alpha, SV40, RSV, UbC, CAG, BOS or PGK promoter, and inducible promoters, e.g. tetracycline inducible promoters or other inducible promoters known in the art. Further, enhancing elements (enhancers) include CMV enhancer, β-globin enhancer, immunoglobulin enhancer, and PGK-enhancer. Furthermore, stabilizing elements (chromatin elements) include matrix attachment regions (MARS), locus control regions (LCRs), and ubiquitously acting chromatin opening elements (UCOEs).

Alternatively, in cases where the cells do not comprise an endogenous gene encoding a ST3Gal1, or additionally, in cases where the cells do comprise an endogenous gene encoding a ST3Gal1, genetic modification of the cells can be achieved by introducing a nucleic acid, encoding a ST3Gal1 into the cells. Methods for introducing nucleic acids into cells are not particularly limited and are known in the art. For example, said nucleic acids could be introduced in circular or linearized form into the cells by electroporation, nucleofection, microinjection, via viral vectors, e.g. lentiviral vectors, reagent based methods, e.g. lipids, calcium phosphate, cationic polymers or other methods known in the art. The nucleic acids can be transiently or stably introduced into the cell by episomal systems or by stable integration of the nucleic acid into the genome. Said nucleic acids can be present in the cells in the form of one or more expression vector(s), e.g. pcDNA, pCEP, pLenti, pEntr, pDest, pEF, pEAK, pCMV, pStbl, or other expression vectors known in the art. Expression of the ST3Gal1 can be under the control of a constitutive promoter, e.g. a CMV, EF1alpha, SV40, RSV, UbC, CAG, BOS or PGK promoter, the endogenous promoter, or of an inducible promoter, e.g. tetracycline inducible promoter or other inducible promoters known in the art. Further, the nucleic acids encoding the ST3Gal1 can be present as one continuous nucleic acid, or can be present as separate nucleic acids, e.g. as separate expression vectors. Said nucleic acids can contain, in addition to the coding region and a promoter, suitable restriction sites, Kozak sequences, ribosomal binding sites, chromatin modulating elements, selection cassettes, episomal replication systems, e.g. Epstein-Barr Nuclear Antigen and ori P, or SV40 ori and SV40 T-large antigen, internal ribosomal entry sites (IRES), splicing signals, and polyadenylation signals known in the art. Thus, in preferred embodiments, the cell line comprises an exogenous nucleic acid encoding a β-galactoside α-2,3-sialyltransferase 1 (ST3Gal1), and optionally exogenous nucleic acids encoding a β-galactoside α-2,3-sialyltransferase 4 (ST3Gal4) and/or a β-galactoside α-2,6-sialyltransferase 1 (ST6Gal1).

Figure 14:
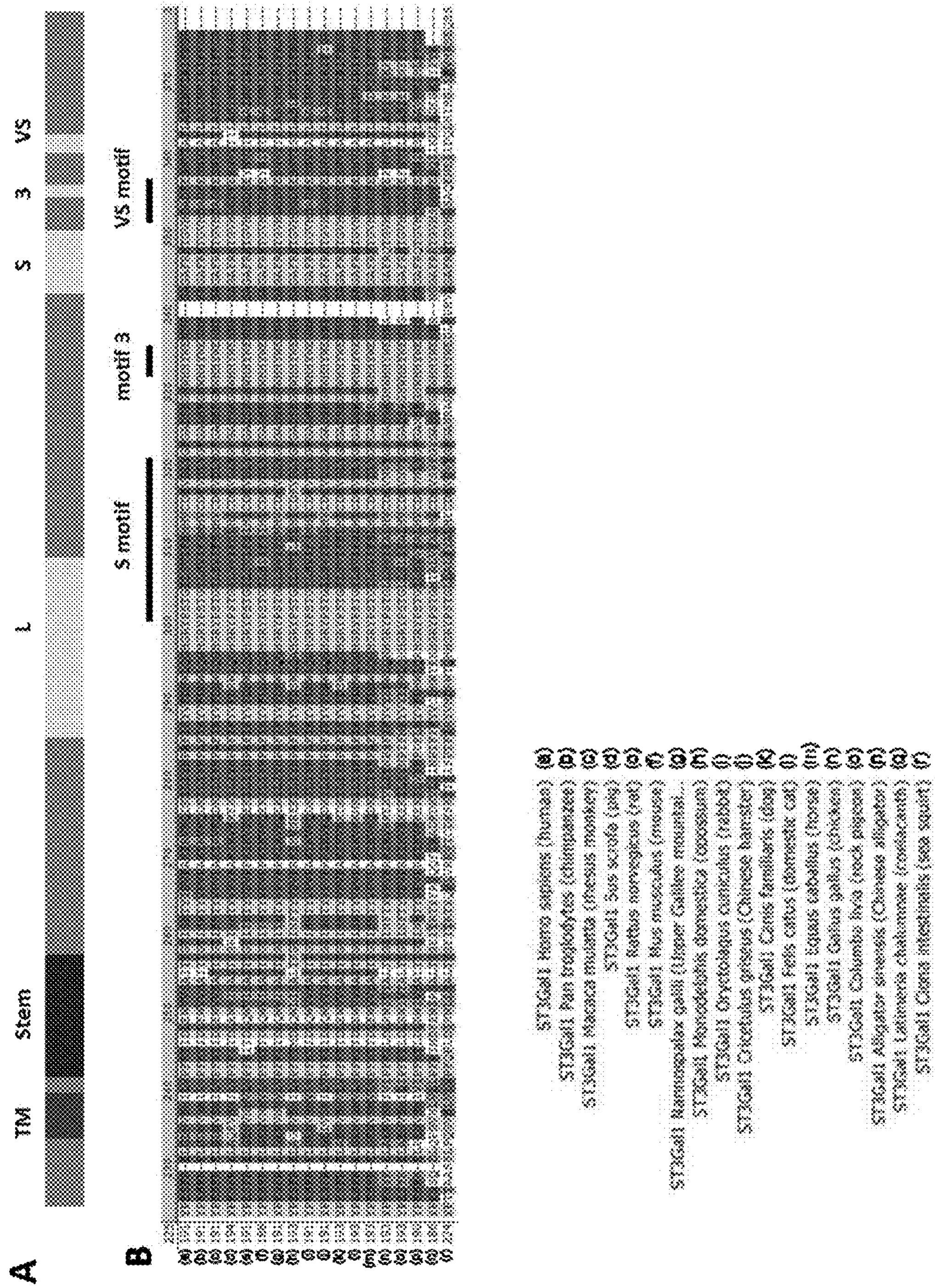

Suitable genes encoding a ST3Gal1 for transfection of cell lines are not particularly limited and include any genes from any origin that encode a protein having ST3Gal1 activity, i.e. a protein that catalyzes the linkage of sialic acid to a Gal-beta-1,3-GalNAc structure linked to Thr or Ser. Such genes can include, for example, ST3Gal1 genes encoding a ST3Gal1 protein comprising in its amino acid sequence, in particular in motif 3 of the C-terminal acceptor binding site, the conserved consensus sequence (H/C/R)(Y/H/F)(W/Y/F)(E/D/H/Y), wherein the sequence HYWE (SEQ ID NO: 5) is particularly preferred. FIG. 14 shows an alignment of the amino acids sequences of ST3Gal1 of various species, covering amino acids 191 to 340 of human ST3Gal1 comprising the catalytic domain, and displays said consensus sequence. The gene can also be selected from ST3Gal1 genes encoding a ST3Gal1 protein comprising an amino acid sequence which is at least 50%, preferably 75% and more preferably 90% % identical to amino acids 263 to 321 of the human ST3Gal1. Examples of ST3Gal1 genes include those derived from mammals and other organisms, such as those exemplified by SEQ ID NOs: 1 and 6-22.

In further preferred embodiments, the cell line is further genetically modified to overexpress a β-galactoside α-2,3-sialyltransferase 4 (ST3Gal4), preferably human ST3Gal4, and/or is further genetically modified to overexpress β-galactoside α-2,6-sialyltransferase 1 (ST6Gal1), preferably human ST6Gal1. Respective genetic modifications are preferably as defined above for ST3Gal1. Further, suitable genes encoding ST3Gal4 and suitable genes encoding ST6Gal1 are not particularly limited and include any genes from any origin that encode a protein having the respective activity. Again, mammalian, in particular human genes are particularly preferred.

The cell lines according to the present invention can be derived from cell lines, e.g. mammalian cell lines, known in the art. In preferred embodiments, a cell line of the present invention can be derived from Muscovy Duck cells (AGE.CR®) African green monkey kidney epithelial cells (Vero), Madin Darby canine kidney cells (MDCK), baby hamster kidney cells (BHK), Chinese hamster ovary (CHO) cells, human hepatocarcinoma cell lines (HepG2, Huh7), human embryonic kidney 293 (HEK293) cells, human neuronal precursor cells (AGE1.HN® and NC5T11), human embryonic retinoblasts (Per.C6), myeloma cell lines (HMCLs, MM.1, U266, RPMI8226), CML tumor cell lines (NM, NM-F9,), hybrid HEK293 and lymphoma cell (HKB11), or human amniocytes (CAP; cf. EP 1 230 354 B1), wherein CHO cells, HEK293 cells and CAP cells are preferred, and CAP cells are particularly preferred.

In this context, CAP cells are permanent amniocytic cell lines comprising a nucleic acid encoding the gene products of the adenovirus, in particular adenovirus type 5 (Ad5), E1A and E1B regions. CAP cells are derived from primary human amniocytes that are transformed with a nucleic acid encoding Ad5 E1A and E1B.

Accordingly, in a preferred embodiment, the cell lines according to the present invention can be derived from human primary amniocytes comprising at least one nucleic acid encoding the gene products of the adenoviral E1 and pIX region, preferably E1 and pIX region of adenovirus type 5 (Ad5) from nt. 505 to 4079, in which E1A is under the control of the murine phosphoglycerate kinase (pgk) promoter, while E1B and pIX expression is controlled from their natural promoters. The E1B downstream intron, splice acceptor and polyA signal are replaced by corresponding motifs from SV40.

Any or all of the above preferred and/or specific embodiments described for mammalian cell lines can be combined with each other in any manner.

In a further aspect, the present invention relates to a recombinant glycoprotein having GalNAc O-glycans that are sialylated to a degree of at least 80%.

As used herein, the term "recombinant glycoprotein" indicates that the respective glycoproteins are biotechnologically produced in genetically modified organisms or cells.

The glycoproteins according to the present invention have GalNac O-glycans that are sialylated to a degree of at least 80%, preferably at least 82%, more preferably at least 84%, at least 86%, at least 88%, at least 90%, at least 91%, at least 92%, at least 93%, at least 94%, at least 95%, at least 95.5%, at least 96%, at least 96.5%, at least 97%, at least 97.5%, at least 98%, at least 98.5%, or at least 99%. Preferably, the glycoproteins according to the present invention have GalNac O-glycans that are sialylated to a degree of 95% or above. In this context, the term "O-glycans that are sialylated to a degree of at least X %" as used herein indicates that X % of all terminal GalNac O-glycan monosaccharide moieties in a given glycoprotein preparation are sialic acid (N-acetylneuraminic acid; NeuAc).

In preferred embodiments, at least 80%, preferably at least 82%, more preferably at least 84%, at least 86%, at least 88%, at least 90%, at least 91%, at least 92%, at least 93%, at least 94%, at least 95%, at least 95.5%, at least 96%, at least 96.5%, at least 97%, at least 97.5%, or at least 98% GalNac O-glycans of the glycoproteins of the present invention are core 1 GalNAc O-glycan, i.e. GalNac O-glycans having a core structure of GP-Ser/Thr-O-GalNAc-Galwherein GP is the glycoprotein, Ser/Thr-O is a serine or threonine amino acid side chain of the glycoprotein, GalNAc is N-acetylgalactosamine, and Gal is galactose (FIG. 1).

Figure 11:
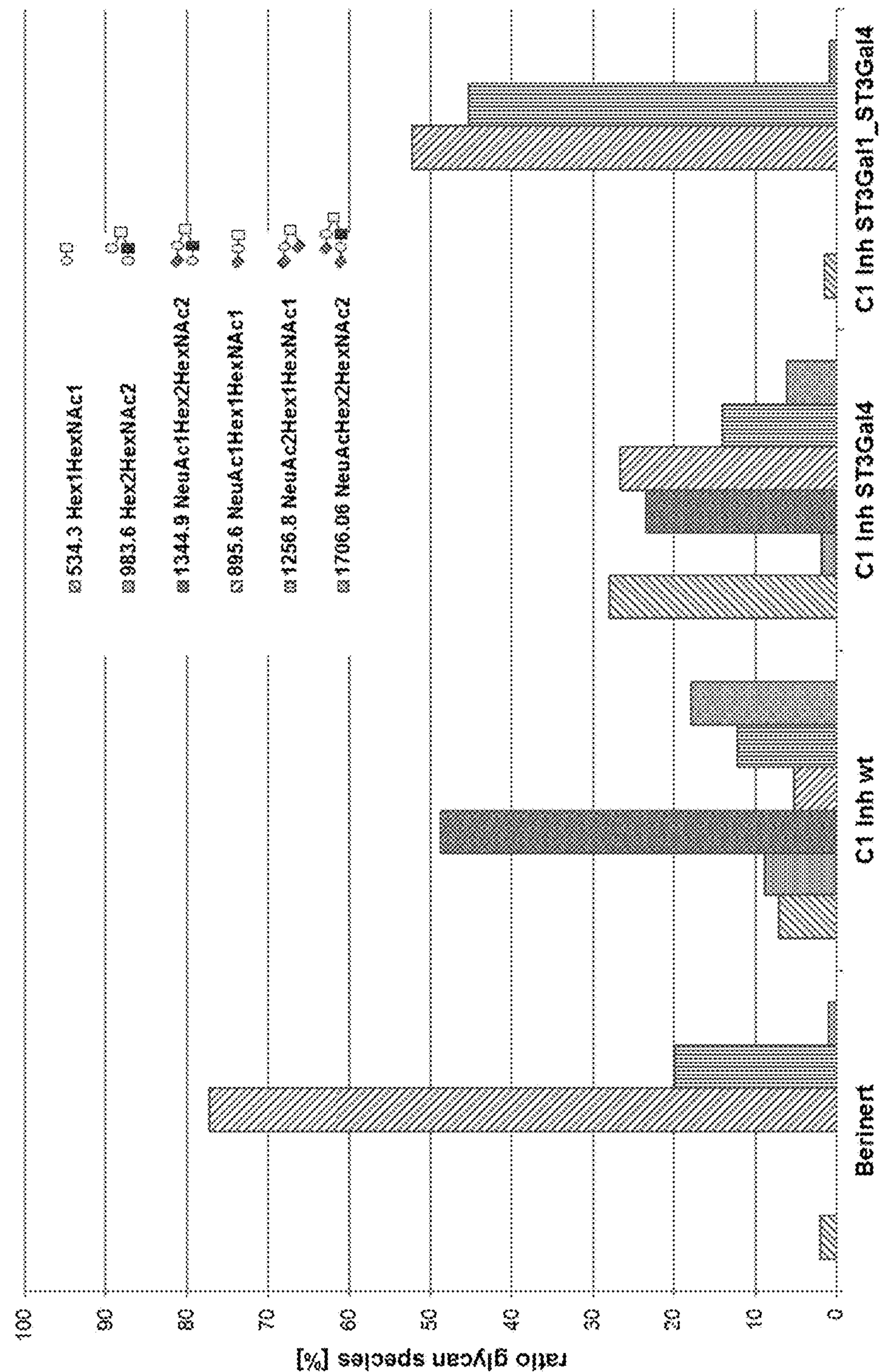

In preferred embodiments, the glycoproteins according to the present invention have core 1 GalNAc O-glycans that are disialylated to a degree of at least 25%, preferably at least 30%, more preferably at least 35%, at least 37.5%, at least 40%, at least 42.5%, or at least 45%. In this context, the term "core 1 GalNAc O-glycans that are disialylated to a degree of at least X %" as used herein indicates that X % of all core 1 GalNAc O-glycans have two terminal sialic acid moieties. In this context, FIG. 11 shows the relative amounts of the six main O-glycan species in various preparations of the glycoprotein C1 esterase inhibitor (C1 Inh).

Respective recombinant glycoproteins can be produced as described herein, e.g. by overexpression of a β-galactoside α-2,3-sialyltransferase 1 (ST3Gal1) together with the recombinant glycoprotein, and optionally by additional overexpression of a β-galactoside α-2,3-sialyltransferase 4 (ST3Gal4) and/or a β-galactoside α-2,6-sialyltransferase 1 (ST6Gal1). Preferably, said glycoproteins are produced in a cell line according to the present invention as described herein.

In a related embodiment, the GalNAc O-glycans of the recombinant glycoproteins of the present invention are characterized by a reduced micro-heterogeneity, i.e., a reduced diversity of GalNAc O-glycan structure and composition within a given glycoprotein preparation. Respective recombinant glycoproteins can be produced as described herein, e.g. by overexpression of ST3Gal1 together with the recombinant glycoprotein, and optionally by additional overexpression of ST3Gal4 and/or ST6Gal1. Preferably, said glycoproteins are produced in a cell line according to the present invention as described herein.

Specific glycoproteins according to the present invention are not particularly limited, provided that said glycoproteins have GalNAc O-glycans and fulfill the respective requirements of GalNAc O-glycan sialylation. Preferably, said glycoproteins are mammalian, more preferably human glycoproteins. Glycoproteins can be selected from the group consisting of growth factors, peptide hormones, cytokines, enzymes, antibodies, antibody fragments, blood clotting factors, and protease inhibitors. Preferably, the glycoprotein is selected from the group consisting of hepatocyte growth factor (HGF), erythropoietin (EPO), Factor VIII (FVIII), Factor IX (FIX), von-Willebrand-Factor (vWF), and C1 esterase inhibitor (C1-inhibitor; C1 Inh), wherein C1 Inh is particularly preferred.

Thus, in a particularly preferred embodiment, the present invention relates to a recombinant C1 esterase inhibitor (C1-inhibitor; C1 Inh), preferably recombinant human C1 Inh, having GalNAc O-glycans that are sialylated to a degree of at least 80%. All of the above preferred and/or specific embodiments described for recombinant glycoproteins in general also apply to this specific embodiment of recombinant (human) C1 Inh.

Any or all of the above preferred and/or specific embodiments described for recombinant glycoproteins can be combined with each other in any manner.

In further aspects, the present invention relates to a method for the expression of recombinant glycoproteins having GalNAc O-glycans that are sialylated to a degree of at least 80%, to a method for increasing the degree of sialylation of GalNAc O-glycans of recombinant glycoproteins, and to a method for decreasing the micro-heterogeneity of GalNAc O-glycans of recombinant glycoproteins, all of said methods comprising the step of overexpressing with the recombinant glycoproteins a β-galactoside α-2,3-sialyltransferase 1 (ST3Gal1).

In particular embodiments, said methods comprise the steps of:

(a) providing a cell line according to the present invention;
(b) expressing the glycoprotein of interest in said cell line; and
(c) overexpressing a ST3Gal1 and optionally one or more, selected from the group consisting of ST3Gal4, and ST6Gal1, together with the glycoprotein of interest.

Further, the methods of the present invention can comprise the step of (d) isolating the glycoprotein of interest.

In these aspects, all of the definitions and preferred and/or specific embodiments described for the recombinant glycoproteins of the present invention and the cell lines of the present invention apply in an analogous manner where applicable.

In particular, the recombinant glycoproteins produced in said methods, or the recombinant glycoproteins whose degree of sialylation is increased in said methods, or the recombinant glycoproteins whose GalNAc O-glycan micro-heterogeneity is decreased in said methods, can be any glycoproteins of the present invention as defined above. Further, the cell lines provided in step (a) of the methods of the present invention can be any cell line of the present invention as defined above.

Means for the expression of proteins in the cell lines of the present invention are not particularly limited and are known in the art. In this context, the step (b) of expressing the glycoprotein of interest in said cell line encompasses the transfection of a respective coding nucleic acid into said cell line prior to the actual expression of the glycoprotein. Further, means for isolating a glycoprotein of interest from a cell culture are not particularly limited and are known in the art.

In related aspects, the present invention relates to a use of a cell line according to the present invention for the production of recombinant glycoproteins having GalNAc O-glycans that are sialylated to a degree of at least 80%, and/or for increasing the degree of sialylation of recombinant glycoproteins and/or for decreasing the micro-heterogeneity of GalNAc O-glycans of recombinant glycoproteins.

In these aspects, all of the definitions and preferred and/or specific embodiments described for the recombinant glycoproteins of the present invention and the cell lines of the present application apply in an analogous manner where applicable.

In particular, the recombinant glycoproteins produced in said use, or the recombinant glycoproteins whose degree of sialylation is increased in said use, or the recombinant glycoproteins whose GalNAc O-glycan micro-heterogeneity is decreased in said use, can be any glycoproteins of the present invention as defined above. Further, the used cell lines of the present invention can be any cell lines of the present invention as defined above.

The figures show:

FIG. 1:

Four Major Core GalNAc O-Linked Glycosylation Structures can be Distinguished.

GalNAc O-linked glycan contains an α-linked N-acetylgalactosamine residue linked to serine or threonine. The GalNAc can be extended with residues like galactose, GlcNAc, fucose, or sialic acid. Four principal core structures can be distinguished, core 1 (GalGalNAc), core 2 (GalGlcNAcGalNAc), core 3 (GlcNAcGalNAc), and core 4 (GlcNAc2GalNAc). These core structures can further be extended and branched.

FIG. 2:

Biosynthesis of Core 1 and Core 2 GalNAc O-Glycans.

First step in the biosynthesis is the linkage of a GalNAc to a specific serine or threonine residue in the protein backbone, resulting in so called Tn-antigen. The enzyme C1GalT-1 catalyzes then the linkage of a galactose to the GalNAc, forming therefore the basis for the core 1 structure also called T-antigen. Core 1 serves as a substrate for either the C2Gnt, which catalyzes the synthesis of GlcNAc β1-6 linked branches, resulting in core 2 structures. Core 1 structures can also additionally be sialylated by the ST3Gal1 resulting in mono-sialylated Gal1-3(NeuAc2-6)GalNAc or di-sialylated NeuAc2-3Gal1-3(NeuAc2-6)GalNAc.

FIG. 3:

Serum Concentration of C1 Inh after a Single Intravenous Injection of Recombinant C1 Inh (CAP C1 Inh, CAP C1 Inh ST3Gal4, CAP C1 Inh ST3Gal1/ST3GAL4 Pool A and Pool B) or Berinert in Rats.

Pharmacokinetic studies were performed in rats injected with either Berinert (C1 Inh derived from human plasma) or recombinant C1 Inh, expressed in CAP C1 Inh, CAP C1 Inh ST3Gal4, or CAP C1 Inh ST3Gal1ST3GAL4. Residual hC1 Inh amounts after i.v. bolus injection of a 10 mg/kg dose in Sprague Dawley female rats were determined at different time points: 5 min, 10 min, 15 min, 20 min, 30 min, 60 min, 2 h, 4 h, 6 h, and 24 h. The percentage of the residual C1 Inh was detected via ELISA. For each animal, C1 Inh concentration was normalized to the concentration at 5 min=100%. Values were fitted and plotted versus time post injection. From each group (n=4, except Berinert n=7) a graph for one representative animal is shown.

FIG. 4:

Serum Half-Life of C1 Inh after a Single Intravenous Infection of Recombinant C1 Inh (CAP C1 Inh, CAP C1 Inh ST3Gal4, CAP C1 Inh ST3Gal1/ST3GAL4 Pool A and Pool B) or Berinert in Rats.

Pharmacokinetic studies were performed in rats injected with either Berinert (C1 Inh derived from human plasma) or recombinant C1 Inh, expressed in CAP C1 Inh, CAP C1 Inh ST3Gal4, or CAP C1 Inh ST3Gal1/ST3GAL4. Residual hC1 Inh amounts after i.v. bolus injection of a 10 mg/kg dose in Sprague Dawley female rats were determined at different time points: 5 min, 10 min, 15 min, 20 min, 30 min, 60 min, 2 h, 4 h, 6 h, and 24 h. The percentage of the residual C1 Inh was detected via ELISA. For each animal, C1 Inh concentration was normalized to the concentration at 5 min=100%.

Values were fitted and plotted versus time post injection. Shown are the mean values for t1/2 (n=4, Berinert n=7), error bars=±SD.

FIG. 5:

Determined AUC Values for the Varying Recombinant C1 Inh (CAP C1 Inh, CAP C1 Inh ST3Gal4, CAP C1 Inh ST3Gal1/ST3GAL4 Pool A and Pool B) or Berinert.

Comparison of bioavailability between the different recombinant glyco-optimized C1 Inh samples. Shown are the mean values for AUC (n=4, Berinert n=7), error bars=±SD.

FIG. 6:

N-Linked Glycosylation Analysis of C1 Inh Expressed from CAP Cell Lines with and Without Coupled Expression of ST3Gal1 and/or ST3Gal4 and Add-on Western Blot Analysis.

Purified recombinant C1 Inh expressed in CAP cells migrates slower in SDS PAGE compared to Berinert. Expression of ST3Gal1 and ST3Gal4 causes a shift of the recombinant C1 Inh towards Berinert after removal of N-glycosylation by PNGase, indicating a mass reduction of the remaining O-linked-glycans. 100 ng purified recombinant C1 Inh expressed in glyco-improved C1-expressing cell lines were digested with 500 U PNGaseF (NEB) for 1 h at 37° C., followed by a separation on a 4-12% Bis-Tris gel. (Molecular weight marker: MagicMark™ XP Western Protein Standard).

FIG. 7:

ECL Lectin Immunoblot of Recombinant C1 Inh Expressed in CAP Cells in the Presents or Absence of Sialyltransferases.

*Erythrina crista galli* (ECL) lectin detects β1-4 linked terminal galactose on N-linked glycans. Therefore, a diminished signal in the ECL blot means an increased amount of sialylation. N-linked glycans of Berinert are almost completely sialylated, C1 Inh from CAP cells overexpressing ST3Gal4 are also nearly completely sialylated. C1 Inh from CAP cells overexpressing ST3Gal1/4 display a slightly higher amount of asialo N-glycans. In comparison, unmodified C1 Inh purified from CAP cells without overexpression of sialyltransferase provide a strong signal in the ECL blot indicating a certain amount of asialo N-glycans. As loading control same samples were treated with neuraminidase to remove the entire sialic acids content from the glycan structures. (Molecular weight marker: MagicMark™ XP Western Protein Standard).

FIG. 8:

PNA Lectin Immunoblot of Recombinant C1 Inh Expressed in CAP Cells in the Presents or Absence of Sialyltransferases.

The amount of sialylation of O-linked glycans of recombinant C1 Inh in CAP cells upon overexpression of ST3Gal1 was tested by PNA lectin immunoblots. Peanut agglutinin (PNA) detects β1-3 linked terminal galactose on O-linked glycans. Therefore, a decreased signal in the PNA lectin blot implies an increased level of sialylation of the galactose residues of O-glycans. C1 Inh purified from cell culture supernatants of CAP cells overexpressing ST3Gal1 displays no signal indicating complete sialylation of the O-glycans. The same is true for plasma derived C1 Inh, Berinert. (Molecular weight marker: MagicMark™ XP Western Protein Standard).

FIG. 9:

Comparison of rhC1 Inh Isoform Patterns by IEF Analysis.

As the backbones of the different C1 Inh are identical, changes in the IEF are most likely due to changes in the sialic acid content. C1 Inh expressed in CAP with additional expression of ST3Gal4 results in a modified C1 Inh which shifts, in comparison to the unmodified C1 Inh, only slightly towards the anode, indicating a small increase in the total amount of sialic acids per molecule. In contrast, the additional expression of ST3Gal1 results in a pronounced C1 Inh shift towards the anode, indicating a significant increase in the total amount of sialic acids per molecule.

FIG. 10:

MALDI-TOF Mass Spectrum Analysis of CAP C1 Inh O-Glycans of Protein Expressed With or Without Additional Overexpression of ST3Gal1 and/or ST3GAL4 in Comparison to Berinert.

(A) The analysis of the CAP C1 Inh sample reveals a high abundance of monosialylated O-glycans with a core 2 structure and a terminal galactose. (B) Expression of C1 Inh combined with overexpression of ST3Gal4 also results in large quantities of monosialylated O-glycans with a core 2 structure and a terminal galactose. (C) Expression of C1 Inh combined with overexpression of ST3Gal4 and ST3Gal1 leads to a shift towards core 1 O-glycan structures, which are mono- or di-sialylated, but without any terminal galactose residues. Core 2 structures are barely detectable. (D) O-glyco analysis of Berinert shows the present of only core 1 O-glycans which are mostly mono-sialylated without terminal galactose residues.

FIG. 11:

Summary of the MALDI-TOF Mass Spectrum Results of C1 Inh Expressed in CAP Cells Coupled with or Without Overexpression of ST3Gal1 and/or ST3GAL4 Compared to Berinert.

Displayed are the amounts of the six main glycan species in relation to the total sum of the same glycans. Glycan fragments generated by MALDI-TOF or negligible signal were not used for this analysis. In the CAP C1 Inh samples without additional overexpression of ST3Gal1 or ST3Gal4, namely CAP C1 Inh, predominantly O-glycans with a core 2 structure are detectable (Gal1-3(Gal1-GlcNAc1-6)GalNAc-ol_Core 2) (m/z 983), or NeuAc2-3Gal1-3(Gal1-4GlcNAc1-6)GalNAc-ol (m/z 1344), Gal1-3(NeuAc2-3Gal1-4GlcNAc1-6)GalNAc-ol (m/z 1344) and NeuAc2-3Gal1-3(NeuAc2-3Gal1-4GlcNAc1-6)GalNAc-ol (m/z 1706)). Core 1 structures are only rarely detectable. Additional expression of ST3Gal4 leads to a slight shift towards core 1 structures (NeuAc2-3Gal1-3GalNAc-ol_Core 1). Interestingly, the expression of C1 Inh in CAP cells coupled with the overexpression of ST3Gal1 leads to the exclusive expression of NeuAc2-3Gal1-3GalNAc-ol (Core 1) respectively Gal1-3(NeuAc2-6)GalNAc-ol (m/z 895) and NeuAc2-3Gal1-3(NeuAc2-6)GalNAc-ol (m/z 1256). “Hex” in this figure designates hexose.

FIG. 12:

The Different Core 1 and Core 2 GalNAc O-Glycan Structures.

The MALDI-TOF-mass spectrum analysis revealed that the different samples group in two different clusters of either core 1 or core 2 O-glycan structures.

FIG. 13:

ECL and PNA Lectin Immunoblots of Recombinant HGF Expressed in CAP Cells in the Presence or Absence of Sialyltransferases.

(A) *Erythrina crista galli* (ECL) lectin detects β1-4 linked terminal galactose on N-linked glycans. Therefore, a diminished signal in the ECL blot means an increased amount of sialylation. Overexpression of ST3Gal4 or ST3Gal1/4 results in an increased sialylation of the N-linked glycans, whereas overexpression of ST3Gal1 has no effect compared to unmodified C1 Inh. (B) The amount of sialylation of recombinant HGF in CAP cells upon overexpression of ST3Gal1 was tested by PNA lectin immunoblots. Peanut agglutinin (PNA) detects β1-3 linked terminal galactose on O-linked glycans. Therefore, a decreased signal in the PNA lectin blot implies an increased level of sialylation of the galactose residues of O-glycans. Cell culture supernatant from CAP cells overexpressing ST3Gal1 results in a significant decrease of the signal indicating increased sialylation of the O-glycan. (Molecular weight marker: MagicMark™ XP Western Protein Standard).

FIG. 14:

Domain Structure and Sequence Alignment of ST3Gal1.

A) Domain structure of ST3Gal1 Sialyltransferases. TM, transmembrane domain; Stem, stem region; L, sialyl motif L (long); sialyl motif S (short); 3, sialyl motif III; VS, sialyl motif VS (very short). The L motif is involved in binding of CMP-Sia, the motif S is involved in binding of CMP-Sia as well as acceptor, motif 3 and VS contain the catalytic consensus sequence and is involved in binding the acceptor. B) Alignment of ST3Gal1 C-terminal sequences from humans, mammals, birds, reptiles, fish, and ascidians. Amino acid residues identical in all species are shaded in light grey, amino acids identical in most species in dark gray and blocks of similar amino acids in medium gray. The consensus sequence for the catalytically active amino acids in motif 3 reads (H/C/R)(Y/H/F)(W/Y/F)(E/D/H/Y) (preferred amino acids in corresponding position in bold).

FIG. 15:

ECL and PNA Lectin Immunoblots of Recombinant C1 Inh Expressed in 293F Cells in the Presence or Absence of Sialyltransferases.

(A) *Erythrina crista galli* (ECL) lectin detects β1-4 linked terminal galactose on N-linked glycans. Overexpression of ST3Gal4 or ST3Gal1/4 results in an increased sialylation of the N-linked glycans, whereas overexpression of ST3Gal1 alone has no effect compared to unmodified C1 Inh. Neuraminidase catalyzes the hydrolysis of N-acetylneuraminic acid residues from oligosaccharide, thus neuraminidase treated samples serve as positive control. (B) The amount of sialylation of recombinant C1 Inh in 293F cells upon overexpression of ST3Gal1 was tested by PNA lectin immunoblots. Cell culture supernatant from 293F cells overexpressing ST3Gal1 results in a significant decrease of the signal indicating increased sialylation of the O-glycan. Neuraminidase treated samples serve as positive control. (Molecular weight marker: MagicMark™ XP Western Protein Standard).

FIG. 16:

PNA Lectin Immunoblots of Recombinant C1 Inh Expressed in CHO-K1 Cells in the Presence or Absence of Sialyltransferases.

The amount of sialylation of recombinant C1 Inh in CHO-K1 cells upon overexpression of ST3Gal1 was tested by PNA lectin immunoblots. Cell culture supernatant from CHO-K1 cells overexpressing ST3Gal1 show a significant decrease of the signal indicating increased sialylation of the O-glycan compared to C1 Inh purified from CHO-K1 C1 Inh control cells. Western Blot analysis of the same protein samples served as loading control. (Molecular weight marker: MagicMark™ XP Western Protein Standard).

FIG. 17:

ECL and PNA Lectin Immunoblots of Recombinant C1 Inh Expressed in MDCK.1 Cells in the Presence or Absence of Sialyltransferases.

(A) *Erythrina crista galli* (ECL) lectin detects β1-4 linked terminal galactose on N-linked glycans. Overexpression of ST3Gal1 in MDCK.1 cells has no effect on the amount of sialylation of the N-linked glycans. (B) The amount of sialylation of recombinant C1 Inh upon overexpression of ST3Gal1 in MDCK.1 cells was tested by PNA lectin immunoblots. Cell culture supernatant from MDCK.1 cells overexpressing ST3Gal1 show a significant decrease of the signal indicating increased sialylation of the O-glycan. (Molecular weight marker: MagicMark™ XP Western Protein Standard).

The present invention will be further illustrated in the following examples without being limited thereto.

EXAMPLES

Experimental Procedures:

Cell Culture and Fermentation

The permanent human amniocyte cell line CAP 1D5 was cultured in suspension, either in chemically defined, animal component free CAP-CDM medium (CEVEC Pharmaceuticals, Germany) supplemented with 6 mM stable glutamine (biochrom, Germany), or in serum free PEM media (Life Technologies) supplemented with 4 mM stable glutamine (biochrom, Germany).

The 293F cells from Life Technologies were cultured in suspension in Freestyle 293 expression media (Life Technologies), supplemented with 4 mM stable glutamine (biochrom, Germany).

The adherent CHO-K1 cells (ATCC, CCL-61) were cultured in F12-K media (Life Technologies), supplemented with 10% FBS, and 2 mM stable glutamine (biochrom, Germany).

The adherent MDCK.1 cells (ATCC, CRL-2935) were cultured either in EMEM media (ATCC) or in DMEM F-12 (ATCC) supplemented with 10% FBS and with 2 mM stable glutamine (biochrom, Germany).

CAP cells and 293F cells were cultivated at 37° C. in shaker flasks (Corning, 125 mL (25 mL wv) or 3000 mL (1000 mL wv)) at 5% $CO_2$, and 185 rpm. During fermentation CAP cells were fed at d3, d5, and d7 with 10% CAP-CDM feed solution (CEVEC Pharmaceuticals, Germany) and 4 mM stable glutamine (biochrom, Germany). Adherent CHO-K1 and MDCK.1 cells were cultured at 37° C., 5% $CO_2$, in 6 cm or 10 cm cell culture dishes (TPP) or 225 $cm^2$ cell culture dishes (BD).

Cloning

For the generation of the cell lines used in the present invention, cells were sequentially nucleofected with the nucleic acid constructs encoding the glycostructure modifying enzymes ST3Gal1 and/or ST3Gal4, as well as the specific recombinant protein. Only stable cell lines were utilized. Table 1 lists all cell lines created.

TABLE 1

Stable cell lines used in the present invention.

| Cell line | rec. protein | overexpression of the sialyltransferase(s) |
|---|---|---|
| CAP-C1 Inh | C1 Inh | / |
| CAP-C1 Inh-ST3Gal1 | C1 Inh | ST3Gal1 |
| CAP-C1 Inh-ST3Gal4 | C1 Inh | ST3Gal4 |
| CAP-C1 Inh-ST3Gal1/4 | C1 Inh | ST3Gal1/ST3Gal4 |
| CAP-HGF | HGF | / |
| CAP-HGF-ST3Gal1 | HGF | ST3Gal1 |
| CAP-HGF-ST3Gal4 | HGF | ST3Gal4 |
| CAP-HGF-ST3Gal1/4 | HGF | ST3Gal1/ST3Gal4 |
| 293F-C1 Inh | C1 Inh | / |
| 293F-C1 Inh-ST3Gal1 | C1 Inh | ST3Gal1 |

TABLE 1-continued

| Stable cell lines used in the present invention. | | |
|---|---|---|
| Cell line | rec. protein | overexpression of the sialyltransferase(s) |
| 293F-C1 Inh-ST3Gal1/4 | C1 Inh | ST3Gal1/ST3Gal4 |
| CHO-C1 Inh | C1 Inh | / |
| CHO-C1 Inh-ST3Gal1 | C1 Inh | ST3Gal1 |
| MDCK.1-C1 Inh | C1 Inh | / |
| MDCK.1-C1 Inh-ST3Gal1 | C1 Inh | ST3Gal1 |

For designing the ST3Gal1 cDNA, sequence information of the precursor protein and mature protein was based of the database entry UniProt Q11201 (SEQ ID NO: 1). For cloning, a ClaI restriction site and a Kozak sequence were added 5' of the start codon of the human ST3Gal1 cDNA and an EcoRV restriction site was added 3' of the stop codon to be inserted between the ClaI and EcoRV restriction sites in the pStbl-Puro-CMV-MCS(—) vector resulting in the expression plasmid pStbl-Puro-CMV-ST3Gal1. This vector contains a CMV promoter driving the expression of the gene of interest, followed by an SV40 intron for improved, splicing-mediated mRNA transport and a multiple cloning site for the insertion of the gene of interest. The selection marker (Puromycin) is driven by the human ubiquitin (UbC) promoter. cDNA synthesis was performed at GeneArt (Germany, Life Technologies).

For designing the ST3Gal4 cDNA, sequence information of the precursor protein and mature protein was based of the database entry UniProt Q11206 (SEQ ID NO: 2). For cloning, a ClaI restriction site and a Kozak sequence were added 5' of the start codon of the human ST3Gal4 cDNA and a EcoRV restriction site was added 3' of the stop codon to be inserted between the ClaI and EcoRV restriction sites in the pStbl-Puro-CMV-MCS(—) vector resulting in the expression plasmid pStbl-Puro-CMV-ST3Gal4. cDNA synthesis was performed at GeneArt (Germany, Life Technologies).

Nucleofection and Pool Generation

Nucleofection was performed using a Nucleofector (LONZA) with the appropriate Nucleofector Kit (KitV; CAP cells, 293F, and CHO or the KitT; MDCK.1 cells) according to the manufacturer's protocol. Briefly, during exponential growth phase of the culture $1\times10^7$ cells were harvested via centrifugation (150 g for 5 min) and resuspended in 100 μl complete nucleofector solution and mixed with a total of 5 μg plasmid. Nucleofection was performed using the X001 program (CAP and 293F cells), the U024 program (CHO-K1), or the P029 program (MDCK.1). After the pulse, cells were recovered in complete cell culture media. The cells were cultured as before. 72 to 96 h post-nucleofection cells were selected with 5 pg/ml blasticidin (therapeutic protein) and/or 200 μg/ml neomycin (pStbl-neo-CMV-ST3Gal4) and/or 2 μg/ml puromycin (pStbl-Puro-CMV-ST3Gal1), in order to generate stable pools.

Pharmacokinetic Studies of Recombinant C1 Inh in Rats

Comparable pharmacokinetic studies were performed in rats injected with either Berinert (C1 Inh derived from human plasma) or purified recombinant C1 Inh, expressed in CAP C1 Inh, CAP C1 Inh ST3Gal4, or CAP C1 Inh ST3Gal1/ST3GAL4.

Residual hC1 Inh concentrations after i.v. bolus injection of a 10 mg/kg dose in Sprague Dawley female rats were determined at different time points: 5 min, 10 min, 15 min, 20 min, 30 min, 60 min, 2 h, 4 h, 6 h, and 24 h.

Figure 3:
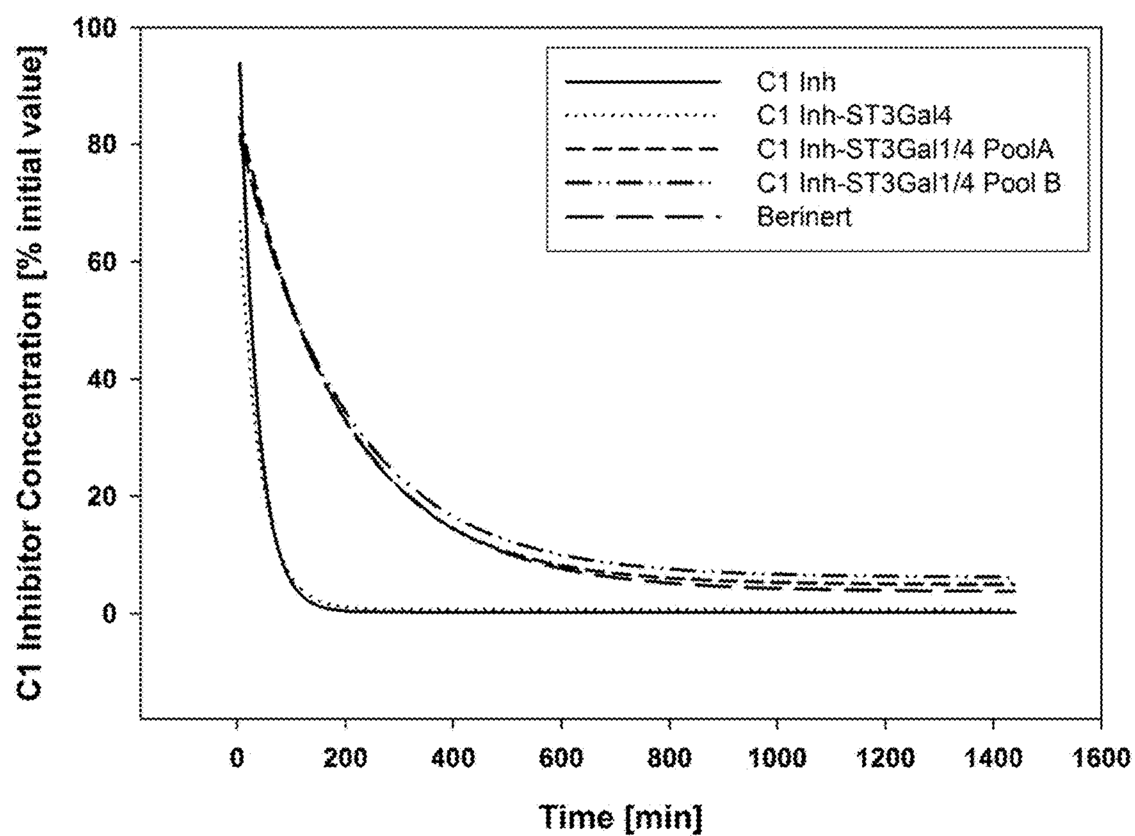
Figure 5:
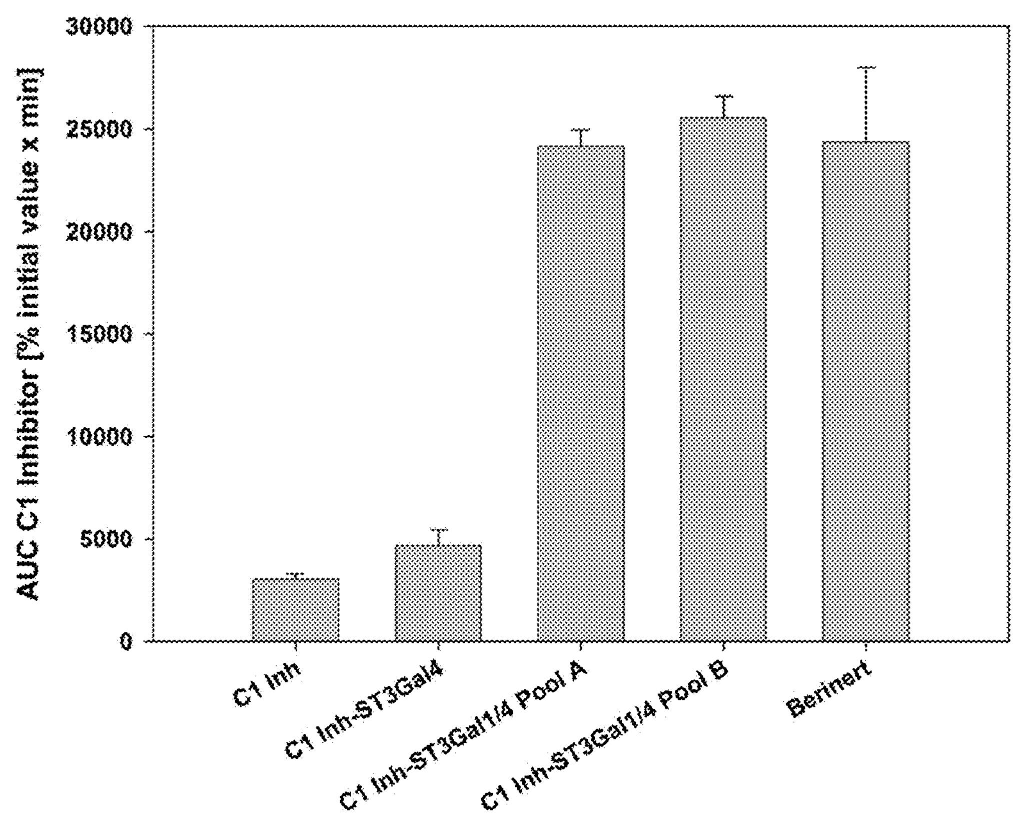

In FIG. 3 the serum concentration of C1 Inh after a single intravenous injection of recombinant C1 Inh or Berinert is shown. The percentage of the residual C1 Inh was detected via ELISA. For each animal C1 Inh concentrations were normalized to the concentration at 5 min=100%. Values were fitted and plotted versus time post injection. From each group (n=4, except Berinert n=7) a graph for one representative animal is shown. In FIG. 5 the area under the curve (AUC) calculations for the different forms of C1 Inh are displayed.

MALDI-TOF-Mass Spectrum Analysis

In order to desalt the samples, 100 μg protein were precipitated twice using chloroform-methanol and dried by vacuum rotation. Glycans were β-eliminated in 50 μL $NaBH_4$ (1 M in 50 mM NaOH) under argon by overnight incubation at 50° C. After desalting with Dowex50×8 (H+) and the removal of borate by co-distillation of the methylester from acidified methanol, the dried residues were methylated as known in the art. MALDI-MS was performed on an UltrafleXtreme instrument (Bruker Daltonics). The methylated glycan alditols were applied to the stainless steel target by mixing 1:1 with matrix (α-cyano-4-hydroxycinnamic acid in 50% acetonitrile/0.1% TFA). Analyses were performed by positive ion detection in MS1 and MS2 (Post-Source-Decay-Modus). Identification of the different glycan species were based i) on the molecule ions, which give information about the monosaccharide composition and ii) the fragmentation in the MS2 analysis (B, C, Y, and Z ions).

PNGaseF Digestion

PNGaseF is an amidase that cleaves between the innermost GlcNAc and asparagine residues of N-linked glycoproteins. Therefore, after treatment of C1 Inh proteins with PNGaseF the protein backbone and the O-linked glycans remain. As the protein backbone between the plasma derived human C1 Inh and C1 Inh expressed in CAP cells is equal, the PNGaseF treatment carries indirectly information about the structure of the O-glycans.

The PNGaseF digestion was done as described in the manufacturer's instructions. Briefly, 100 ng purified protein were incubated with 500 U PNGaseF (NEB) for 1 h at 37° C. Subsequently, samples were separated on a NuPAGE Novex 4-12% Bis-Tris Gel under reducing conditions, according to the manufacturer's instructions. The separated proteins were transferred via an Blot Module (Invitrogen) (30 V for 60 min. at RT) onto an Amersham Hybond ECL membrane (100 V for 60 min at RT). The membrane was blocked for 1 h at RT with PBSTB (phosphate-buffered saline, pH=7.4, supplemented with 0.1% Tween 20 and 1% BSA). Afterwards, the membrane was incubated with the mouse monoclonal C1 Inh specific HRP-labeled antibody diluted 1:10000 in PBSTB. After washing the membrane with PBST (phosphate-buffered saline pH=7.4 supplemented with 0.1% Tween 20), the proteins were detected using the Pierce ECL WB Substrate Kit via a chemiluminescence detector (INTAS).

Lectin Immunoblotting

Lectins are proteins that bind specific carbohydrate structures. Biotin-coupled lectins can be therefore used to analyze N-linked and O-linked glycans. *Erythrina crista galli* (ECL) lectin detects β1-4 linked terminal galactose on N-linked glycans, peanut agglutinin (PNA) detects β1-3 linked terminal galactose on O-linked glycans, *Sambucus nigra agglutinin* (SNA) preferentially binds to a 2,6-linked sialic acid, whereas *Maackia amurensis lectin* (MAL) preferentially binds to 2,3-linked sialic acids.

Purified protein or cell culture supernatants with or without co-expression of ST3Gal1 and/or ST3Gal4 were separated as described above and blotted onto Hybond ECL nitrocellulose membrane (GE healthcare). The membrane was blocked for 1 h at RT with PBSTB (phosphate-buffered saline, pH=7.4, supplemented with 0.1% Tween 20 and 1% BSA). Afterwards, the membrane was incubated with the lectin diluted 1:2000 (MAL 1:400) in PBSTB. After washing the membrane with PBST (phosphate-buffered saline, pH=7.4, supplemented with 0.1% Tween 20), the membrane was stained with streptavidin-coupled horseradish peroxidase for 1 h at RT (1:1000 diluted in PBSTB). The HRP signal was amplified using anti-streptavidin IgG and anti IgG-HRP. The proteins were detected using the Pierce ECL WB Substrate Kit via a chemiluminescence detector (INTAS).

IEF Analysis

Isoelectric focusing (IEF) was performed in order to analyze the isoelectric point (pl) of C1 Inh purified from CAP C1 Inh cells, or CAP C1 Inh cells transfected with ST3Gal4 and/or ST3Gal1, respectively. The degree of sialylation correlates with a given proteins acidity and therefore, with its pl. IEF analysis was done according to the manufacturers protocol (Invitrogen). Briefly, 5 μg of purified protein were loaded on pH3-7 gels and subjected to electrophoresis (1 h 100 V, 1 h 200 V, 30 min 500 V). Proteins were stained with SimplyBlue SafeStain according to the manufacturers protocol (Invitrogen).

Example 1

The protease inhibitor C1 esterase inhibitor (C1 Inh) belongs to the serpin superfamily. Its main function is the inhibition of the complement system to prevent spontaneous activation. The 500 aa protein is highly glycosylated with 7 predicted N-glycans and 8 predicted O-linked glycans.

Cells of the human amniocyte cell line CAP 1D5 previously stably transfected to express human recombinant C1 Inhibitor (rhC1 Inh, SEQ ID NO: 3) (CAP-C1 Inh) were nucleofected with a vector encoding for ST3Gal4 linearized with Scal in order to facilitated stable integration of the construct into the genome. The vector contains a drug expression cassette, for selection of stable integration of the linearized construct into the genome. After pool generation, the obtained stable CAP-C1 Inh-ST3Gal4 pool was subject to single cell cloning via limiting dilution. Selected clones were analyzed to proof expression of ST3Gal4. CAP single cell clones expressing ST3Gal4 were then further nucleofected with the gene encoding for ST3Gal1 gene. Cells were selected with antibiotics to obtain a pool of cells stably co-expressing rhC1 Inh, human ST3Gal4 and ST3Gal1 (CAP-C1 Inh-ST3Gal1/4).

In order to generate sufficient amounts of recombinant C1 Inh, the generated CAP-C1 Inh cell lines overexpressing human C1 Inh were cultured as described in experimental procedures. Subsequently, C1 Inh was purified from the cell culture supernatant of the following cell lines: CAP-C1 Inh, CAP-C1 Inh-ST3Gal4, and CAP-C1 Inh-ST3Gal1/4 (pool A and B), as described below.

Cell culture supernatants or purified recombinant C1 Inh and Berinert were analyzed to determine glycostructures.

Figure 6:
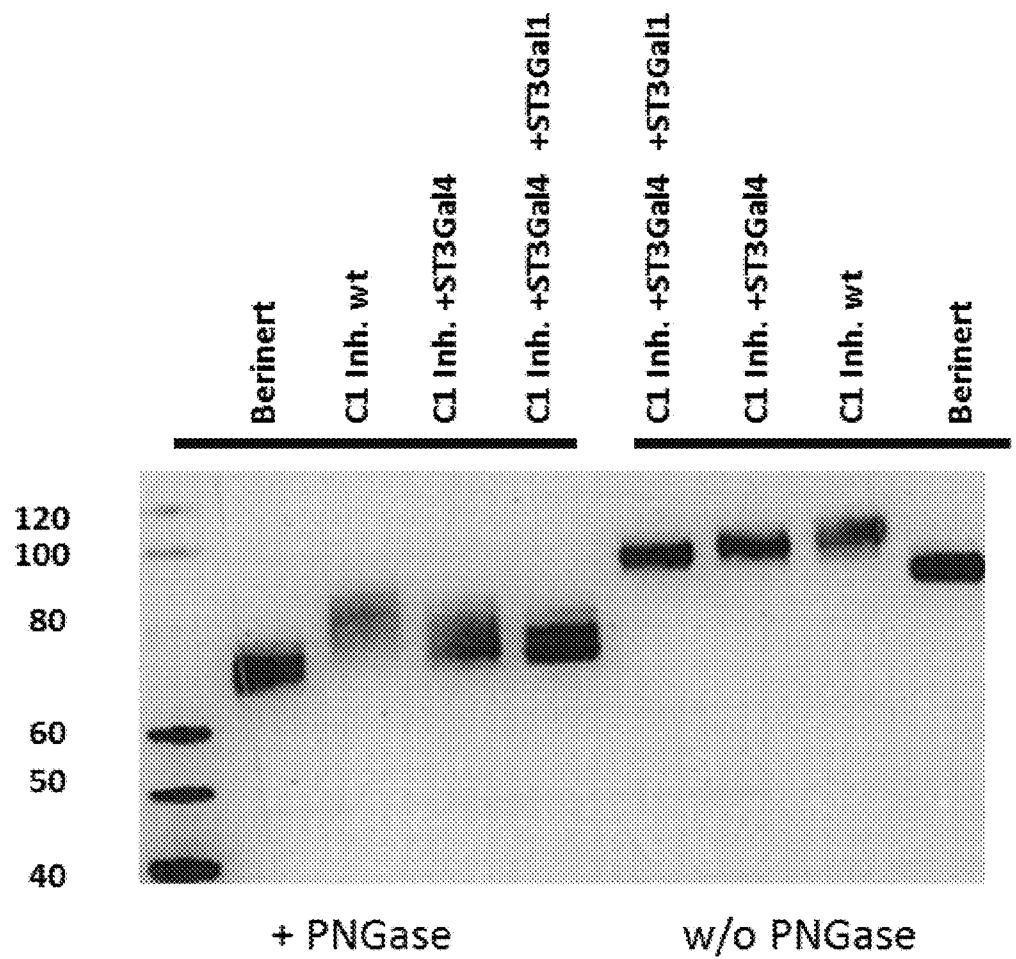

Immunoblotting with a C1 Inh specific antibody (FIG. 6) reveals that C1 Inh purified from plasma (Berinert) migrates faster during electrophoresis, indicating a diminished mass in comparison to recombinant C1 Inh from CAP cells. Overexpression of the sialyltransferases ST3Gal1 in combination with ST3Gal4 likewise increases migration speed. This effect is even more apparent after cleavage of N-linked glycans from the protein backbone by PNGase digestions, indicating that the faster migration is actually due to size differences in the remaining O-linked glycans.

Figure 7:
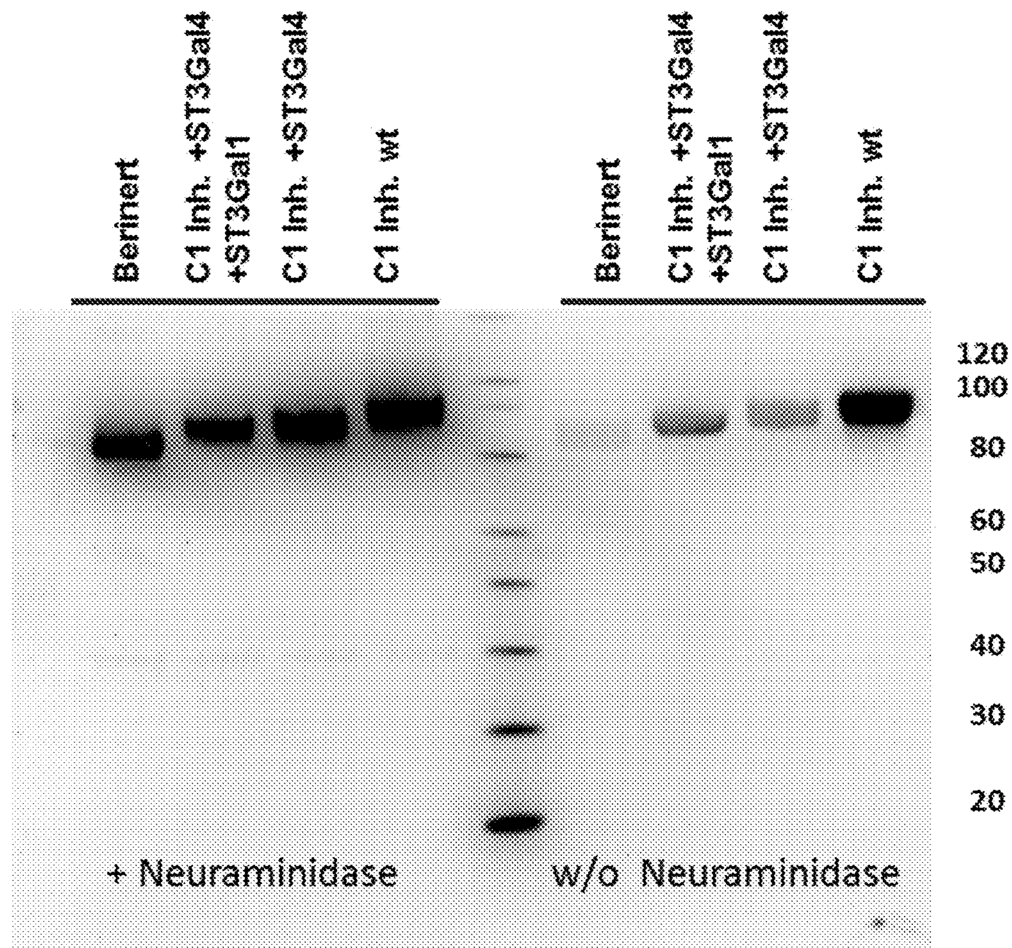

To determine the degree of sialylation of the N-linked glycans, an ECL lectin immunoblot was performed. *Erythrina crista galli* (ECL) lectin detects β1-4 linked terminal galactose on N-linked glycans. Therefore, a diminished signal in the ECL blot means an increased amount of sialylation. As shown in FIG. 7, the N-linked glycans of Berinert are almost completely sialylated. N-Glycans of the C1 Inh from CAP cells overexpressing ST3Gal4 are equally sialylated, C1 Inh from CAP cells overexpressing ST3Gal1/4 display a slightly higher amount of asialo N-glycans. In comparison, C1 Inh purified from CAP cells without overexpression of sialyltransferase give a strong signal in the ECL blot indicating a large amount of asialo N-glycans.

Figure 8:
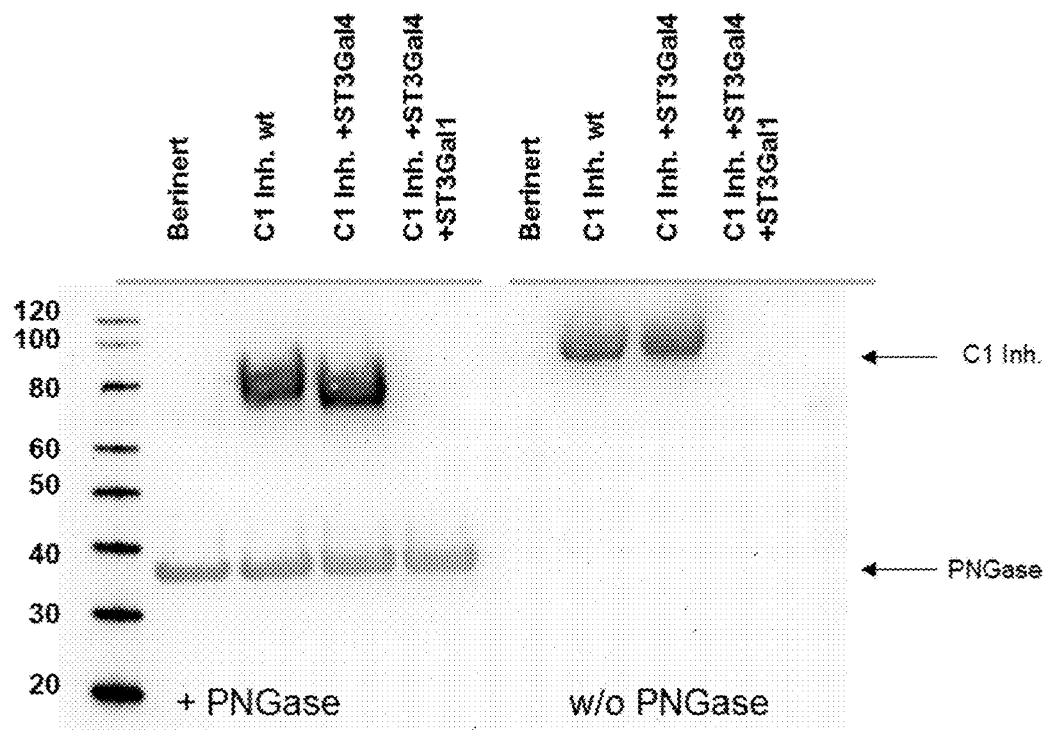

The degree of sialylation of O-linked glycans of recombinant C1 Inh in CAP cells upon overexpression of ST3Gal1 was initially tested by PNA lectin immunoblots. Peanut agglutinin (PNA) detects β1-3 linked terminal galactose on O-linked glycans. Therefore, a diminished signal in the PNA lectin blot implies an increased level of sialylation of the galactose residues of O-glycans. As depicted in FIG. 8, C1 Inh purified from cell culture supernatants of CAP cells overexpressing ST3Gal1 displays no signal indicating complete sialylation of the O-glycans. The same is true for plasma derived C1 Inh, Berinert.

Figure 9:
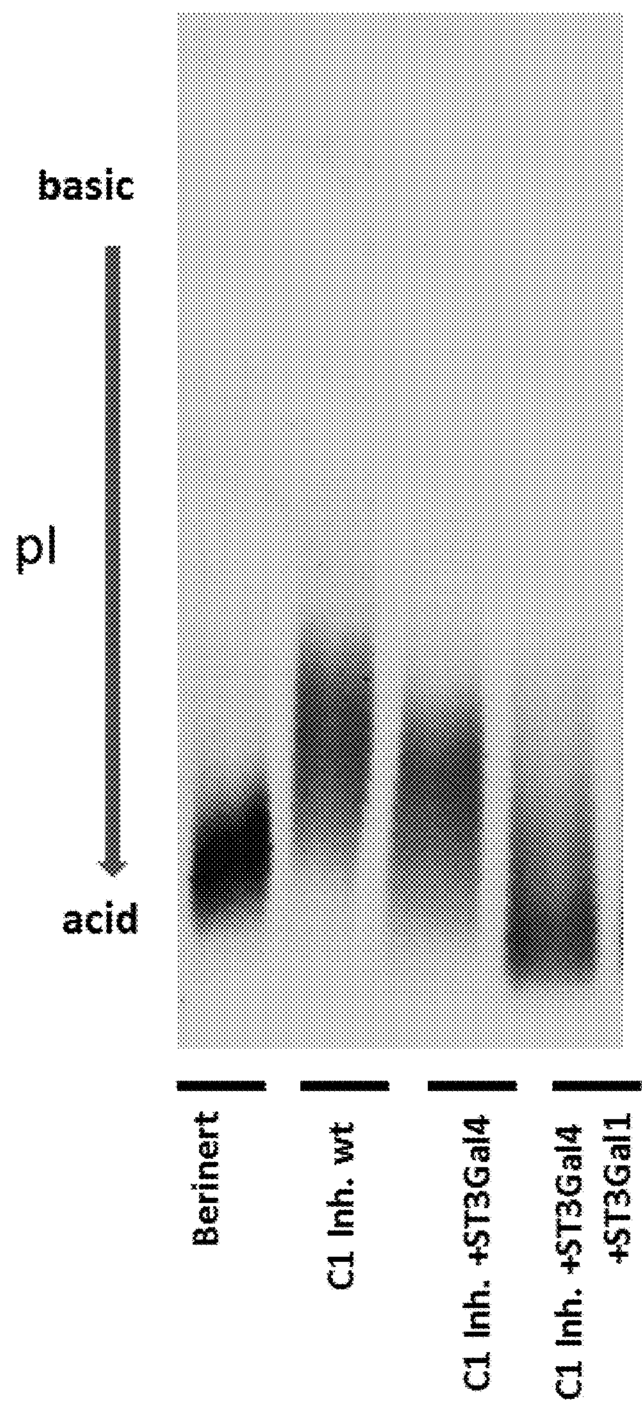
Figure 10A:
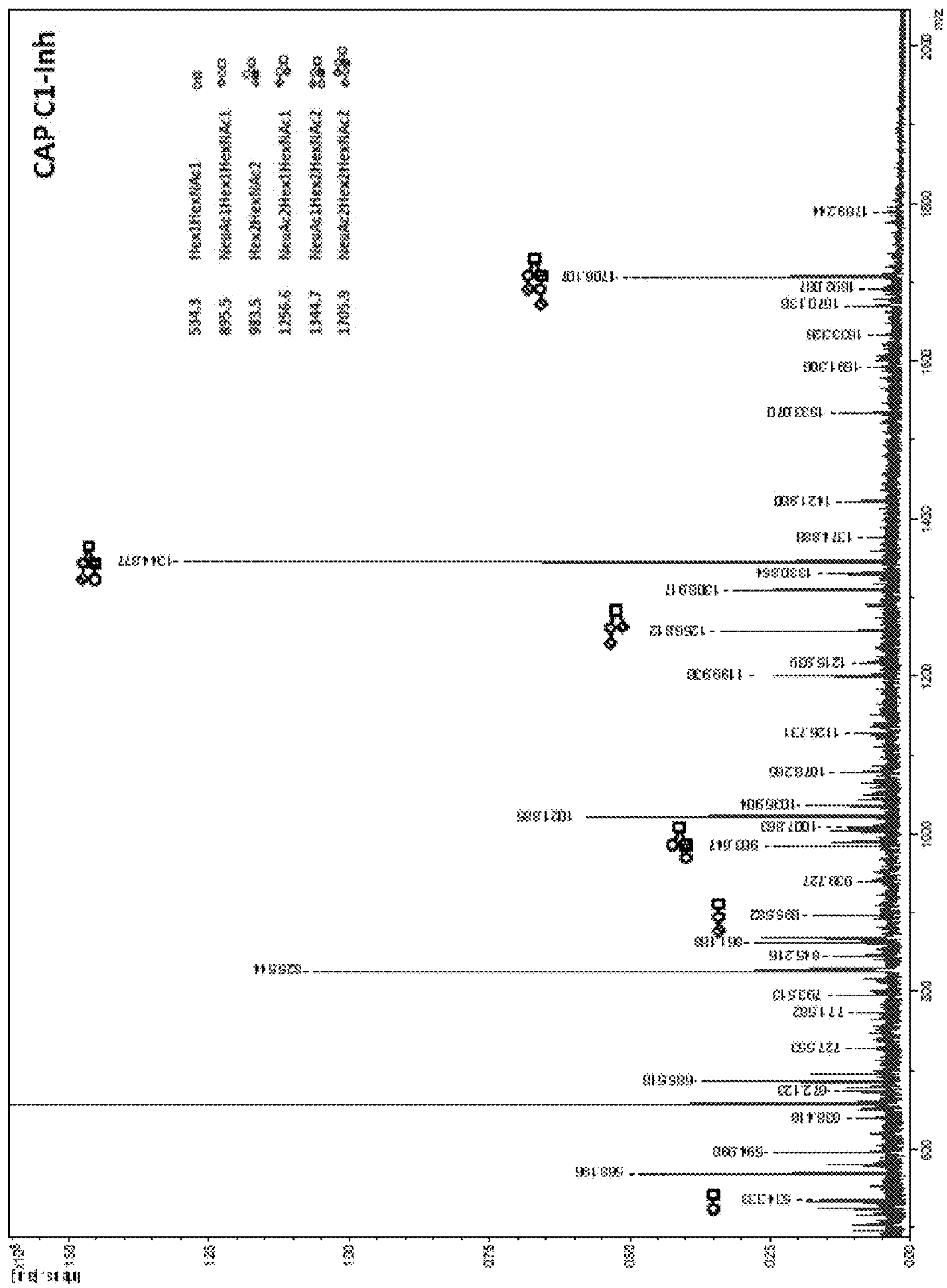
Figure 10B:
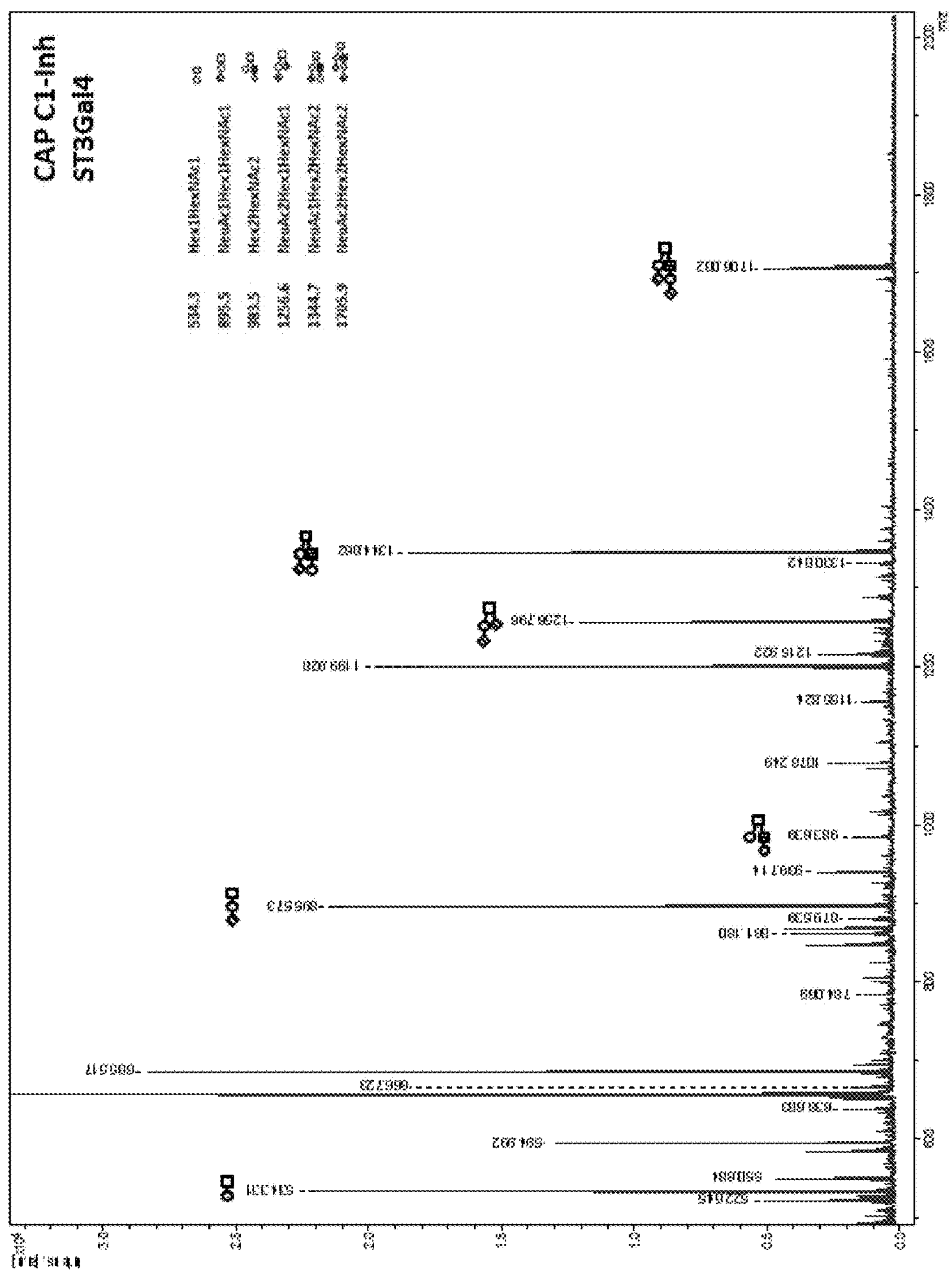
Figure 10C:
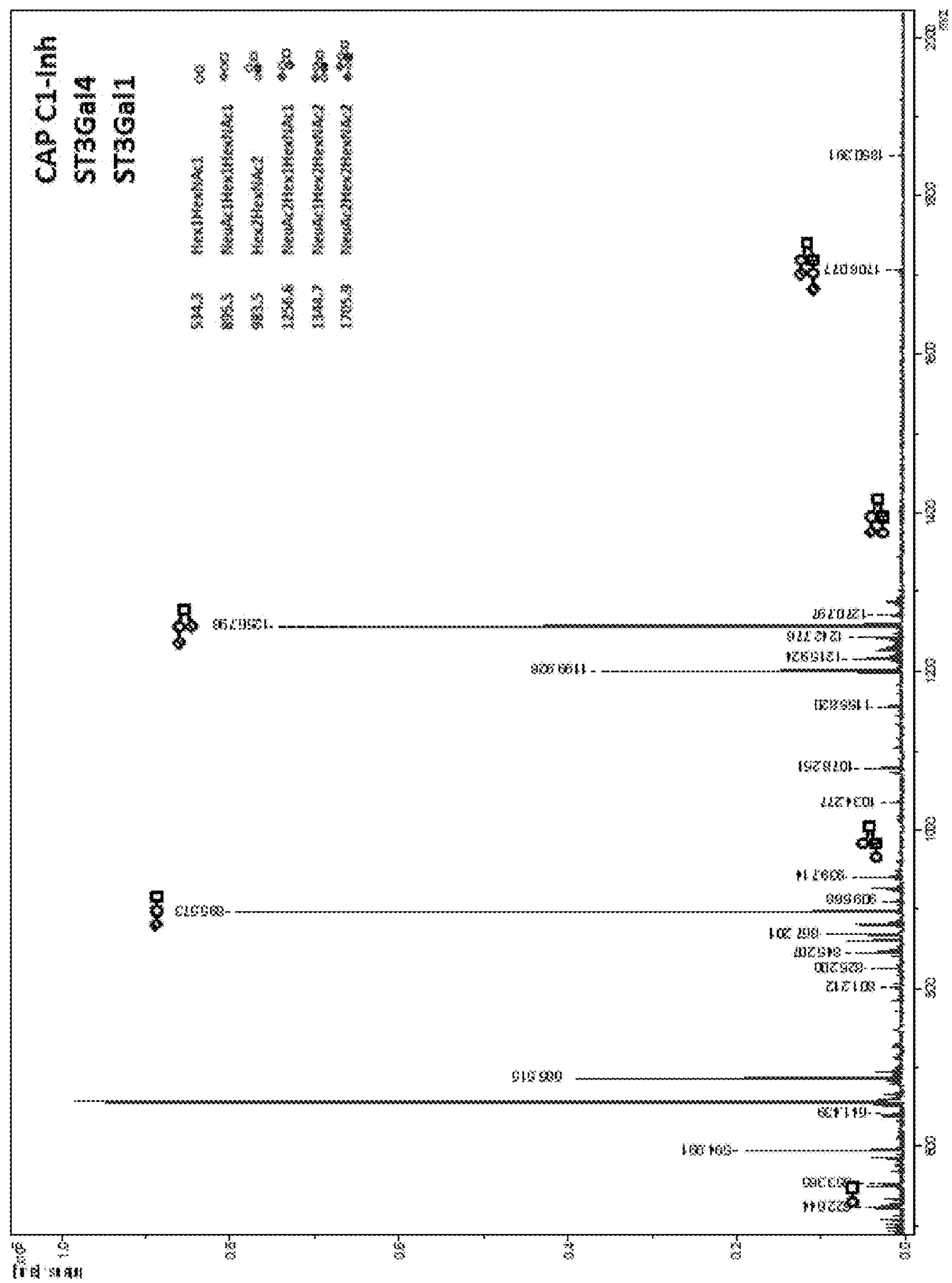
Figure 10D:
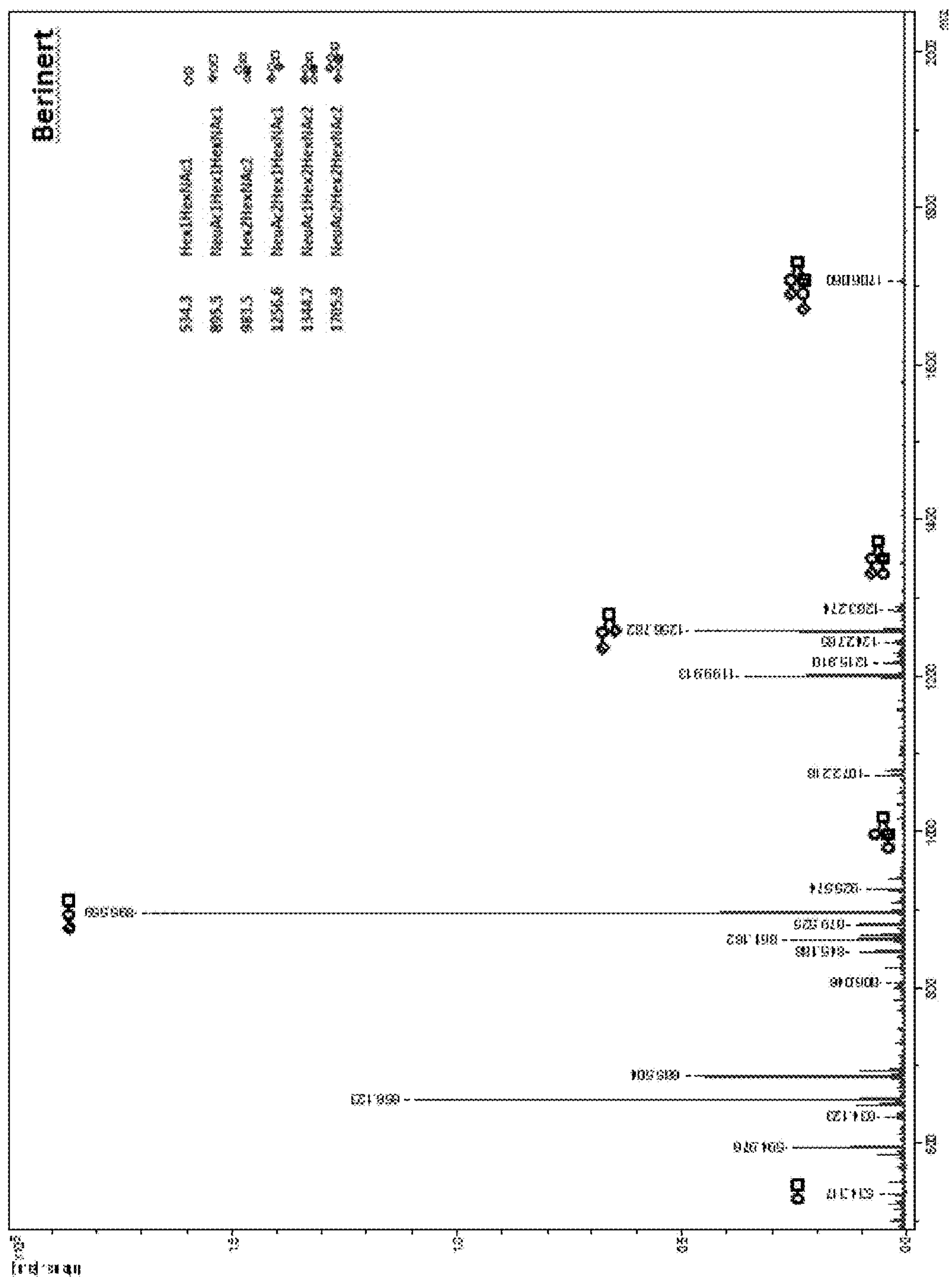

Results from the lectin blots could be confirmed by isoelectric focusing (IEF). As the backbones of the different C1 Inh are identical, changes in the IEF are most likely due to changes in the sialic acid content. As shown in FIG. 9, by additional expression of ST3Gal4, the resulting modified C1 Inh shifts very slightly towards the anode, indicating a small increase in the total amount of sialic acids per molecule. In contrast, the additional expression of ST3Gal1 results in a pronounced shift of C1 Inh towards the anode, indicating a significant increase in the total amount of sialic acids.

Figure 12:
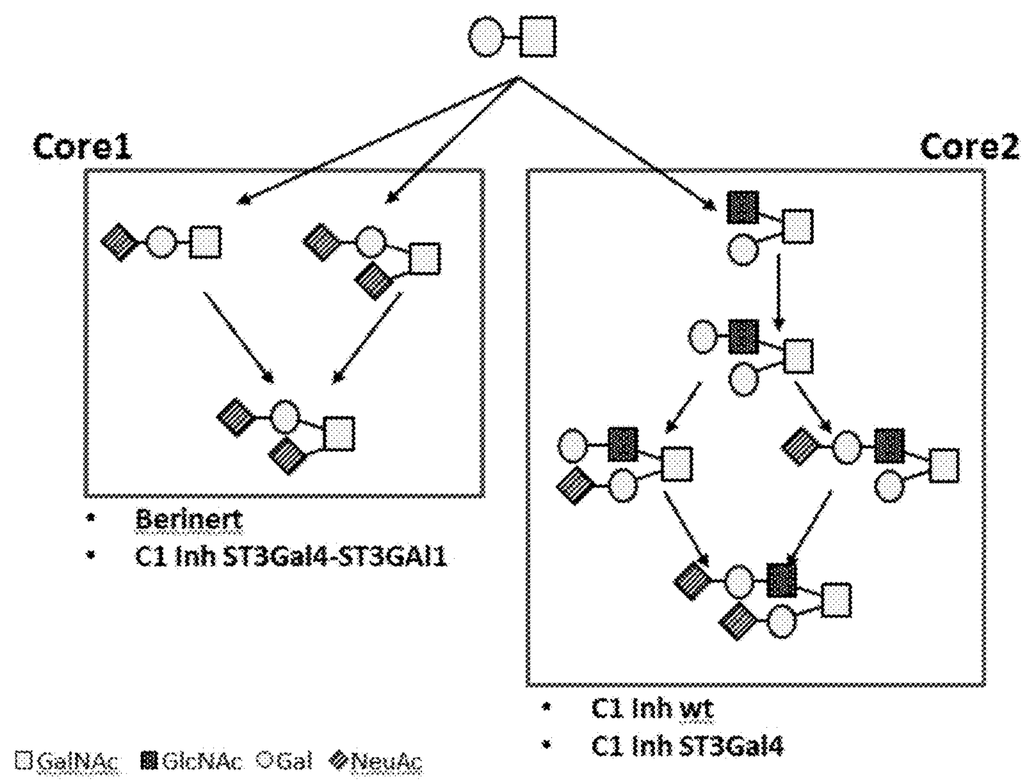

In FIG. 10, detailed MALDI-TOF-mass spectra of the O-linked glycans are displayed. In FIG. 11, these data are summarized by outlining the peak intensity for the different O-glycan structures. FIG. 12 shows an interpretation of the obtained data. In the CAP C1 Inh samples without additional overexpression of ST3Gal1 or ST3Gal4, namely CAP C1 Inh, 75% of the detectable O-glycans are core 2 structure with only 35% sialylated O-glycans without terminal galactose residues(Gal1-3(Gal1-GlcNAc1-6)GalNAc-ol_Core 2) (m/z 983), or NeuAc2-3Gal1-3(Gal1-4GlcNAc1-6)GalNAc-ol (m/z 1344), Gal1-3(NeuAc2-3Gal1-4GalNAc-ol (m/z 1344) and NeuAc2-3Gal1-3(NeuAc2-3Gal1-4GlcNAc1-6)GalNAc-ol (m/z 1706)). Core 1 structures are only rarely detectable. Additional expression of ST3Gal4 leads to a shift towards core 1 structures (68.7%)(NeuAc2-3Gal1-3GalNAc-ol_Core 1). Interestingly, the expression of C1 Inh in CAP cells coupled with the overexpression of ST3Gal1 leads to the exclusive expression of core 1 O-glycans (99.1%) which are almost entirely sialylated (98.5%) without any terminal galactose residues, in particular (NeuAc2-3Gal1-3GalNAc-ol respectively Gal1-3(NeuAc2-6)GalNAc-ol (m/z 895) and NeuAc2-3Gal1-3(NeuAc2-6)GalNAc-ol (m/z 1256).

In order to determine the serum half-life of the different glyco-improved recombinant C1 Inh, CAP-C1 Inh-ST3Gal4, and CAP-C1 Inh-ST3Gal1/4, versus recombinant C1 Inh from CAP cells (wild-type), or plasma derived C1 Inh (Berinert), pharmacokinetic studies were performed.

After normalizing the concentration time curves of the different samples, it became clear that the different samples cluster into two distinct groups with almost the same shape and curve progression: on the one hand, the CAP C1 Inh without further expression of any sialyltransferases together with CAP-C1 Inh-ST3Gal4 and on the other hand CAP-C1 Inh-ST3Gal1/4 together with the plasma derived human C1 Inh, Berinert (FIG. 3). The substances in one group are eliminated from the blood stream in the same manner following the same pharmacokinetics.

Figure 4:
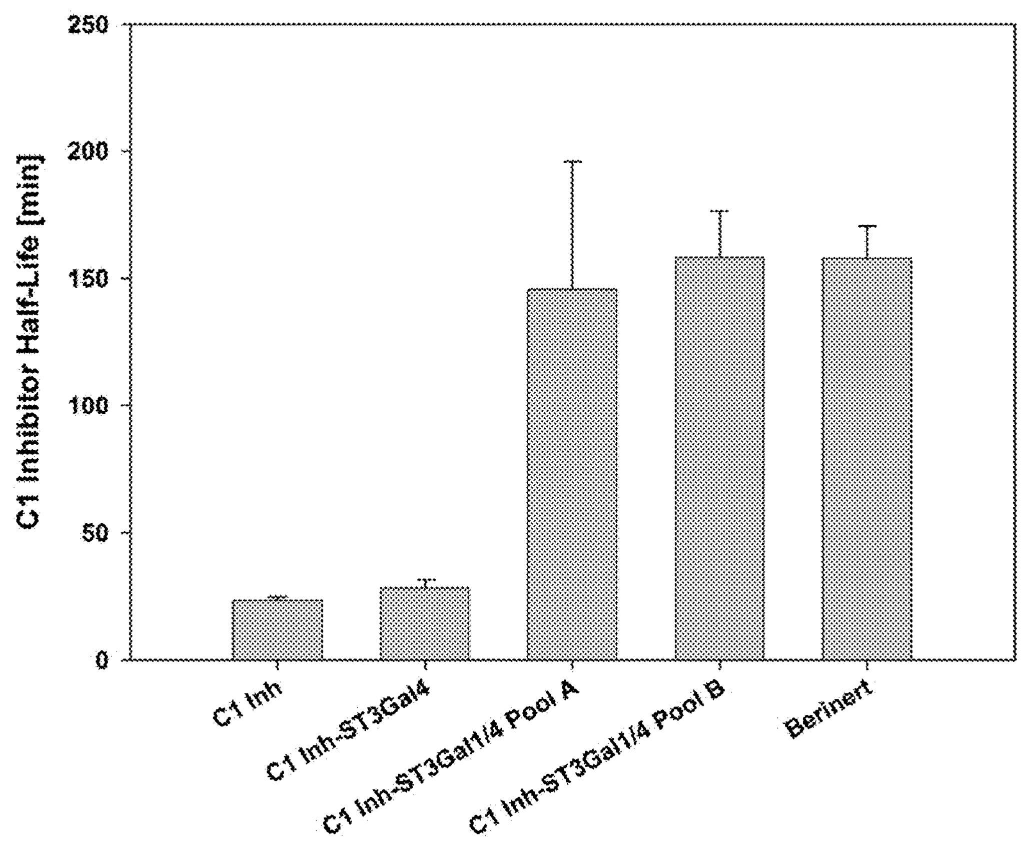

While overexpression of ST3Gal4 alone had no beneficial effect on serum half-life of the recombinantly expressed C1 Inh, the additional co-expression of ST3Gal1 enhanced serum half-life about 6-fold (FIG. 4). AUC and therefore the bioavailability increase around 6 fold compared to the unmodified C1 Inh and is equivalent to the AUC values measured for Berinert (FIG. 5). Briefly, these results point out that for glycoproteins exhibiting N-glycans as well as O-glycans, broad sialylation of the O-glycans is as important as it is for the N-glycans.

Example 2

Hepatocyte growth factor is a potent mitogen for mature parenchymal hepatocyte cells, seems to be a hepatotrophic factor, and acts as a growth factor for a broad spectrum of tissues and cell types. The 728 aa sized protein contains 4 predicted N-glycans and 1 predicted O-linked glycan.

CAP 1D5 cells stably expressing human recombinant hepatocyte growth factor (SEQ ID NO: 4) were nucleofected either with a vector encoding for ST3Gal4, ST3Gal1, or ST3Gal4 and ST3Gal1 linearized with Scal in order to facilitate stable integration of the construct into the genome. The vectors contain a drug expression cassette, which facilitates selection for cells with a stable integration of the linearized construct into the genome. After pool generation the obtained stable CAP cell pools, CAP-HGF, CAP-HGF-ST3Gal1, CAP-HGF-ST3Gal4, and CAP-HGF-ST3Gal1/4 were cultured as described in experimental procedures. Cell culture supernatants containing recombinant human HGF were examined by ECL and PNA lectin blots to determine the existing N- and O-linked glycostructures.

Figure 13:
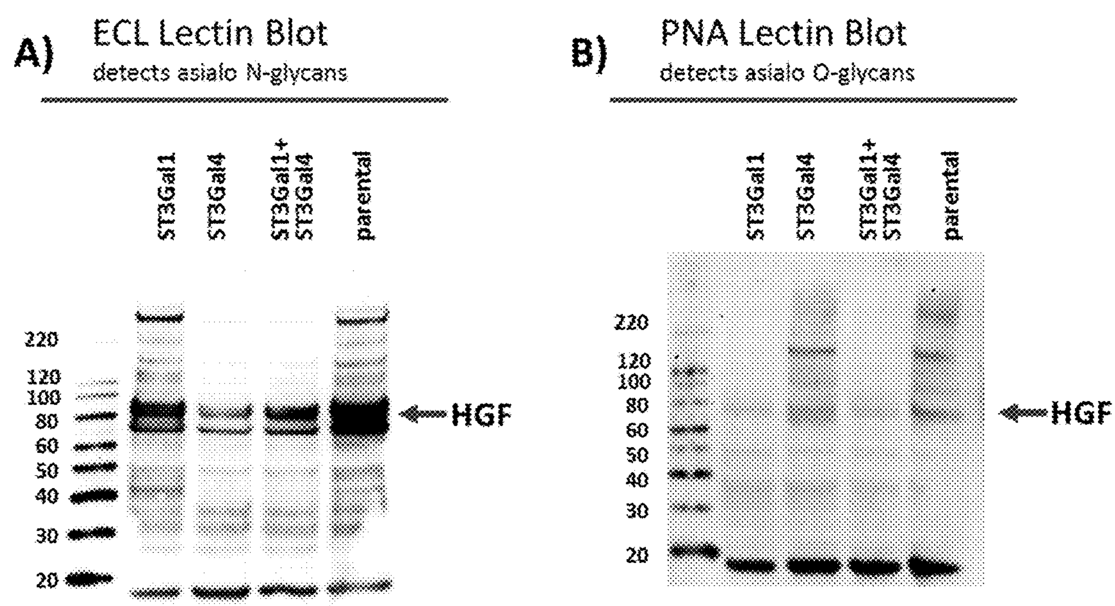

*Erythrina crista galli* (ECL) lectin detects β1-4 linked terminal galactose on N-linked glycans. Therefore a diminished signal in the ECL blot means an increased amount of sialylation. As shown in FIG. 13, overexpression of ST3Gal4 or ST3Gal1/4 results in an increased sialylation of the N-linked glycans, whereas overexpression of ST3Gal1 has no effect.

The amount of sialylation of recombinant HGF in CAP cells upon overexpression of ST3Gal1 was tested by PNA lectin immunoblots. Peanut agglutinin (PNA) detects β1-3 linked terminal galactose on O-linked glycans. Therefore, a decreased signal in the PNA lectin blot implies an increased level of sialylation of the galactose residues of O-glycans. As depicted in FIG. 13, overexpression of ST3Gal1 alone or in combination with ST3Gal4 resulted in a significant increase in sialylation of the O-glycan of recombinant HGF.

Example 3

The following experiment was executed in order to investigate if the observed increased sialylation of the O-glycans of glycoproteins upon overexpression of the sialyltransferase ST3Gal1 is common feature shared by diverse cell lines utilized for the manufacture of recombinant proteins or viruses for pharmaceutical production and/or biomedical research.

293F cells (Life Technologies, R-970-07), immortalized human embryonic kidney cells, were nucleofected either with a vector encoding for ST3Gal1, or ST3Gal1 and ST3Gal4 linearized with Scal in order to facilitate stable integration of the construct into the genome. The vectors contain a drug expression cassette, which facilitates selection for cells with a stable integration of the linearized construct into the genome. After pool generation the obtained stable 293F cell pools, 293F-ST3Gal1, and 293F-ST3Gal1/4 and wildtype 293F cells were further nucleofected with the gene encoding for hC1 Inh. Cells were selected with antibiotics to obtain pools of cells stably expressing i) rhC1 Inh, ii) rhC1 Inh and human ST3Gal1, iii) rhC1 Inh, human ST3Gal1, and human ST3Gal4. C1 Inh was purified from C1 Inh containing cell culture supernatant as described in the method section and examined by ECL and PNA ectin blots to determine the existing N- and O-linked glycostructures.

Figure 15:
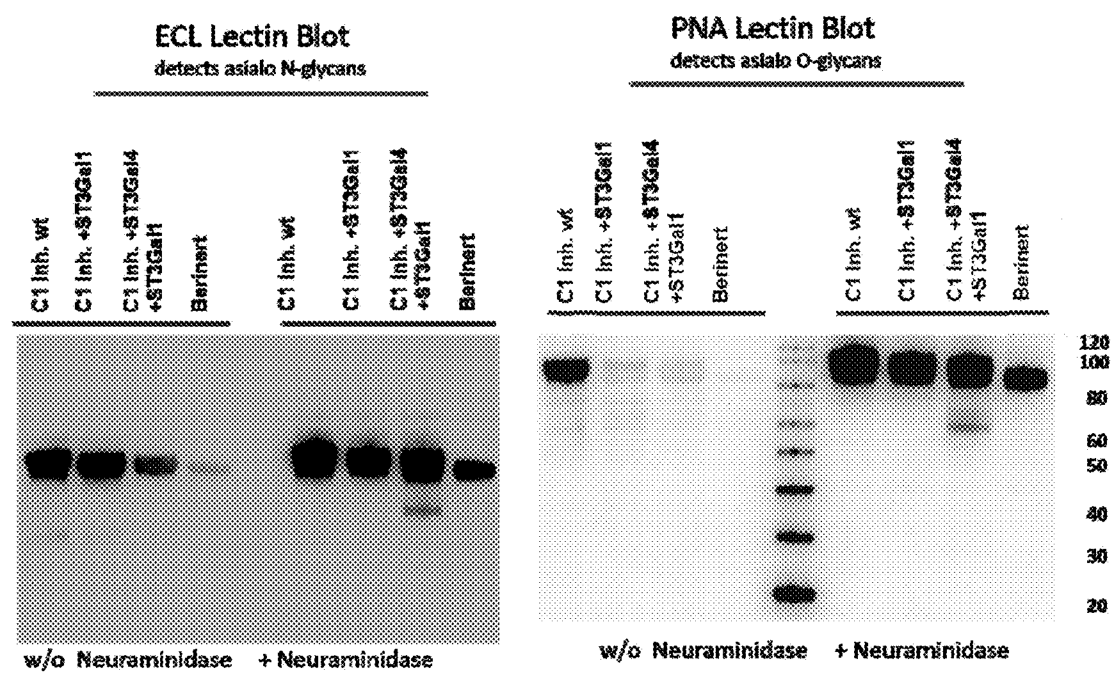

*Erythrina crista galli* (ECL) lectin detects β1-4 linked terminal galactose on N-linked glycans. Therefore a diminished signal in the ECL blot means an increased amount of sialylation. As shown in FIG. 15, overexpression of ST3Gal1/4 results in an increased sialylation of the N-linked glycans, whereas overexpression of ST3Gal1 alone has no effect.

The amount of sialylation of recombinant C1 Inh in 293F cells upon overexpression of ST3Gal1 was tested by PNA lectin immunoblots. Peanut agglutinin (PNA) detects β1-3 linked terminal galactose on O-linked glycans. Therefore, a decreased signal in the PNA lectin blot implies an increased level of sialylation of the galactose residues of O-glycans. As depicted in FIG. 15, overexpression of ST3Gal1 alone or in combination with ST3Gal4 resulted in a significant increase in sialylation of the O-glycan of recombinant human C1Inh.

Example 4

CHO-K1 (ATCC, CCL-61) cell line was derived as a subclone from the parental CHO cell line initiated from a biopsy of an ovary of an adult Chinese hamster.

In order to investigate if the observed increased sialylation of O-linked glycans upon overexpression of human sialyltranserase ST3Gal1 also takes place in non-human mammalian cell lines, human C1 Inh was expressed in these cells in the presence or absence of the sialyltransferase ST3Gal1.

CHO-K1 cells were nucleofected with a vector encoding for ST3Gal1 linearized with Scal in order to facilitate stable integration of the construct into the genome. The vector contains a drug expression cassette, which facilitates selection for cells with a stable integration of the linearized construct into the genome. After pool generation the obtained stable CHO-K1 cell pool, CHO-ST3Gal1, and wildtype CHO-K1 cells were further nucleofected with the gene encoding for hC1 Inh. Cells were selected with antibiotics to obtain pools of cells stably expressing i) rhC1 Inh, ii) rhC1 Inh and human ST3Gal1.

Cells were expanded as described in the method section. For the production of cell culture supernatant containing human C1 Inh cells were seeded in 10 cm cell culture dishes, 3 d post seeding cells were extensively washed with 1×PBS in order to remove fetal bovine serum, subsequently adding fresh serum free media. Four days later cell culture supernatant were harvest, cells and cell debris were removed by centrifugation and filtration via a 0.22 μm filter. C1 Inh was purified as described in the method section.

Figure 16:
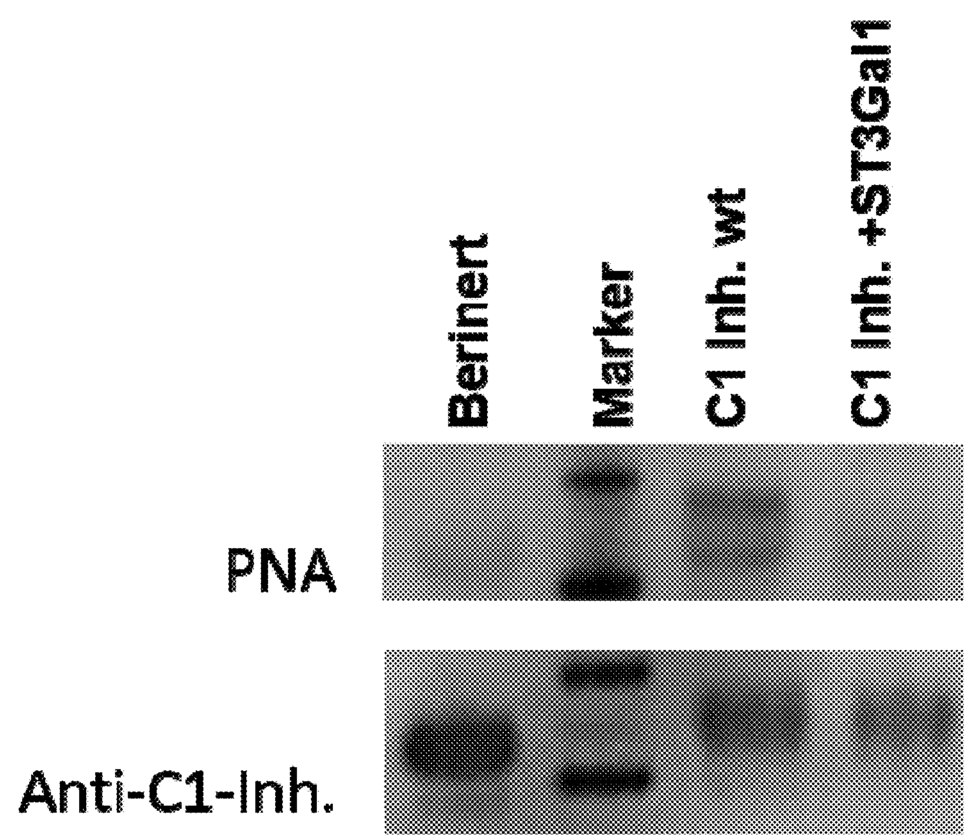

The amount of sialylation of O-glycans of recombinant C1 Inh in CHO-K1 cells upon overexpression of ST3Gal1 was tested by PNA lectin immunoblots. Peanut agglutinin (PNA) detects β1-3 linked terminal galactose on O-linked glycans. Therefore, a decreased signal in the PNA lectin blot implies an increased level of sialylation of the galactose residues of O-glycans. As shown in FIG. 16, overexpression of ST3Gal1 alone resulted in a significant increase in sialylation of the O-glycan of recombinant human C1 Inh.

Example 5

Canine MDCK.1 cells (ATCC, CRL-2935) were stably transfected. The resulting stable MDCK.1 cell pool, MDCK.1-ST3Gal1, and wildtype MDCK.1 cells were further stably transfected to obtain pools of cells stably expressing i) rhC1 Inh, ii) rhC1 Inh and human ST3Gal1.

MDCK.1 cells were expanded as described in the method section. For the production of cell culture supernatant containing human C1 Inh cells were seeded onto 225 $cm^2$ cell culture dishes, 2 d post seeding cells were extensively washed with 1×PBS in order to remove fetal bovine serum, subsequently adding fresh serum free media. Five days later cell culture supernatant were harvest, cells and cell debris were removed by centrifugation and filtration via a 0.22 μm filter. C1 Inh was purified as described in the method section and examined by ECL and PNA lectin blots to determine the existing N- and O-linked glycostructures.

Figure 17:
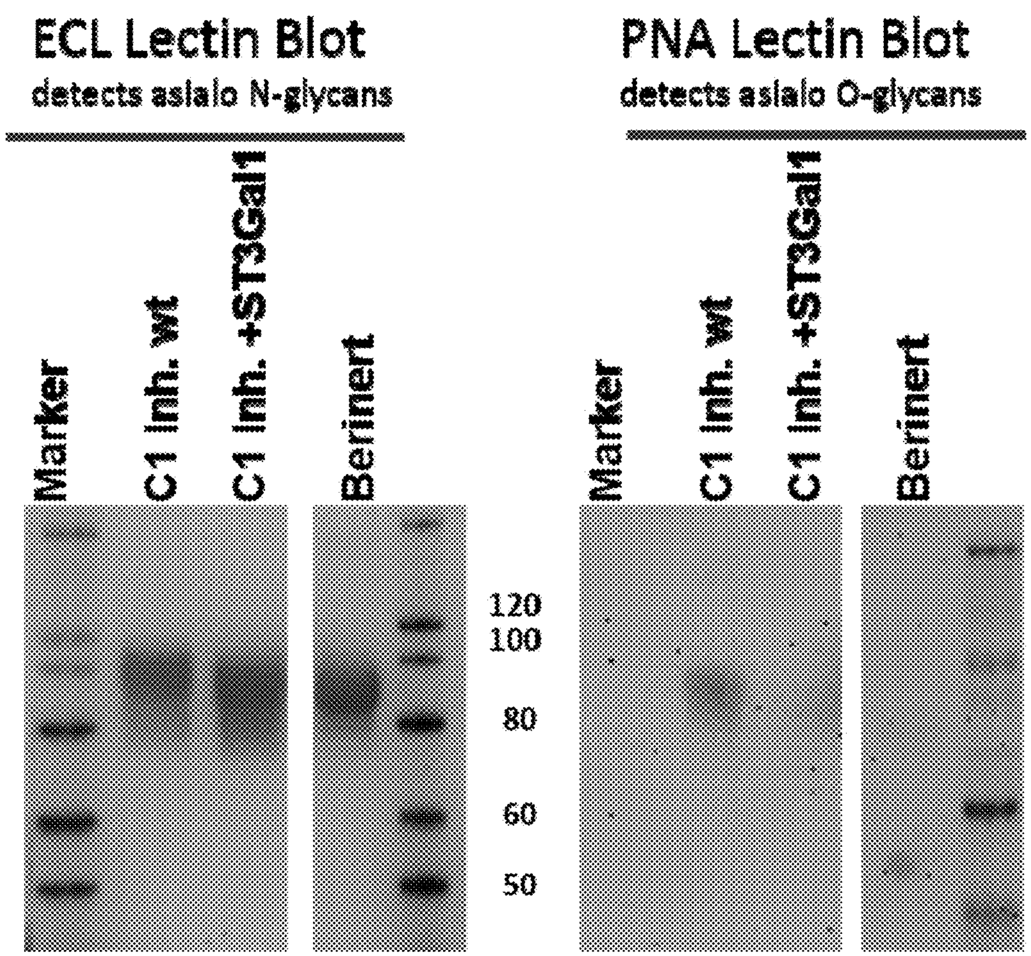

*Erythrina crista galli* (ECL) lectin detects β1-4 linked terminal galactose on N-linked glycans. Therefore a diminished signal in the ECL blot means an increased amount of sialylation. As shown in FIG. 17, overexpression of ST3Gal1 does not result in an increased sialylation of the N-linked glycans.

The amount of sialylation of O-glycans of recombinant C1 Inh in MDCK.1 cells upon overexpression of ST3Gal1 was tested by PNA lectin immunoblots. Peanut agglutinin (PNA) detects β1-3 linked terminal galactose on O-linked glycans. Therefore, a decreased signal in the PNA lectin blot implies an increased level of sialylation of the galactose residues of O-glycans. As shown in FIG. 17, overexpression of ST3Gal1 alone resulted in a significant increase in sialylation of the O-glycans of recombinant human C1 Inh.

Discussion:

In the experiments presented above, an ST3Gal1 catalyzing the transfer of sialic acid from CMP-sialic acid to galactose-containing substrates was overexpressed in mammalian cells, either alone or in combination with an ST3Gal4.

Overexpression of ST3Gal1 resulted in nearly complete sialylation of co-expressed O-glycosylated recombinant proteins. Additionally, the heterogeneity of the GalNAc O-glycans was significantly reduced.

Surprisingly, the overexpression of ST3Gal4 alone had no effect on the pharmacokinetic profile of the examined glycoprotein, whereas additional overexpression of ST3Gal1 and the resulting increase in the degree of sialylation of the GalNAc O-glycans increased the serum half-life about 6-fold.

Modifying the glycan structures of therapeutic proteins in order to improve their pharmacokinetic profile is a very potent tool. In the case of the present invention, in particular two common weaknesses of therapeutic proteins are addressed, first the limited serum half-life and second the heterogeneity of glyco-structures. This can be achieved by a forced expression of ST3Gal1 enzyme resulting in secreted glycoproteins showing nearly complete sialylation of GalNAc O-glycans.

This invention is not limited to one particular cell line from one host but is rather applicable to a broad range of animal cell lines. Additionally, it is not restricted to one particular group of glycoproteins but is applicable to a wide range of glycoproteins containing at least one GalNAc O-linked glycan, e.g. growth factors, peptide hormones, cytokines, enzymes, antibodies, antibody fragments, blood clotting factors, or protease inhibitors.

The present invention relates to the following amino acid and nucleotide sequences.

SEQ ID NO: 1

Human ST3Gal1

```
MVTLRKRTLK VLTFLVLFIF LTSFFLNYSH TMVATTWFPK QMVLELSENL KRLIKHRPCT   60
CTHCIGQRKL SAWFDERFNQ TMQPLLTAQN ALLEDDTYRW WLRLQREKKP NNLNDTIKEL  120
FRVVPGNVDP MLEKRSVGCR RCAVVGNSGN LRESSYGPEI DSHDFVLRMN KAPTAGFEAD  180
VGTKTTHHLV YPESFRELGD NVSMILVPFK TIDLEWVVSA ITTGTISHTY IPVPAKIRVK  240
QDKILIYHPA FIKYVFDNWL QGHGRYPSTG ILSVIFSMHV CDEVDLYGFG ADSKGNWHHY  300
WENNPSAGAF RKTGVHDADF ESNVTATLAS INKIRIFKGR                        340
```

SEQ ID NO: 2

Human ST3Gal4

```
MVSKSRWKLL AMLALVLVVM VWYSISREDR YIELFYFPIP EKKEPCLQGE AESKASKLFG   60
NYSRDQPIFL RLEDYFWVKT PSAYELPYGT KGSEDLLLRV LAITSSSIPK NIQSLRCRRC  120
VVVGNGHRLR NSSLGDAINK YDVVIRLNNA PVAGYEGDVG SKTTMRLFYP ESAHFDPKVE  180
NNPDTLLVLV AFKAMDFHWI ETILSDKKRV RKGFWKQPPL IWDVNPKQIR ILNPFFMEIA  240
ADKLLSLPMQ QPRKIKQKPT TGLLAITLAL HLCDLVHIAG FGYPDAYNKK QTIHYYEQIT  300
LKSMAGSGHN VSQEALAIKR MLEMGAIKNL TSF                               333
```

SEQ ID NO: 3
Human C1 Inh

```
MASRLTLLTL LLLLLAGDRA SSNPNATSSS SQDPESLQDR GEGKVATTVI SKMLFVEPIL   60
EVSSLPTTNS TTNSATKITA NTTDEPTTQP TTEPTTQPTI QPTQPTTQLP TDSPTQPTTG  120
SFCPGPVTLC SDLESHSTEA VLGDALVDFS LKLYHAFSAM KKVETNMAFS PFSIASLLTQ  180
VLLGAGENTK TNLESILSYP KDFTCVHQAL KGFTTKGVTS VSQIFHSPDL AIRDTFVNAS  240
RTLYSSSPRV LSNNSDANLE LINTWVAKNT NNKISRLLDS LPSDTRLVLL NAIYLSAKWK  300
TTFDPKKTRM EPFHFKNSVI KVPMMNSKKY PVAHFIDQTL KAKVGQLQLS HNLSLVILVP  360
QNLKHRLEDM EQALSPSVFK AIMEKLEMSK FQPTLLTLPR IKVTTSQDML SIMEKLEFFD  420
FSYDLNLCGL TEDPDLQVSA MQHQTVLELT ETGVEAAAAS AISVARTLLV FEVQQPFLFV  480
LWDQQHKFPV FMGRVYDPRA                                               500
```

SEQ ID NO: 4
Human HGF

```
MWVTKLLPAL LLQHVLLHLL LLPIAIPYAE GQRKRRNTIH EFKKSAKTTL IKIDPALKIK   60
TKKVNTADQC ANRCTRNKGL PFTCKAFVFD KARKQCLWFP FNSMSSGVKK EFGHEFDLYE  120
NKDYIRNCII GKGRSYKGTV SITKSGIKCQ PWSSMIPHEH SFLPSSYRGK DLQENYCRNP  180
RGEEGGPWCF TSNPEVRYEV CDIPQCSEVE CMTCNGESYR GLMDHTESGK ICQRWDHQTP  240
HRHKFLPERY PDKGFDDNYC RNPDGQPRPW CYTLDPHTRW EYCAIKTCAD NTMNDTDVPL  300
ETTECIQGQG EGYRGTVNTI WNGIPCQRWD SQYPHEHDMT PENFKCKDLR ENYCRNPDGS  360
ESPWCFTTDP NIRVGYCSQI PNCDMSHGQD CYRGNGKNYM GNLSQTRSGL TCSMWDKNME  420
DLHRHIFWEP DASKLNENYC RNPDDDAHGP WCYTGNPLIP WDYCPISRCE GDTTPTIVNL  480
DHPVISCAKT KQLRVVNGIP TRTNIGWMVS LRYRNKHICG GSLIKESWVL TARQCFPSRD  540
LKDYEAWLGI HDVHGRGDEK CKQVLNVSQL VYGPEGSDLV LMKLARPAVL DDFVSTIDLP  600
NYGCTIPEKT SCSVYGWGYT GLINYDGLLR VAHLYIMGNE KCSQHHRGKV TLNESEICAG  660
AEKIGSGPCE GDYGGPLVCE QHKMRMVLGV IVPGRGCAIP NRPGIFVRVA YYAKWIHKII  720
LTYKVPQS                                                            728
```

SEQ ID NO: 5
ST3Gal1 motif 3 consensus sequence

```
HYWE                4
```

SEQ ID NO: 6
Pan troglodytes ST3Gal1

```
MVTLRKRTLK VLTFLVLFIF LTSFFLNYSH TMVATTWFPK QMVLELSENL KRLIKHRPCT   60
CTHCIGQRKL SAWFDERFNQ TVQPLLTAQN ALLEDDTYRW WLRLQREKKP NNLNDTIKEL  120
FRVVPGNVDP MLEKRSVGCR RCAVVGNSGN LRESSYGPEI DSHDFVLRMN KAPTAGFEAD  180
VGTKTTHHLV YPESFRELGD NVSMILVPFK TIDLEWVVSA ITTGTISHTY VPVPAKIRVK  240
QDKILIYHPA FIKYVFDNWL QGHGRYPSTG ILSVIFSMHV CDEVDLYGFG ADSKGNWHHY  300
WENNPSAGAF RKTGVHDADF ESNVTATLAS INKIRIFKGR                         340
```

SEQ ID NO: 7
Macaca mulatta ST3Gal1

```
MVTLRKRTLK VLTFLVLFIF LTSFFLNYSH TMVTTTWFPK QMVLELSENL KRLIKHRPCT   60
CTHCIGQRKL SVWFDERFNQ TVQPLLTAQN ALLEDDTYRW WLRLQREKKP NNLNDTIKEL  120
FRVVPGNVDP MLEKRSVGCR RCAVVGNSGN LRESSYGPEI DRHDFVLRMN KAPTAGFEAD  180
VGTKTTHHLV YPESFRELGD NVSMILVPFK TIDLEWVVSA TTTGTISHTY VPVPAKIRVK  240
QDKILIYHPA FIKYVFDNWL QGHGRYPSTG ILSVIFSMHV CDEVDLYGFG ADSKGNWHHY  300
WENNPSAGAF RKTGVHDADF ESNVTATLAS INKIRIFKGR                        340
```

SEQ ID NO: 8
Sus scrofa ST3Gal1

```
MAPMRKKSTL KLLTLLVLFI FLTSFFLNYS HTVVTTAWFP KQMVIELSEN FKKLMKYPYR   60
PCTCTRCIEE QRVSAWFDER FNRSMQPLLT AKNAHLEEDT YKWWLRLQRE KQPNNLNDTI  120
RELFQVVPGN VDPLLEKRLV SCRRCAVVGN SGNLKESYYG PQIDSHDFVL RMNKAPTEGF  180
EADVGSKTTH HFVYPESFRE LAQEVSMILV PFKTTDLEWV ISATTTGRIS HTYVPVPAKI  240
KVKKEKILIY HPAFIKYVFD RWLQGHGRYP STGILSVIFS LHICDEVDLY GFGADSKGNW  300
HHYWENNPSA GAFRKTGVHD GDFESNVTTI LASINKIRIF KGR                    343
```

SEQ ID NO: 9
Rattus norvegicus ST3Gal1

```
MVNMRKRTLK YLTFFLLFIF LTSFVLNYSN SGVPSAWFPK QMVLEFSENF RKFIKSQPCT   60
CRHCISQGKV SYWFDQRFNK TMQPLLTAHN ALMEEDTYRW WLRLQRERKP NNLSDTVKEL  120
FRLVPGNVDP MLNKRLVGCR RCAVVGNSGN LKDSSYGPEI DSHDFVLRMN RAPTVGFEAD  180
VGSRTTHHLV YPESFRELGE NVNMVLVPFK ITDLQWVISA TTTGTITHTY VPVPPKIKVK  240
QEKILIYHPA FIKYVFDNWL QGHGRYPSTG ILSVIFSIHI CDEVDLYGFG ADSKGNWHHY  300
WENNPSAGAF RKTGVHDGDF EYNVTTTLAA INKIRIFKGR                        340
```

SEQ ID NO: 10
Mus musculus ST3Gal1

```
MRRKTLKYLT FFLLFIFLTS FVLNYSNTGV PSAWFPKQML LELSENFRRF IKSQPCTCRH   60
CISQDKVSYW FDQRFNKTMQ PLLTVHNALM EEDTYRWWLR LQRERKPNNL SDTVKELFRL  120
VPGNVDPMLN KRLVGCRRCA VVGNSGNLKD SSYGPEIDSH DFVLRMNKAP TVGFEADVGS  180
RTTHHLVYPE SFRELGENVN MVLVPFKTTD LQWVISATTT GTITHTYVPV PPKIKVKQEK  240
ILIYHPAFIK YVFDNWLQGH GRYPSTGILS IIFSIHICDE VDLYGFGADS KGNWHHYWEN  300
NPSAGAFRKT GVHDGDFEYN ITTTLAAINK IRIFKGR                           337
```

SEQ ID NO: 11
Nannospalax galili ST3Gal1

```
MVNLRKKIVK WLTFLLLFVF LTSCFLNYSN SGVPITWFPK QMVLELSENF QKLIKQRPCT   60
CTHCISQSKV SSWFDQRFNQ TMQPLLTASN AMMEEDTYQW WLRLQRERKP NNLSDIVKEL  120
FSLVPGNVDP VLDKRSVGCR RCAVVGNSGN LRASSYGSDI DSHDFVLRMN RAPTVGFEAD  180
VGSRTTHHLV YPESFRELGE NVNMVLVPFK TTDLQWVISA TTTGTITHTY VPVPPKIKVK  240
```

-continued

```
QEKILIYHPA FIKYVFDNWL QGHGRYPSTG ILSVIFSMHV CDEVDLYGFG ADSKGNWHHY  300

WENNPSAGAF RKTGVHDGDF ESNVTTTLAS INKIRIFKGR                        340
```

SEQ ID NO: 12
Monodelphis domestica ST3Gal1

```
MAAIKKKRLK VFTFVLLLVS LTSFFLNYAH TTATYTWFPK QMVMHFSEHF KRFMKYPQRP   60

CSCSQCISET GFAPWFDERF NHTMQPLLNR QNAFLENDTY TWWMKLQRER TPKRLNETFM  120

DLFSIIPGDV DPLLQKGPLI CRRCAVVGNS GNLKESHYGK DIDSHDFVLR MNRAPTAGFE  180

VDVGRKTTHH LVYPESFREL AGNVSMILVP FKTMDLQWLI SALTKGTINF TYVPVPRKIH  240

VNREKILIYH PAFIKYVFDS WLQAHGRYPS TGILSVILSL HICDKVDLYG FGADSKGNWH  300

HYWENNPSAG AFRKTGVHDG DFESNVTSTL ASLNKIRIFK GR                     342
```

SEQ ID NO: 13
Oryctolagus cuniculus ST3Gal1

```
MVTPRKRTLK ALAFLMLFIF LTSFLLNYSH TMVATTWFPK QMVLEFSENL RKLIKTRPCT   60

CAHCVGQRKL SAWFDERFNQ TMQPLLTAHN ALMEEDTYRW WLKLQREKKP NNLNDTIKEL  120

FSVVPGDVDP VLEKRSVGCR RCAVVGNSGN LRESSYGPDI DSHDFVLRMN KAPTVGFEGD  180

VGSKTTHHLV YPESFRELGE NVSMVLVPFK TIDLQWVVSA TTTGTISHTY VPVPAKIKVK  240

QDKILIYHPA FIKYVFDNWL QGHGRYPSTG ILSVIFSMHI CDEVDLYGFG ADSKGNWHHY  300

WENNPSAGAF RKTGVHDADF ESNVTATLAA INKIRIFKGR                        340
```

SEQ ID NO: 14
Cricetulus griseus ST3Gal1

```
MMTTQKKVLK VLTFLVLLIF LTSFVLNFAH TTVPAAWFPK QMVLELSQNL RKLIKPPPCT   60

CTHCISQRKV SAWFDKRFNQ TVQPLLTAHN AVLEEDTYQW WLRLQREKKP SNLSDTIREL  120

FSVVPGNVDP VLEKKSGSCR RCAVVGNSGN LRESSYGPEI DSHDFVLRMN RAPTVGFEAD  180

VGSKTTHHLV YPESFRELGE DVSMILVPFK TIDLQWVVSA TTTGTISHTY VPVPKKIKVK  240

QDKILIYHPA FIKYVFDNWL QGHGRYPSTG ILSVIFSLHV CDEVDLYGFG ADSKGNWHHY  300

WENNPSAGAF RKTGVHDGDF ESNVTATLAA INKIRIFTGR                        340
```

SEQ ID NO: 15
Canis familiaris ST3Gal1

```
MVTMRKRTLK VLTLLVLFIF LTSFFLNYSH TMVTTTWFPK QMVVELSENF KKFMKYTHRP   60

CTCARCIGQQ RVSAWFDERF NRSMQPLLTA QNALLEEDTY SWWLRLQREK QPNNLNDTIR  120

ELFQVVPGNV DPLLEKRSVG CRRCAVVGNS GNLRESWYGP QIDSHDFVLR MNKAPTAGFE  180

MDVGSKTTHH LVYPESFREL AENVSMVLVP FKTTDLEWVV SATTTGTISH TYVPVPAKIK  240

VKKDKILIYH PAFIKYVFDS WLQGHGRYPS TGILSVIFSL HICDEVDLYG FGADSKGNWH  300

HYWENNPSAG AFRKTGVHDG DFESNVTATL ASINKIRIFK GR                     342
```

SEQ ID NO: 16
Fells catus ST3Gal1

```
MVTVRKRTLK VLTLLVLFIF LTSFFLNYSH TMVATTWFPK QMVVELSENF KKFMKYAHRP   60
CTCARCIGQQ RVSPWFDERF NRSMQPLLTA QNALLEEDTY SWWLRLQREK QPNNLNDTIK  120
ELFQVVPGNV DPLLEKKSGG CRRCAVVGNS GNLRESWYGP QIDGHDFVLR MNKAPTAGFE  180
ADVGSKTTHH LVYPESFREL GENVSMVLVP FKTTDLEWVV SATTTGTISH TYVPVPAKIK  240
VKKNKILIYH PAFIKYVFDN WLQGHGRYPS TGILSVIFSL HICDEVDLYG FGADSKGNWH  300
HYWENNPSAG AFRKTGVHDG DFESNVTATL ASINKIRIFK GR                     342
```

SEQ ID NO: 17
Equus caballus ST3Gal1

```
MATHRRRILK VLTLLILFIF LTSFFLNYSH TVVTTAWFPK QMVLELSENF KKLVQYSHRP   60
CSCARCIGQQ KVSSWFDERF NRSMQPLLTV QNAFLEEDAY NWWLRLQREK EPSNLNDTIK  120
ELFRVVPGNV DPLLGKRSVG CRRCAVVGNS GNLKESSYGP QIDSHDFVLR MNKAPTAGFE  180
AYVGSKTTHH LVYPESFREL GENVSMVLVP FKTTDLEWVV SATTTGTISH TYVPVPAKIK  240
VKQDKILIYH PAFIKYVFDN WLQGHGRYPS TGILSVIFSL HICDEVDLYG FGADSRGNWH  300
HYWENNPSAG AFRKTGVHDG DFESNVTATL ASIDKIRIFK GR                     342
```

SEQ ID NO: 18
Gallus ST3Gal1

```
MVTVRKRNVK VFTFAFVLIT VTSFLLNYKH QVTMTTWDPK HIISQFSEQV RKLIKFPRRP   60
CSCSTCISEL GHSLWFDQRF NSTMQPFLTS QNALIPEDSY RWWLKLQGEK SPKNINDTLK  120
ELFGIIPGDR DPLQERGTFS CRRCAVVGNS GNLRQSQYGQ DIDSHDFVLR MNRAPTIGYE  180
SDVGSKTTHH FVYPESYKEL AENVSMIVIP FKTLDLRWIV TALTTGTINF TYVPVPRKIK  240
VRKEKVLIYN PSFIKYVYEN WLQNHGRYPS TGLLSVIFAL HVCDEVNVYG FGADSKGHWH  300
HYWENNASAG AFRQTGVHDG DFEFNVTLTL ASIEKIKFFK GR                     342
```

SEQ ID NO: 19
Columba livia ST3Gal1

```
MVVVRRRNVK VFTFAFLLIT VTSFLLNYTH QVTTTTWDPR HLVMQFSEQV QKLFKYPRRP   60
CSCRSCISEL GHSLWFDQRF NSTMQPFLTS QNALIPEDSY RWWLKLQGEK TPKNINATLK  120
ELFEFIPGDG DPLQERGTST CRRCAVVGNS GNLLQSQYGQ DIDSHDFVLR MNRAPTTGYE  180
SDVGSKTTHH FVYPESYKEL AENVSMILIP FKTLDLRWIV TALTTGTINF TYVPVPRKIK  240
VKKEKILIYN PTFMKYVYEN WLQHHGRYPS TGLLSLIFAL HVCDEVNVYG FGADSRGHWH  300
HYWENNGSAG AFRKTGVHDG DFEFNVTLTL ASIEKINFFK GR                     342
```

SEQ ID NO: 20
Alligator sinensis ST3Gal1

```
MRRRHLKMFS FLFVFIAAMS FFLNYNHYEA MVTWAPQQIV MQFSEQFKKL MKHPRRPCSC   60
KACVSELGLS LWFDERFNQT MQPLLTTQNA LISQDSYRWW LKLQGEKNPK NINETIKELF  120
ETISGDGSQL QERSSSMCRR CAVVGNSGNL RQSHYGQDID SHDFVLRMNR APTVGFESDV  180
GSKTTHHFVY PESFKELPEN VSMIVIPFKT LDLRWIVSAL TTGTINHTYV PVPRKIKVKK  240
```

-continued

EKILVYHPDF LKYVFDHWLQ RHGRYPSTGI LSVVFALHVC DEVNLYGFGA NSKGHWHHYW 300

ENNPSAGAFR QTGVHDGDFE SNITSTLAAV NKIHLFKGR 339

SEQ ID NO: 21
Latimeria chalumnae ST3Gal1

MARHNHRIMW LLTIILLLCV YMVIYDMGED KQKLIKIPSI RRLSGRTIVL DKKLCSCEKC 60

VSEKEESAWF DERFDPNFQP ILMTEVQDIP SHALQWWLSL QAGNKNYNLS ESIAKLFTVV 120

PRTNHSGIRD PAHCRKCAVV GNSGNLKGSN HGKEIDAHHF VIRMNRARTA GFEPDVGIKT 180

THHLMYPESS QDLQPGVHLV LLPFKIMDFE WIRSALTTGE ITRTYFRVQQ FIKADKDKVL 240

IINPTFFKYV CDHWTEHHGR YPSTGMTALV FALHICDEVS VFGYGADSNG NWHHYWENNR 300

NGGAFRRTGV HSGDFESQII KKLADEGKII FYK 333

SEQ ID NO: 22
Ciona intestinalis ST3Gal1

MLINFKLSRV IAMLLVVAIF LTYSWLLLWS TKTALQTNRK NKAGQDEVPV INVIKEDSYV 60

QQKTQNLNKG KRFDLGRVNH SHPREEIQQN NKCGHQLDAS QTRWFRARFN PEIEPVWTQS 120

ALEIDYLVYD WWLSLQSSEA ENLDKTFEAL YKEGVPRKDP FARLTHDREA GCRSCAVVGN 180

SGNILNSNYG NVIDGHDFVI RMNKGPTYNY ENDVGSKTTH RFMYPTTAAS SLPQGVSLVL 240

VPFQPLDIKW LLSALTTGEI TRTYQPLVRR VTCDKSKITI ISPTFIRYVH DRWTQHHGRY 300

PSTGLLALIY ALHECDEVDV YGFGANRAGN WHHYWEDLPP HVAGAFRKTG VHDSAQENEI 360

IDQLHIHGLL RVHRSEQSS 379

The invention claimed is:

1. A cell line that is genetically modified to overexpress a β-galactoside α-2,3-sialyltransferase 1 (ST3Gal1), which is further genetically modified to overexpress a β-galactoside α-2,3-sialyltransferase 4 (ST3Gal4), wherein said cell line can produce a glycoprotein comprising a sialylated GalNAc-O-glycan, said glycoprotein having an increased serum half-life as compared to a nonsialylated glycoprotein.

2. The cell line according to claim 1, which is further genetically modified to overexpress a β-galactoside α-2,6-sialyltransferase 1 (ST6Gal1).

3. The cell line according to claim 1, wherein the cell line comprises endogenous genes encoding ST3Gal1 and ST3Gal4, and optionally an endogenous gene encoding ST6Gal1, and further has at least one genetic element, selected from the group consisting of a promoter, an enhancing element, and a stabilizing element inserted into the genome in one or more position(s) suitable to cause overexpression of ST3Gal1 and ST4Gal4, and optionally ST6Gal1.

4. The cell line according to claim 1, wherein the cell line comprises exogenous nucleic acids encoding ST3Gal1 and ST3Gal4, and optionally an exogenous nucleic acid encoding ST6Gal1.

5. The cell line according to claim 1, wherein the cell line is a mammalian cell line.

6. The cell line according to claim 1, wherein the cell line is derived from a cell line, selected from the group consisting of AGE.CR® cells, Vero cells, MDCK cells, BHK cells, CHO cells, HEK293 cells, HepG2 cells, Huh7 cells, AGE1.HN® cells, NC5T11 cells, Per.C6 cells, HMCLs cells, MM.1 cells, U266 cells, RPMI18226 cells, HKB11 cells, NM cells, NM-F9 cells, and CAP cells.

7. The cell line according to claim 1, wherein the cell line is derived from human primary amniocytes comprising at least one nucleic acid encoding the gene products of the adenoviral E1 and pIX regions.

8. The cell line of claim 5, wherein the mammalian cell line is a human cell line.

* * * * *

SEQUENCE LISTING

<160> NUMBER OF SEQ ID NOS: 22

<210> SEQ ID NO 1
<211> LENGTH: 340
<212> TYPE: PRT
<213> ORGANISM: Homo sapiens

<400> SEQUENCE: 1

```
Met Val Thr Leu Arg Lys Arg Thr Leu Lys Val Leu Thr Phe Leu Val
1               5                   10                  15

Leu Phe Ile Phe Leu Thr Ser Phe Phe Leu Asn Tyr Ser His Thr Met
            20                  25                  30

Val Ala Thr Thr Trp Phe Pro Lys Gln Met Val Leu Glu Leu Ser Glu
        35                  40                  45

Asn Leu Lys Arg Leu Ile Lys His Arg Pro Cys Thr Cys Thr His Cys
    50                  55                  60

Ile Gly Gln Arg Lys Leu Ser Ala Trp Phe Asp Glu Arg Phe Asn Gln
65                  70                  75                  80

Thr Met Gln Pro Leu Leu Thr Ala Gln Asn Ala Leu Leu Glu Asp Asp
                85                  90                  95

Thr Tyr Arg Trp Trp Leu Arg Leu Gln Arg Glu Lys Lys Pro Asn Asn
            100                 105                 110

Leu Asn Asp Thr Ile Lys Glu Leu Phe Arg Val Val Pro Gly Asn Val
        115                 120                 125

Asp Pro Met Leu Glu Lys Arg Ser Val Gly Cys Arg Arg Cys Ala Val
    130                 135                 140
```

```
Val Gly Asn Ser Gly Asn Leu Arg Glu Ser Ser Tyr Gly Pro Glu Ile
145                 150                 155                 160

Asp Ser His Asp Phe Val Leu Arg Met Asn Lys Ala Pro Thr Ala Gly
                165                 170                 175

Phe Glu Ala Asp Val Gly Thr Lys Thr Thr His His Leu Val Tyr Pro
            180                 185                 190

Glu Ser Phe Arg Glu Leu Gly Asp Asn Val Ser Met Ile Leu Val Pro
        195                 200                 205

Phe Lys Thr Ile Asp Leu Glu Trp Val Val Ser Ala Ile Thr Thr Gly
    210                 215                 220

Thr Ile Ser His Thr Tyr Ile Pro Val Pro Ala Lys Ile Arg Val Lys
225                 230                 235                 240

Gln Asp Lys Ile Leu Ile Tyr His Pro Ala Phe Ile Lys Tyr Val Phe
                245                 250                 255

Asp Asn Trp Leu Gln Gly His Gly Arg Tyr Pro Ser Thr Gly Ile Leu
            260                 265                 270

Ser Val Ile Phe Ser Met His Val Cys Asp Glu Val Asp Leu Tyr Gly
        275                 280                 285

Phe Gly Ala Asp Ser Lys Gly Asn Trp His His Tyr Trp Glu Asn Asn
    290                 295                 300

Pro Ser Ala Gly Ala Phe Arg Lys Thr Gly Val His Asp Ala Asp Phe
305                 310                 315                 320

Glu Ser Asn Val Thr Ala Thr Leu Ala Ser Ile Asn Lys Ile Arg Ile
                325                 330                 335

Phe Lys Gly Arg
            340


<210> SEQ ID NO 2
<211> LENGTH: 333
<212> TYPE: PRT
<213> ORGANISM: Homo sapiens

<400> SEQUENCE: 2

Met Val Ser Lys Ser Arg Trp Lys Leu Leu Ala Met Leu Ala Leu Val
1               5                   10                  15

Leu Val Val Met Val Trp Tyr Ser Ile Ser Arg Glu Asp Arg Tyr Ile
            20                  25                  30

Glu Leu Phe Tyr Phe Pro Ile Pro Glu Lys Lys Glu Pro Cys Leu Gln
        35                  40                  45

Gly Glu Ala Glu Ser Lys Ala Ser Lys Leu Phe Gly Asn Tyr Ser Arg
    50                  55                  60

Asp Gln Pro Ile Phe Leu Arg Leu Glu Asp Tyr Phe Trp Val Lys Thr
65                  70                  75                  80

Pro Ser Ala Tyr Glu Leu Pro Tyr Gly Thr Lys Gly Ser Glu Asp Leu
                85                  90                  95

Leu Leu Arg Val Leu Ala Ile Thr Ser Ser Ser Ile Pro Lys Asn Ile
            100                 105                 110

Gln Ser Leu Arg Cys Arg Arg Cys Val Val Val Gly Asn Gly His Arg
        115                 120                 125

Leu Arg Asn Ser Ser Leu Gly Asp Ala Ile Asn Lys Tyr Asp Val Val
    130                 135                 140

Ile Arg Leu Asn Asn Ala Pro Val Ala Gly Tyr Glu Gly Asp Val Gly
145                 150                 155                 160

Ser Lys Thr Thr Met Arg Leu Phe Tyr Pro Glu Ser Ala His Phe Asp
```

```
                165                 170                 175

Pro Lys Val Glu Asn Asn Pro Asp Thr Leu Leu Val Leu Val Ala Phe
            180                 185                 190

Lys Ala Met Asp Phe His Trp Ile Glu Thr Ile Leu Ser Asp Lys Lys
        195                 200                 205

Arg Val Arg Lys Gly Phe Trp Lys Gln Pro Pro Leu Ile Trp Asp Val
    210                 215                 220

Asn Pro Lys Gln Ile Arg Ile Leu Asn Pro Phe Phe Met Glu Ile Ala
225                 230                 235                 240

Ala Asp Lys Leu Leu Ser Leu Pro Met Gln Gln Pro Arg Lys Ile Lys
                245                 250                 255

Gln Lys Pro Thr Thr Gly Leu Leu Ala Ile Thr Leu Ala Leu His Leu
            260                 265                 270

Cys Asp Leu Val His Ile Ala Gly Phe Gly Tyr Pro Asp Ala Tyr Asn
        275                 280                 285

Lys Lys Gln Thr Ile His Tyr Tyr Glu Gln Ile Thr Leu Lys Ser Met
    290                 295                 300

Ala Gly Ser Gly His Asn Val Ser Gln Glu Ala Leu Ala Ile Lys Arg
305                 310                 315                 320

Met Leu Glu Met Gly Ala Ile Lys Asn Leu Thr Ser Phe
                325                 330


<210> SEQ ID NO 3
<211> LENGTH: 500
<212> TYPE: PRT
<213> ORGANISM: Homo sapiens

<400> SEQUENCE: 3

Met Ala Ser Arg Leu Thr Leu Leu Thr Leu Leu Leu Leu Leu Leu Ala
1               5                   10                  15

Gly Asp Arg Ala Ser Ser Asn Pro Asn Ala Thr Ser Ser Ser Ser Gln
            20                  25                  30

Asp Pro Glu Ser Leu Gln Asp Arg Gly Glu Gly Lys Val Ala Thr Thr
        35                  40                  45

Val Ile Ser Lys Met Leu Phe Val Glu Pro Ile Leu Glu Val Ser Ser
    50                  55                  60

Leu Pro Thr Thr Asn Ser Thr Thr Asn Ser Ala Thr Lys Ile Thr Ala
65                  70                  75                  80

Asn Thr Thr Asp Glu Pro Thr Thr Gln Pro Thr Thr Glu Pro Thr Thr
                85                  90                  95

Gln Pro Thr Ile Gln Pro Thr Gln Pro Thr Thr Gln Leu Pro Thr Asp
            100                 105                 110

Ser Pro Thr Gln Pro Thr Thr Gly Ser Phe Cys Pro Gly Pro Val Thr
        115                 120                 125

Leu Cys Ser Asp Leu Glu Ser His Ser Thr Glu Ala Val Leu Gly Asp
    130                 135                 140

Ala Leu Val Asp Phe Ser Leu Lys Leu Tyr His Ala Phe Ser Ala Met
145                 150                 155                 160

Lys Lys Val Glu Thr Asn Met Ala Phe Ser Pro Phe Ser Ile Ala Ser
                165                 170                 175

Leu Leu Thr Gln Val Leu Leu Gly Ala Gly Glu Asn Thr Lys Thr Asn
            180                 185                 190

Leu Glu Ser Ile Leu Ser Tyr Pro Lys Asp Phe Thr Cys Val His Gln
        195                 200                 205
```

```
Ala Leu Lys Gly Phe Thr Thr Lys Gly Val Thr Ser Val Ser Gln Ile
    210                 215                 220

Phe His Ser Pro Asp Leu Ala Ile Arg Asp Thr Phe Val Asn Ala Ser
225                 230                 235                 240

Arg Thr Leu Tyr Ser Ser Ser Pro Arg Val Leu Ser Asn Asn Ser Asp
                245                 250                 255

Ala Asn Leu Glu Leu Ile Asn Thr Trp Val Ala Lys Asn Thr Asn Asn
            260                 265                 270

Lys Ile Ser Arg Leu Leu Asp Ser Leu Pro Ser Asp Thr Arg Leu Val
        275                 280                 285

Leu Leu Asn Ala Ile Tyr Leu Ser Ala Lys Trp Lys Thr Thr Phe Asp
    290                 295                 300

Pro Lys Lys Thr Arg Met Glu Pro Phe His Phe Lys Asn Ser Val Ile
305                 310                 315                 320

Lys Val Pro Met Met Asn Ser Lys Lys Tyr Pro Val Ala His Phe Ile
                325                 330                 335

Asp Gln Thr Leu Lys Ala Lys Val Gly Gln Leu Gln Leu Ser His Asn
            340                 345                 350

Leu Ser Leu Val Ile Leu Val Pro Gln Asn Leu Lys His Arg Leu Glu
        355                 360                 365

Asp Met Glu Gln Ala Leu Ser Pro Ser Val Phe Lys Ala Ile Met Glu
    370                 375                 380

Lys Leu Glu Met Ser Lys Phe Gln Pro Thr Leu Leu Thr Leu Pro Arg
385                 390                 395                 400

Ile Lys Val Thr Thr Ser Gln Asp Met Leu Ser Ile Met Glu Lys Leu
                405                 410                 415

Glu Phe Phe Asp Phe Ser Tyr Asp Leu Asn Leu Cys Gly Leu Thr Glu
            420                 425                 430

Asp Pro Asp Leu Gln Val Ser Ala Met Gln His Gln Thr Val Leu Glu
        435                 440                 445

Leu Thr Glu Thr Gly Val Glu Ala Ala Ala Ala Ser Ala Ile Ser Val
    450                 455                 460

Ala Arg Thr Leu Leu Val Phe Glu Val Gln Gln Pro Phe Leu Phe Val
465                 470                 475                 480

Leu Trp Asp Gln Gln His Lys Phe Pro Val Phe Met Gly Arg Val Tyr
                485                 490                 495

Asp Pro Arg Ala
            500


<210> SEQ ID NO 4
<211> LENGTH: 728
<212> TYPE: PRT
<213> ORGANISM: Homo sapiens

<400> SEQUENCE: 4

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80
```

```
Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495
```

```
Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725


<210> SEQ ID NO 5
<211> LENGTH: 4
<212> TYPE: PRT
<213> ORGANISM: Artificial Sequence
<220> FEATURE:
<223> OTHER INFORMATION: ST3Gal1 motif 3 consensus sequence

<400> SEQUENCE: 5

His Tyr Trp Glu
1


<210> SEQ ID NO 6
<211> LENGTH: 340
<212> TYPE: PRT
<213> ORGANISM: Pan troglodytes

<400> SEQUENCE: 6

Met Val Thr Leu Arg Lys Arg Thr Leu Lys Val Leu Thr Phe Leu Val
1               5                   10                  15

Leu Phe Ile Phe Leu Thr Ser Phe Phe Leu Asn Tyr Ser His Thr Met
            20                  25                  30

Val Ala Thr Thr Trp Phe Pro Lys Gln Met Val Leu Glu Leu Ser Glu
        35                  40                  45

Asn Leu Lys Arg Leu Ile Lys His Arg Pro Cys Thr Cys Thr His Cys
    50                  55                  60

Ile Gly Gln Arg Lys Leu Ser Ala Trp Phe Asp Glu Arg Phe Asn Gln
```

65 70 75 80

Thr Val Gln Pro Leu Leu Thr Ala Gln Asn Ala Leu Leu Glu Asp Asp
85 90 95

Thr Tyr Arg Trp Trp Leu Arg Leu Gln Arg Glu Lys Lys Pro Asn Asn
100 105 110

Leu Asn Asp Thr Ile Lys Glu Leu Phe Arg Val Val Pro Gly Asn Val
115 120 125

Asp Pro Met Leu Glu Lys Arg Ser Val Gly Cys Arg Arg Cys Ala Val
130 135 140

Val Gly Asn Ser Gly Asn Leu Arg Glu Ser Ser Tyr Gly Pro Glu Ile
145 150 155 160

Asp Ser His Asp Phe Val Leu Arg Met Asn Lys Ala Pro Thr Ala Gly
165 170 175

Phe Glu Ala Asp Val Gly Thr Lys Thr Thr His His Leu Val Tyr Pro
180 185 190

Glu Ser Phe Arg Glu Leu Gly Asp Asn Val Ser Met Ile Leu Val Pro
195 200 205

Phe Lys Thr Ile Asp Leu Glu Trp Val Val Ser Ala Ile Thr Thr Gly
210 215 220

Thr Ile Ser His Thr Tyr Val Pro Val Pro Ala Lys Ile Arg Val Lys
225 230 235 240

Gln Asp Lys Ile Leu Ile Tyr His Pro Ala Phe Ile Lys Tyr Val Phe
245 250 255

Asp Asn Trp Leu Gln Gly His Gly Arg Tyr Pro Ser Thr Gly Ile Leu
260 265 270

Ser Val Ile Phe Ser Met His Val Cys Asp Glu Val Asp Leu Tyr Gly
275 280 285

Phe Gly Ala Asp Ser Lys Gly Asn Trp His His Tyr Trp Glu Asn Asn
290 295 300

Pro Ser Ala Gly Ala Phe Arg Lys Thr Gly Val His Asp Ala Asp Phe
305 310 315 320

Glu Ser Asn Val Thr Ala Thr Leu Ala Ser Ile Asn Lys Ile Arg Ile
325 330 335

Phe Lys Gly Arg
340

<210> SEQ ID NO 7
<211> LENGTH: 340
<212> TYPE: PRT
<213> ORGANISM: Macaca mulatta

<400> SEQUENCE: 7

Met Val Thr Leu Arg Lys Arg Thr Leu Lys Val Leu Thr Phe Leu Val
1 5 10 15

Leu Phe Ile Phe Leu Thr Ser Phe Phe Leu Asn Tyr Ser His Thr Met
20 25 30

Val Thr Thr Thr Trp Phe Pro Lys Gln Met Val Leu Glu Leu Ser Glu
35 40 45

Asn Leu Lys Arg Leu Ile Lys His Arg Pro Cys Thr Cys Thr His Cys
50 55 60

Ile Gly Gln Arg Lys Leu Ser Val Trp Phe Asp Glu Arg Phe Asn Gln
65 70 75 80

Thr Val Gln Pro Leu Leu Thr Ala Gln Asn Ala Leu Leu Glu Asp Asp
85 90 95

```
Thr Tyr Arg Trp Trp Leu Arg Leu Gln Arg Glu Lys Lys Pro Asn Asn
            100                 105                 110

Leu Asn Asp Thr Ile Lys Glu Leu Phe Arg Val Val Pro Gly Asn Val
        115                 120                 125

Asp Pro Met Leu Glu Lys Arg Ser Val Gly Cys Arg Arg Cys Ala Val
    130                 135                 140

Val Gly Asn Ser Gly Asn Leu Arg Glu Ser Ser Tyr Gly Pro Glu Ile
145                 150                 155                 160

Asp Arg His Asp Phe Val Leu Arg Met Asn Lys Ala Pro Thr Ala Gly
                165                 170                 175

Phe Glu Ala Asp Val Gly Thr Lys Thr Thr His His Leu Val Tyr Pro
            180                 185                 190

Glu Ser Phe Arg Glu Leu Gly Asp Asn Val Ser Met Ile Leu Val Pro
        195                 200                 205

Phe Lys Thr Ile Asp Leu Glu Trp Val Val Ser Ala Thr Thr Thr Gly
    210                 215                 220

Thr Ile Ser His Thr Tyr Val Pro Val Pro Ala Lys Ile Arg Val Lys
225                 230                 235                 240

Gln Asp Lys Ile Leu Ile Tyr His Pro Ala Phe Ile Lys Tyr Val Phe
                245                 250                 255

Asp Asn Trp Leu Gln Gly His Gly Arg Tyr Pro Ser Thr Gly Ile Leu
            260                 265                 270

Ser Val Ile Phe Ser Met His Val Cys Asp Glu Val Asp Leu Tyr Gly
        275                 280                 285

Phe Gly Ala Asp Ser Lys Gly Asn Trp His His Tyr Trp Glu Asn Asn
    290                 295                 300

Pro Ser Ala Gly Ala Phe Arg Lys Thr Gly Val His Asp Ala Asp Phe
305                 310                 315                 320

Glu Ser Asn Val Thr Ala Thr Leu Ala Ser Ile Asn Lys Ile Arg Ile
                325                 330                 335

Phe Lys Gly Arg
            340
```

<210> SEQ ID NO 8
<211> LENGTH: 343
<212> TYPE: PRT
<213> ORGANISM: Sus scrofa

<400> SEQUENCE: 8

```
Met Ala Pro Met Arg Lys Lys Ser Thr Leu Lys Leu Leu Thr Leu Leu
1               5                   10                  15

Val Leu Phe Ile Phe Leu Thr Ser Phe Phe Leu Asn Tyr Ser His Thr
            20                  25                  30

Val Val Thr Thr Ala Trp Phe Pro Lys Gln Met Val Ile Glu Leu Ser
        35                  40                  45

Glu Asn Phe Lys Lys Leu Met Lys Tyr Pro Tyr Arg Pro Cys Thr Cys
    50                  55                  60

Thr Arg Cys Ile Glu Glu Gln Arg Val Ser Ala Trp Phe Asp Glu Arg
65                  70                  75                  80

Phe Asn Arg Ser Met Gln Pro Leu Leu Thr Ala Lys Asn Ala His Leu
                85                  90                  95

Glu Glu Asp Thr Tyr Lys Trp Trp Leu Arg Leu Gln Arg Glu Lys Gln
            100                 105                 110

Pro Asn Asn Leu Asn Asp Thr Ile Arg Glu Leu Phe Gln Val Val Pro
        115                 120                 125
```

```
Gly Asn Val Asp Pro Leu Leu Glu Lys Arg Leu Val Ser Cys Arg Arg
    130                 135                 140

Cys Ala Val Val Gly Asn Ser Gly Asn Leu Lys Glu Ser Tyr Tyr Gly
145                 150                 155                 160

Pro Gln Ile Asp Ser His Asp Phe Val Leu Arg Met Asn Lys Ala Pro
                165                 170                 175

Thr Glu Gly Phe Glu Ala Asp Val Gly Ser Lys Thr Thr His His Phe
            180                 185                 190

Val Tyr Pro Glu Ser Phe Arg Glu Leu Ala Gln Glu Val Ser Met Ile
        195                 200                 205

Leu Val Pro Phe Lys Thr Thr Asp Leu Glu Trp Val Ile Ser Ala Thr
    210                 215                 220

Thr Thr Gly Arg Ile Ser His Thr Tyr Val Pro Val Pro Ala Lys Ile
225                 230                 235                 240

Lys Val Lys Lys Glu Lys Ile Leu Ile Tyr His Pro Ala Phe Ile Lys
                245                 250                 255

Tyr Val Phe Asp Arg Trp Leu Gln Gly His Gly Arg Tyr Pro Ser Thr
            260                 265                 270

Gly Ile Leu Ser Val Ile Phe Ser Leu His Ile Cys Asp Glu Val Asp
        275                 280                 285

Leu Tyr Gly Phe Gly Ala Asp Ser Lys Gly Asn Trp His His Tyr Trp
    290                 295                 300

Glu Asn Asn Pro Ser Ala Gly Ala Phe Arg Lys Thr Gly Val His Asp
305                 310                 315                 320

Gly Asp Phe Glu Ser Asn Val Thr Thr Ile Leu Ala Ser Ile Asn Lys
                325                 330                 335

Ile Arg Ile Phe Lys Gly Arg
            340


<210> SEQ ID NO 9
<211> LENGTH: 340
<212> TYPE: PRT
<213> ORGANISM: Rattus norvegicus

<400> SEQUENCE: 9

Met Val Asn Met Arg Lys Arg Thr Leu Lys Tyr Leu Thr Phe Phe Leu
1               5                   10                  15

Leu Phe Ile Phe Leu Thr Ser Phe Val Leu Asn Tyr Ser Asn Ser Gly
            20                  25                  30

Val Pro Ser Ala Trp Phe Pro Lys Gln Met Val Leu Glu Phe Ser Glu
        35                  40                  45

Asn Phe Arg Lys Phe Ile Lys Ser Gln Pro Cys Thr Cys Arg His Cys
    50                  55                  60

Ile Ser Gln Gly Lys Val Ser Tyr Trp Phe Asp Gln Arg Phe Asn Lys
65                  70                  75                  80

Thr Met Gln Pro Leu Leu Thr Ala His Asn Ala Leu Met Glu Glu Asp
                85                  90                  95

Thr Tyr Arg Trp Trp Leu Arg Leu Gln Arg Glu Arg Lys Pro Asn Asn
            100                 105                 110

Leu Ser Asp Thr Val Lys Glu Leu Phe Arg Leu Val Pro Gly Asn Val
        115                 120                 125

Asp Pro Met Leu Asn Lys Arg Leu Val Gly Cys Arg Arg Cys Ala Val
    130                 135                 140

Val Gly Asn Ser Gly Asn Leu Lys Asp Ser Ser Tyr Gly Pro Glu Ile
```

```
145                 150                 155                 160

Asp Ser His Asp Phe Val Leu Arg Met Asn Arg Ala Pro Thr Val Gly
                165                 170                 175

Phe Glu Ala Asp Val Gly Ser Arg Thr Thr His His Leu Val Tyr Pro
            180                 185                 190

Glu Ser Phe Arg Glu Leu Gly Glu Asn Val Asn Met Val Leu Val Pro
        195                 200                 205

Phe Lys Ile Thr Asp Leu Gln Trp Val Ile Ser Ala Thr Thr Thr Gly
    210                 215                 220

Thr Ile Thr His Thr Tyr Val Pro Val Pro Pro Lys Ile Lys Val Lys
225                 230                 235                 240

Gln Glu Lys Ile Leu Ile Tyr His Pro Ala Phe Ile Lys Tyr Val Phe
                245                 250                 255

Asp Asn Trp Leu Gln Gly His Gly Arg Tyr Pro Ser Thr Gly Ile Leu
            260                 265                 270

Ser Val Ile Phe Ser Ile His Ile Cys Asp Glu Val Asp Leu Tyr Gly
        275                 280                 285

Phe Gly Ala Asp Ser Lys Gly Asn Trp His His Tyr Trp Glu Asn Asn
    290                 295                 300

Pro Ser Ala Gly Ala Phe Arg Lys Thr Gly Val His Asp Gly Asp Phe
305                 310                 315                 320

Glu Tyr Asn Val Thr Thr Thr Leu Ala Ala Ile Asn Lys Ile Arg Ile
                325                 330                 335

Phe Lys Gly Arg
            340


<210> SEQ ID NO 10
<211> LENGTH: 337
<212> TYPE: PRT
<213> ORGANISM: Mus musculus

<400> SEQUENCE: 10

Met Arg Arg Lys Thr Leu Lys Tyr Leu Thr Phe Phe Leu Leu Phe Ile
1               5                   10                  15

Phe Leu Thr Ser Phe Val Leu Asn Tyr Ser Asn Thr Gly Val Pro Ser
            20                  25                  30

Ala Trp Phe Pro Lys Gln Met Leu Leu Glu Leu Ser Glu Asn Phe Arg
        35                  40                  45

Arg Phe Ile Lys Ser Gln Pro Cys Thr Cys Arg His Cys Ile Ser Gln
    50                  55                  60

Asp Lys Val Ser Tyr Trp Phe Asp Gln Arg Phe Asn Lys Thr Met Gln
65                  70                  75                  80

Pro Leu Leu Thr Val His Asn Ala Leu Met Glu Glu Asp Thr Tyr Arg
                85                  90                  95

Trp Trp Leu Arg Leu Gln Arg Glu Arg Lys Pro Asn Asn Leu Ser Asp
            100                 105                 110

Thr Val Lys Glu Leu Phe Arg Leu Val Pro Gly Asn Val Asp Pro Met
        115                 120                 125

Leu Asn Lys Arg Leu Val Gly Cys Arg Arg Cys Ala Val Val Gly Asn
    130                 135                 140

Ser Gly Asn Leu Lys Asp Ser Ser Tyr Gly Pro Glu Ile Asp Ser His
145                 150                 155                 160

Asp Phe Val Leu Arg Met Asn Lys Ala Pro Thr Val Gly Phe Glu Ala
                165                 170                 175
```

```
Asp Val Gly Ser Arg Thr Thr His His Leu Val Tyr Pro Glu Ser Phe
            180                 185                 190

Arg Glu Leu Gly Glu Asn Val Asn Met Val Leu Val Pro Phe Lys Thr
        195                 200                 205

Thr Asp Leu Gln Trp Val Ile Ser Ala Thr Thr Thr Gly Thr Ile Thr
    210                 215                 220

His Thr Tyr Val Pro Val Pro Pro Lys Ile Lys Val Lys Gln Glu Lys
225                 230                 235                 240

Ile Leu Ile Tyr His Pro Ala Phe Ile Lys Tyr Val Phe Asp Asn Trp
                245                 250                 255

Leu Gln Gly His Gly Arg Tyr Pro Ser Thr Gly Ile Leu Ser Ile Ile
            260                 265                 270

Phe Ser Ile His Ile Cys Asp Glu Val Asp Leu Tyr Gly Phe Gly Ala
        275                 280                 285

Asp Ser Lys Gly Asn Trp His His Tyr Trp Glu Asn Asn Pro Ser Ala
    290                 295                 300

Gly Ala Phe Arg Lys Thr Gly Val His Asp Gly Asp Phe Glu Tyr Asn
305                 310                 315                 320

Ile Thr Thr Thr Leu Ala Ala Ile Asn Lys Ile Arg Ile Phe Lys Gly
                325                 330                 335

Arg


<210> SEQ ID NO 11
<211> LENGTH: 340
<212> TYPE: PRT
<213> ORGANISM: Nannospalax galili

<400> SEQUENCE: 11

Met Val Asn Leu Arg Lys Lys Ile Val Lys Trp Leu Thr Phe Leu Leu
1               5                   10                  15

Leu Phe Val Phe Leu Thr Ser Cys Phe Leu Asn Tyr Ser Asn Ser Gly
            20                  25                  30

Val Pro Ile Thr Trp Phe Pro Lys Gln Met Val Leu Glu Leu Ser Glu
        35                  40                  45

Asn Phe Gln Lys Leu Ile Lys Gln Arg Pro Cys Thr Cys Thr His Cys
    50                  55                  60

Ile Ser Gln Ser Lys Val Ser Ser Trp Phe Asp Gln Arg Phe Asn Gln
65                  70                  75                  80

Thr Met Gln Pro Leu Leu Thr Ala Ser Asn Ala Met Met Glu Glu Asp
                85                  90                  95

Thr Tyr Gln Trp Trp Leu Arg Leu Gln Arg Glu Arg Lys Pro Asn Asn
            100                 105                 110

Leu Ser Asp Ile Val Lys Glu Leu Phe Ser Leu Val Pro Gly Asn Val
        115                 120                 125

Asp Pro Val Leu Asp Lys Arg Ser Val Gly Cys Arg Arg Cys Ala Val
    130                 135                 140

Val Gly Asn Ser Gly Asn Leu Arg Ala Ser Ser Tyr Gly Ser Asp Ile
145                 150                 155                 160

Asp Ser His Asp Phe Val Leu Arg Met Asn Arg Ala Pro Thr Val Gly
                165                 170                 175

Phe Glu Ala Asp Val Gly Ser Arg Thr Thr His His Leu Val Tyr Pro
            180                 185                 190

Glu Ser Phe Arg Glu Leu Gly Glu Asn Val Asn Met Val Leu Val Pro
        195                 200                 205
```

```
Phe Lys Thr Thr Asp Leu Gln Trp Val Ile Ser Ala Thr Thr Thr Gly
    210                 215                 220

Thr Ile Thr His Thr Tyr Val Pro Val Pro Pro Lys Ile Lys Val Lys
225                 230                 235                 240

Gln Glu Lys Ile Leu Ile Tyr His Pro Ala Phe Ile Lys Tyr Val Phe
                245                 250                 255

Asp Asn Trp Leu Gln Gly His Gly Arg Tyr Pro Ser Thr Gly Ile Leu
            260                 265                 270

Ser Val Ile Phe Ser Met His Val Cys Asp Glu Val Asp Leu Tyr Gly
        275                 280                 285

Phe Gly Ala Asp Ser Lys Gly Asn Trp His His Tyr Trp Glu Asn Asn
    290                 295                 300

Pro Ser Ala Gly Ala Phe Arg Lys Thr Gly Val His Asp Gly Asp Phe
305                 310                 315                 320

Glu Ser Asn Val Thr Thr Thr Leu Ala Ser Ile Asn Lys Ile Arg Ile
                325                 330                 335

Phe Lys Gly Arg
            340


<210> SEQ ID NO 12
<211> LENGTH: 342
<212> TYPE: PRT
<213> ORGANISM: Monodelphis domestica

<400> SEQUENCE: 12

Met Ala Ala Ile Lys Lys Lys Arg Leu Lys Val Phe Thr Phe Val Leu
1               5                   10                  15

Leu Leu Val Ser Leu Thr Ser Phe Phe Leu Asn Tyr Ala His Thr Thr
            20                  25                  30

Ala Thr Tyr Thr Trp Phe Pro Lys Gln Met Val Met His Phe Ser Glu
        35                  40                  45

His Phe Lys Arg Phe Met Lys Tyr Pro Gln Arg Pro Cys Ser Cys Ser
    50                  55                  60

Gln Cys Ile Ser Glu Thr Gly Phe Ala Pro Trp Phe Asp Glu Arg Phe
65                  70                  75                  80

Asn His Thr Met Gln Pro Leu Leu Asn Arg Gln Asn Ala Phe Leu Glu
                85                  90                  95

Asn Asp Thr Tyr Thr Trp Trp Met Lys Leu Gln Arg Glu Arg Thr Pro
            100                 105                 110

Lys Arg Leu Asn Glu Thr Phe Met Asp Leu Phe Ser Ile Ile Pro Gly
        115                 120                 125

Asp Val Asp Pro Leu Leu Gln Lys Gly Pro Leu Ile Cys Arg Arg Cys
    130                 135                 140

Ala Val Val Gly Asn Ser Gly Asn Leu Lys Glu Ser His Tyr Gly Lys
145                 150                 155                 160

Asp Ile Asp Ser His Asp Phe Val Leu Arg Met Asn Arg Ala Pro Thr
                165                 170                 175

Ala Gly Phe Glu Val Asp Val Gly Arg Lys Thr Thr His His Leu Val
            180                 185                 190

Tyr Pro Glu Ser Phe Arg Glu Leu Ala Gly Asn Val Ser Met Ile Leu
        195                 200                 205

Val Pro Phe Lys Thr Met Asp Leu Gln Trp Leu Ile Ser Ala Leu Thr
    210                 215                 220

Lys Gly Thr Ile Asn Phe Thr Tyr Val Pro Val Pro Arg Lys Ile His
225                 230                 235                 240
```

```
Val Asn Arg Glu Lys Ile Leu Ile Tyr His Pro Ala Phe Ile Lys Tyr
                245                 250                 255

Val Phe Asp Ser Trp Leu Gln Ala His Gly Arg Tyr Pro Ser Thr Gly
            260                 265                 270

Ile Leu Ser Val Ile Leu Ser Leu His Ile Cys Asp Lys Val Asp Leu
        275                 280                 285

Tyr Gly Phe Gly Ala Asp Ser Lys Gly Asn Trp His His Tyr Trp Glu
    290                 295                 300

Asn Asn Pro Ser Ala Gly Ala Phe Arg Lys Thr Gly Val His Asp Gly
305                 310                 315                 320

Asp Phe Glu Ser Asn Val Thr Ser Thr Leu Ala Ser Leu Asn Lys Ile
                325                 330                 335

Arg Ile Phe Lys Gly Arg
            340


<210> SEQ ID NO 13
<211> LENGTH: 340
<212> TYPE: PRT
<213> ORGANISM: Oryctolagus cuniculus

<400> SEQUENCE: 13

Met Val Thr Pro Arg Lys Arg Thr Leu Lys Ala Leu Ala Phe Leu Met
1               5                   10                  15

Leu Phe Ile Phe Leu Thr Ser Phe Leu Leu Asn Tyr Ser His Thr Met
            20                  25                  30

Val Ala Thr Thr Trp Phe Pro Lys Gln Met Val Leu Glu Phe Ser Glu
        35                  40                  45

Asn Leu Arg Lys Leu Ile Lys Thr Arg Pro Cys Thr Cys Ala His Cys
    50                  55                  60

Val Gly Gln Arg Lys Leu Ser Ala Trp Phe Asp Glu Arg Phe Asn Gln
65                  70                  75                  80

Thr Met Gln Pro Leu Leu Thr Ala His Asn Ala Leu Met Glu Glu Asp
                85                  90                  95

Thr Tyr Arg Trp Trp Leu Lys Leu Gln Arg Glu Lys Lys Pro Asn Asn
            100                 105                 110

Leu Asn Asp Thr Ile Lys Glu Leu Phe Ser Val Val Pro Gly Asp Val
        115                 120                 125

Asp Pro Val Leu Glu Lys Arg Ser Val Gly Cys Arg Arg Cys Ala Val
    130                 135                 140

Val Gly Asn Ser Gly Asn Leu Arg Glu Ser Ser Tyr Gly Pro Asp Ile
145                 150                 155                 160

Asp Ser His Asp Phe Val Leu Arg Met Asn Lys Ala Pro Thr Val Gly
                165                 170                 175

Phe Glu Gly Asp Val Gly Ser Lys Thr Thr His His Leu Val Tyr Pro
            180                 185                 190

Glu Ser Phe Arg Glu Leu Gly Glu Asn Val Ser Met Val Leu Val Pro
        195                 200                 205

Phe Lys Thr Ile Asp Leu Gln Trp Val Val Ser Ala Thr Thr Thr Gly
    210                 215                 220

Thr Ile Ser His Thr Tyr Val Pro Val Pro Ala Lys Ile Lys Val Lys
225                 230                 235                 240

Gln Asp Lys Ile Leu Ile Tyr His Pro Ala Phe Ile Lys Tyr Val Phe
                245                 250                 255

Asp Asn Trp Leu Gln Gly His Gly Arg Tyr Pro Ser Thr Gly Ile Leu
```

```
            260                 265                 270

Ser Val Ile Phe Ser Met His Ile Cys Asp Glu Val Asp Leu Tyr Gly
        275                 280                 285

Phe Gly Ala Asp Ser Lys Gly Asn Trp His His Tyr Trp Glu Asn Asn
    290                 295                 300

Pro Ser Ala Gly Ala Phe Arg Lys Thr Gly Val His Asp Ala Asp Phe
305                 310                 315                 320

Glu Ser Asn Val Thr Ala Thr Leu Ala Ala Ile Asn Lys Ile Arg Ile
                325                 330                 335

Phe Lys Gly Arg
            340


<210> SEQ ID NO 14
<211> LENGTH: 340
<212> TYPE: PRT
<213> ORGANISM: Cricetulus griseus

<400> SEQUENCE: 14

Met Met Thr Thr Gln Lys Lys Val Leu Lys Val Leu Thr Phe Leu Val
1               5                   10                  15

Leu Leu Ile Phe Leu Thr Ser Phe Val Leu Asn Phe Ala His Thr Thr
            20                  25                  30

Val Pro Ala Ala Trp Phe Pro Lys Gln Met Val Leu Glu Leu Ser Gln
        35                  40                  45

Asn Leu Arg Lys Leu Ile Lys Pro Pro Pro Cys Thr Cys Thr His Cys
    50                  55                  60

Ile Ser Gln Arg Lys Val Ser Ala Trp Phe Asp Lys Arg Phe Asn Gln
65                  70                  75                  80

Thr Val Gln Pro Leu Leu Thr Ala His Asn Ala Val Leu Glu Glu Asp
                85                  90                  95

Thr Tyr Gln Trp Trp Leu Arg Leu Gln Arg Glu Lys Lys Pro Ser Asn
            100                 105                 110

Leu Ser Asp Thr Ile Arg Glu Leu Phe Ser Val Val Pro Gly Asn Val
        115                 120                 125

Asp Pro Val Leu Glu Lys Lys Ser Gly Ser Cys Arg Arg Cys Ala Val
    130                 135                 140

Val Gly Asn Ser Gly Asn Leu Arg Glu Ser Ser Tyr Gly Pro Glu Ile
145                 150                 155                 160

Asp Ser His Asp Phe Val Leu Arg Met Asn Arg Ala Pro Thr Val Gly
                165                 170                 175

Phe Glu Ala Asp Val Gly Ser Lys Thr Thr His His Leu Val Tyr Pro
            180                 185                 190

Glu Ser Phe Arg Glu Leu Gly Glu Asp Val Ser Met Ile Leu Val Pro
        195                 200                 205

Phe Lys Thr Ile Asp Leu Gln Trp Val Val Ser Ala Thr Thr Thr Gly
    210                 215                 220

Thr Ile Ser His Thr Tyr Val Pro Val Pro Lys Lys Ile Lys Val Lys
225                 230                 235                 240

Gln Asp Lys Ile Leu Ile Tyr His Pro Ala Phe Ile Lys Tyr Val Phe
                245                 250                 255

Asp Asn Trp Leu Gln Gly His Gly Arg Tyr Pro Ser Thr Gly Ile Leu
            260                 265                 270

Ser Val Ile Phe Ser Leu His Val Cys Asp Glu Val Asp Leu Tyr Gly
        275                 280                 285
```

-continued

```
Phe Gly Ala Asp Ser Lys Gly Asn Trp His His Tyr Trp Glu Asn Asn
    290                 295                 300

Pro Ser Ala Gly Ala Phe Arg Lys Thr Gly Val His Asp Gly Asp Phe
305                 310                 315                 320

Glu Ser Asn Val Thr Ala Thr Leu Ala Ala Ile Asn Lys Ile Arg Ile
                325                 330                 335

Phe Thr Gly Arg
            340


<210> SEQ ID NO 15
<211> LENGTH: 342
<212> TYPE: PRT
<213> ORGANISM: Canis familiaris

<400> SEQUENCE: 15

Met Val Thr Met Arg Lys Arg Thr Leu Lys Val Leu Thr Leu Leu Val
1               5                   10                  15

Leu Phe Ile Phe Leu Thr Ser Phe Phe Leu Asn Tyr Ser His Thr Met
            20                  25                  30

Val Thr Thr Thr Trp Phe Pro Lys Gln Met Val Val Glu Leu Ser Glu
        35                  40                  45

Asn Phe Lys Lys Phe Met Lys Tyr Thr His Arg Pro Cys Thr Cys Ala
    50                  55                  60

Arg Cys Ile Gly Gln Gln Arg Val Ser Ala Trp Phe Asp Glu Arg Phe
65                  70                  75                  80

Asn Arg Ser Met Gln Pro Leu Leu Thr Ala Gln Asn Ala Leu Leu Glu
                85                  90                  95

Glu Asp Thr Tyr Ser Trp Trp Leu Arg Leu Gln Arg Glu Lys Gln Pro
            100                 105                 110

Asn Asn Leu Asn Asp Thr Ile Arg Glu Leu Phe Gln Val Val Pro Gly
        115                 120                 125

Asn Val Asp Pro Leu Leu Glu Lys Arg Ser Val Gly Cys Arg Arg Cys
    130                 135                 140

Ala Val Val Gly Asn Ser Gly Asn Leu Arg Glu Ser Trp Tyr Gly Pro
145                 150                 155                 160

Gln Ile Asp Ser His Asp Phe Val Leu Arg Met Asn Lys Ala Pro Thr
                165                 170                 175

Ala Gly Phe Glu Met Asp Val Gly Ser Lys Thr Thr His His Leu Val
            180                 185                 190

Tyr Pro Glu Ser Phe Arg Glu Leu Ala Glu Asn Val Ser Met Val Leu
        195                 200                 205

Val Pro Phe Lys Thr Thr Asp Leu Glu Trp Val Val Ser Ala Thr Thr
    210                 215                 220

Thr Gly Thr Ile Ser His Thr Tyr Val Pro Val Pro Ala Lys Ile Lys
225                 230                 235                 240

Val Lys Lys Asp Lys Ile Leu Ile Tyr His Pro Ala Phe Ile Lys Tyr
                245                 250                 255

Val Phe Asp Ser Trp Leu Gln Gly His Gly Arg Tyr Pro Ser Thr Gly
            260                 265                 270

Ile Leu Ser Val Ile Phe Ser Leu His Ile Cys Asp Glu Val Asp Leu
        275                 280                 285

Tyr Gly Phe Gly Ala Asp Ser Lys Gly Asn Trp His His Tyr Trp Glu
    290                 295                 300

Asn Asn Pro Ser Ala Gly Ala Phe Arg Lys Thr Gly Val His Asp Gly
305                 310                 315                 320
```

```
Asp Phe Glu Ser Asn Val Thr Ala Thr Leu Ala Ser Ile Asn Lys Ile
                325                 330                 335

Arg Ile Phe Lys Gly Arg
            340


<210> SEQ ID NO 16
<211> LENGTH: 342
<212> TYPE: PRT
<213> ORGANISM: Felis catus

<400> SEQUENCE: 16

Met Val Thr Val Arg Lys Arg Thr Leu Lys Val Leu Thr Leu Leu Val
1               5                   10                  15

Leu Phe Ile Phe Leu Thr Ser Phe Phe Leu Asn Tyr Ser His Thr Met
            20                  25                  30

Val Ala Thr Thr Trp Phe Pro Lys Gln Met Val Val Glu Leu Ser Glu
        35                  40                  45

Asn Phe Lys Lys Phe Met Lys Tyr Ala His Arg Pro Cys Thr Cys Ala
    50                  55                  60

Arg Cys Ile Gly Gln Gln Arg Val Ser Pro Trp Phe Asp Glu Arg Phe
65                  70                  75                  80

Asn Arg Ser Met Gln Pro Leu Leu Thr Ala Gln Asn Ala Leu Leu Glu
                85                  90                  95

Glu Asp Thr Tyr Ser Trp Trp Leu Arg Leu Gln Arg Glu Lys Gln Pro
            100                 105                 110

Asn Asn Leu Asn Asp Thr Ile Lys Glu Leu Phe Gln Val Val Pro Gly
        115                 120                 125

Asn Val Asp Pro Leu Leu Glu Lys Lys Ser Gly Gly Cys Arg Arg Cys
    130                 135                 140

Ala Val Val Gly Asn Ser Gly Asn Leu Arg Glu Ser Trp Tyr Gly Pro
145                 150                 155                 160

Gln Ile Asp Gly His Asp Phe Val Leu Arg Met Asn Lys Ala Pro Thr
                165                 170                 175

Ala Gly Phe Glu Ala Asp Val Gly Ser Lys Thr Thr His His Leu Val
            180                 185                 190

Tyr Pro Glu Ser Phe Arg Glu Leu Gly Glu Asn Val Ser Met Val Leu
        195                 200                 205

Val Pro Phe Lys Thr Thr Asp Leu Glu Trp Val Val Ser Ala Thr Thr
    210                 215                 220

Thr Gly Thr Ile Ser His Thr Tyr Val Pro Val Pro Ala Lys Ile Lys
225                 230                 235                 240

Val Lys Lys Asn Lys Ile Leu Ile Tyr His Pro Ala Phe Ile Lys Tyr
                245                 250                 255

Val Phe Asp Asn Trp Leu Gln Gly His Gly Arg Tyr Pro Ser Thr Gly
            260                 265                 270

Ile Leu Ser Val Ile Phe Ser Leu His Ile Cys Asp Glu Val Asp Leu
        275                 280                 285

Tyr Gly Phe Gly Ala Asp Ser Lys Gly Asn Trp His His Tyr Trp Glu
    290                 295                 300

Asn Asn Pro Ser Ala Gly Ala Phe Arg Lys Thr Gly Val His Asp Gly
305                 310                 315                 320

Asp Phe Glu Ser Asn Val Thr Ala Thr Leu Ala Ser Ile Asn Lys Ile
                325                 330                 335

Arg Ile Phe Lys Gly Arg
```

340

<210> SEQ ID NO 17
<211> LENGTH: 342
<212> TYPE: PRT
<213> ORGANISM: Equus caballus

<400> SEQUENCE: 17

```
Met Ala Thr His Arg Arg Arg Ile Leu Lys Val Leu Thr Leu Leu Ile
1               5                   10                  15

Leu Phe Ile Phe Leu Thr Ser Phe Phe Leu Asn Tyr Ser His Thr Val
            20                  25                  30

Val Thr Thr Ala Trp Phe Pro Lys Gln Met Val Leu Glu Leu Ser Glu
        35                  40                  45

Asn Phe Lys Lys Leu Val Gln Tyr Ser His Arg Pro Cys Ser Cys Ala
    50                  55                  60

Arg Cys Ile Gly Gln Gln Lys Val Ser Ser Trp Phe Asp Glu Arg Phe
65                  70                  75                  80

Asn Arg Ser Met Gln Pro Leu Leu Thr Val Gln Asn Ala Phe Leu Glu
                85                  90                  95

Glu Asp Ala Tyr Asn Trp Trp Leu Arg Leu Gln Arg Glu Lys Glu Pro
            100                 105                 110

Ser Asn Leu Asn Asp Thr Ile Lys Glu Leu Phe Arg Val Val Pro Gly
        115                 120                 125

Asn Val Asp Pro Leu Leu Gly Lys Arg Ser Val Gly Cys Arg Arg Cys
    130                 135                 140

Ala Val Val Gly Asn Ser Gly Asn Leu Lys Glu Ser Ser Tyr Gly Pro
145                 150                 155                 160

Gln Ile Asp Ser His Asp Phe Val Leu Arg Met Asn Lys Ala Pro Thr
                165                 170                 175

Ala Gly Phe Glu Ala Tyr Val Gly Ser Lys Thr Thr His His Leu Val
            180                 185                 190

Tyr Pro Glu Ser Phe Arg Glu Leu Gly Glu Asn Val Ser Met Val Leu
        195                 200                 205

Val Pro Phe Lys Thr Thr Asp Leu Glu Trp Val Val Ser Ala Thr Thr
    210                 215                 220

Thr Gly Thr Ile Ser His Thr Tyr Val Pro Val Pro Ala Lys Ile Lys
225                 230                 235                 240

Val Lys Gln Asp Lys Ile Leu Ile Tyr His Pro Ala Phe Ile Lys Tyr
                245                 250                 255

Val Phe Asp Asn Trp Leu Gln Gly His Gly Arg Tyr Pro Ser Thr Gly
            260                 265                 270

Ile Leu Ser Val Ile Phe Ser Leu His Ile Cys Asp Glu Val Asp Leu
        275                 280                 285

Tyr Gly Phe Gly Ala Asp Ser Arg Gly Asn Trp His His Tyr Trp Glu
    290                 295                 300

Asn Asn Pro Ser Ala Gly Ala Phe Arg Lys Thr Gly Val His Asp Gly
305                 310                 315                 320

Asp Phe Glu Ser Asn Val Thr Ala Thr Leu Ala Ser Ile Asp Lys Ile
                325                 330                 335

Arg Ile Phe Lys Gly Arg
            340
```

<210> SEQ ID NO 18
<211> LENGTH: 342

```
<212> TYPE: PRT
<213> ORGANISM: Gallus gallus

<400> SEQUENCE: 18

Met Val Thr Val Arg Lys Arg Asn Val Lys Val Phe Thr Phe Ala Phe
1               5                   10                  15

Val Leu Ile Thr Val Thr Ser Phe Leu Leu Asn Tyr Lys His Gln Val
            20                  25                  30

Thr Met Thr Thr Trp Asp Pro Lys His Ile Ile Ser Gln Phe Ser Glu
        35                  40                  45

Gln Val Arg Lys Leu Ile Lys Phe Pro Arg Arg Pro Cys Ser Cys Ser
    50                  55                  60

Thr Cys Ile Ser Glu Leu Gly His Ser Leu Trp Phe Asp Gln Arg Phe
65                  70                  75                  80

Asn Ser Thr Met Gln Pro Phe Leu Thr Ser Gln Asn Ala Leu Ile Pro
                85                  90                  95

Glu Asp Ser Tyr Arg Trp Trp Leu Lys Leu Gln Gly Glu Lys Ser Pro
            100                 105                 110

Lys Asn Ile Asn Asp Thr Leu Lys Glu Leu Phe Gly Ile Ile Pro Gly
        115                 120                 125

Asp Arg Asp Pro Leu Gln Glu Arg Gly Thr Phe Ser Cys Arg Arg Cys
    130                 135                 140

Ala Val Val Gly Asn Ser Gly Asn Leu Arg Gln Ser Gln Tyr Gly Gln
145                 150                 155                 160

Asp Ile Asp Ser His Asp Phe Val Leu Arg Met Asn Arg Ala Pro Thr
                165                 170                 175

Ile Gly Tyr Glu Ser Asp Val Gly Ser Lys Thr Thr His His Phe Val
            180                 185                 190

Tyr Pro Glu Ser Tyr Lys Glu Leu Ala Glu Asn Val Ser Met Ile Val
        195                 200                 205

Ile Pro Phe Lys Thr Leu Asp Leu Arg Trp Ile Val Thr Ala Leu Thr
    210                 215                 220

Thr Gly Thr Ile Asn Phe Thr Tyr Val Pro Val Pro Arg Lys Ile Lys
225                 230                 235                 240

Val Arg Lys Glu Lys Val Leu Ile Tyr Asn Pro Ser Phe Ile Lys Tyr
                245                 250                 255

Val Tyr Glu Asn Trp Leu Gln Asn His Gly Arg Tyr Pro Ser Thr Gly
            260                 265                 270

Leu Leu Ser Val Ile Phe Ala Leu His Val Cys Asp Glu Val Asn Val
        275                 280                 285

Tyr Gly Phe Gly Ala Asp Ser Lys Gly His Trp His His Tyr Trp Glu
    290                 295                 300

Asn Asn Ala Ser Ala Gly Ala Phe Arg Gln Thr Gly Val His Asp Gly
305                 310                 315                 320

Asp Phe Glu Phe Asn Val Thr Leu Thr Leu Ala Ser Ile Glu Lys Ile
                325                 330                 335

Lys Phe Phe Lys Gly Arg
            340


<210> SEQ ID NO 19
<211> LENGTH: 342
<212> TYPE: PRT
<213> ORGANISM: Columba livia

<400> SEQUENCE: 19
```

```
Met Val Val Val Arg Arg Arg Asn Val Lys Val Phe Thr Phe Ala Phe
1               5                   10                  15

Leu Leu Ile Thr Val Thr Ser Phe Leu Leu Asn Tyr Thr His Gln Val
            20                  25                  30

Thr Thr Thr Thr Trp Asp Pro Arg His Leu Val Met Gln Phe Ser Glu
        35                  40                  45

Gln Val Gln Lys Leu Phe Lys Tyr Pro Arg Arg Pro Cys Ser Cys Arg
    50                  55                  60

Ser Cys Ile Ser Glu Leu Gly His Ser Leu Trp Phe Asp Gln Arg Phe
65                  70                  75                  80

Asn Ser Thr Met Gln Pro Phe Leu Thr Ser Gln Asn Ala Leu Ile Pro
                85                  90                  95

Glu Asp Ser Tyr Arg Trp Trp Leu Lys Leu Gln Gly Glu Lys Thr Pro
            100                 105                 110

Lys Asn Ile Asn Ala Thr Leu Lys Glu Leu Phe Glu Phe Ile Pro Gly
        115                 120                 125

Asp Gly Asp Pro Leu Gln Glu Arg Gly Thr Ser Thr Cys Arg Arg Cys
    130                 135                 140

Ala Val Val Gly Asn Ser Gly Asn Leu Leu Gln Ser Gln Tyr Gly Gln
145                 150                 155                 160

Asp Ile Asp Ser His Asp Phe Val Leu Arg Met Asn Arg Ala Pro Thr
                165                 170                 175

Thr Gly Tyr Glu Ser Asp Val Gly Ser Lys Thr Thr His His Phe Val
            180                 185                 190

Tyr Pro Glu Ser Tyr Lys Glu Leu Ala Glu Asn Val Ser Met Ile Leu
        195                 200                 205

Ile Pro Phe Lys Thr Leu Asp Leu Arg Trp Ile Val Thr Ala Leu Thr
    210                 215                 220

Thr Gly Thr Ile Asn Phe Thr Tyr Val Pro Val Pro Arg Lys Ile Lys
225                 230                 235                 240

Val Lys Lys Glu Lys Ile Leu Ile Tyr Asn Pro Thr Phe Met Lys Tyr
                245                 250                 255

Val Tyr Glu Asn Trp Leu Gln His His Gly Arg Tyr Pro Ser Thr Gly
            260                 265                 270

Leu Leu Ser Leu Ile Phe Ala Leu His Val Cys Asp Glu Val Asn Val
        275                 280                 285

Tyr Gly Phe Gly Ala Asp Ser Arg Gly His Trp His His Tyr Trp Glu
    290                 295                 300

Asn Asn Gly Ser Ala Gly Ala Phe Arg Lys Thr Gly Val His Asp Gly
305                 310                 315                 320

Asp Phe Glu Phe Asn Val Thr Leu Thr Leu Ala Ser Ile Glu Lys Ile
                325                 330                 335

Asn Phe Phe Lys Gly Arg
            340


<210> SEQ ID NO 20
<211> LENGTH: 339
<212> TYPE: PRT
<213> ORGANISM: Alligator sinensis

<400> SEQUENCE: 20

Met Arg Arg Arg His Leu Lys Met Phe Ser Phe Leu Phe Val Phe Ile
1               5                   10                  15

Ala Ala Met Ser Phe Phe Leu Asn Tyr Asn His Tyr Glu Ala Met Val
            20                  25                  30
```

```
Thr Trp Ala Pro Gln Gln Ile Val Met Gln Phe Ser Glu Gln Phe Lys
        35                  40                  45

Lys Leu Met Lys His Pro Arg Arg Pro Cys Ser Cys Lys Ala Cys Val
    50                  55                  60

Ser Glu Leu Gly Leu Ser Leu Trp Phe Asp Glu Arg Phe Asn Gln Thr
65                  70                  75                  80

Met Gln Pro Leu Leu Thr Thr Gln Asn Ala Leu Ile Ser Gln Asp Ser
                85                  90                  95

Tyr Arg Trp Trp Leu Lys Leu Gln Gly Glu Lys Asn Pro Lys Asn Ile
            100                 105                 110

Asn Glu Thr Ile Lys Glu Leu Phe Glu Thr Ile Ser Gly Asp Gly Ser
        115                 120                 125

Gln Leu Gln Glu Arg Ser Ser Ser Met Cys Arg Arg Cys Ala Val Val
    130                 135                 140

Gly Asn Ser Gly Asn Leu Arg Gln Ser His Tyr Gly Gln Asp Ile Asp
145                 150                 155                 160

Ser His Asp Phe Val Leu Arg Met Asn Arg Ala Pro Thr Val Gly Phe
                165                 170                 175

Glu Ser Asp Val Gly Ser Lys Thr Thr His His Phe Val Tyr Pro Glu
            180                 185                 190

Ser Phe Lys Glu Leu Pro Glu Asn Val Ser Met Ile Val Ile Pro Phe
        195                 200                 205

Lys Thr Leu Asp Leu Arg Trp Ile Val Ser Ala Leu Thr Thr Gly Thr
    210                 215                 220

Ile Asn His Thr Tyr Val Pro Val Pro Arg Lys Ile Lys Val Lys Lys
225                 230                 235                 240

Glu Lys Ile Leu Val Tyr His Pro Asp Phe Leu Lys Tyr Val Phe Asp
                245                 250                 255

His Trp Leu Gln Arg His Gly Arg Tyr Pro Ser Thr Gly Ile Leu Ser
            260                 265                 270

Val Val Phe Ala Leu His Val Cys Asp Glu Val Asn Leu Tyr Gly Phe
        275                 280                 285

Gly Ala Asn Ser Lys Gly His Trp His His Tyr Trp Glu Asn Asn Pro
    290                 295                 300

Ser Ala Gly Ala Phe Arg Gln Thr Gly Val His Asp Gly Asp Phe Glu
305                 310                 315                 320

Ser Asn Ile Thr Ser Thr Leu Ala Ala Val Asn Lys Ile His Leu Phe
                325                 330                 335

Lys Gly Arg
```

<210> SEQ ID NO 21
<211> LENGTH: 333
<212> TYPE: PRT
<213> ORGANISM: Latimeria chalumnae

<400> SEQUENCE: 21

```
Met Ala Arg His Asn His Arg Ile Met Trp Leu Leu Thr Ile Ile Leu
1               5                   10                  15

Leu Leu Cys Val Tyr Met Val Ile Tyr Asp Met Gly Glu Asp Lys Gln
            20                  25                  30

Lys Leu Ile Lys Ile Pro Ser Ile Arg Arg Leu Ser Gly Arg Thr Ile
        35                  40                  45

Val Leu Asp Lys Lys Leu Cys Ser Cys Glu Lys Cys Val Ser Glu Lys
    50                  55                  60
```

```
Glu Glu Ser Ala Trp Phe Asp Glu Arg Phe Asp Pro Asn Phe Gln Pro
65                  70                  75                  80

Ile Leu Met Thr Glu Val Gln Asp Ile Pro Ser His Ala Leu Gln Trp
                85                  90                  95

Trp Leu Ser Leu Gln Ala Gly Asn Lys Asn Tyr Asn Leu Ser Glu Ser
            100                 105                 110

Ile Ala Lys Leu Phe Thr Val Val Pro Arg Thr Asn His Ser Gly Ile
        115                 120                 125

Arg Asp Pro Ala His Cys Arg Lys Cys Ala Val Val Gly Asn Ser Gly
    130                 135                 140

Asn Leu Lys Gly Ser Asn His Gly Lys Glu Ile Asp Ala His His Phe
145                 150                 155                 160

Val Ile Arg Met Asn Arg Ala Arg Thr Ala Gly Phe Glu Pro Asp Val
                165                 170                 175

Gly Ile Lys Thr Thr His His Leu Met Tyr Pro Glu Ser Ser Gln Asp
            180                 185                 190

Leu Gln Pro Gly Val His Leu Val Leu Leu Pro Phe Lys Ile Met Asp
        195                 200                 205

Phe Glu Trp Ile Arg Ser Ala Leu Thr Thr Gly Glu Ile Thr Arg Thr
    210                 215                 220

Tyr Phe Arg Val Gln Gln Phe Ile Lys Ala Asp Lys Asp Lys Val Leu
225                 230                 235                 240

Ile Ile Asn Pro Thr Phe Phe Lys Tyr Val Cys Asp His Trp Thr Glu
                245                 250                 255

His His Gly Arg Tyr Pro Ser Thr Gly Met Thr Ala Leu Val Phe Ala
            260                 265                 270

Leu His Ile Cys Asp Glu Val Ser Val Phe Gly Tyr Gly Ala Asp Ser
        275                 280                 285

Asn Gly Asn Trp His His Tyr Trp Glu Asn Asn Arg Asn Gly Gly Ala
    290                 295                 300

Phe Arg Arg Thr Gly Val His Ser Gly Asp Phe Glu Ser Gln Ile Ile
305                 310                 315                 320

Lys Lys Leu Ala Asp Glu Gly Lys Ile Ile Phe Tyr Lys
                325                 330


<210> SEQ ID NO 22
<211> LENGTH: 379
<212> TYPE: PRT
<213> ORGANISM: Ciona intestinalis

<400> SEQUENCE: 22

Met Leu Ile Asn Phe Lys Leu Ser Arg Val Ile Ala Met Leu Leu Val
1               5                   10                  15

Val Ala Ile Phe Leu Thr Tyr Ser Trp Leu Leu Leu Trp Ser Thr Lys
            20                  25                  30

Thr Ala Leu Gln Thr Asn Arg Lys Asn Lys Ala Gly Gln Asp Glu Val
        35                  40                  45

Pro Val Ile Asn Val Ile Lys Glu Asp Ser Tyr Val Gln Gln Lys Thr
    50                  55                  60

Gln Asn Leu Asn Lys Gly Lys Arg Phe Asp Leu Gly Arg Val Asn His
65                  70                  75                  80

Ser His Pro Arg Glu Glu Ile Gln Gln Asn Asn Lys Cys Gly His Gln
                85                  90                  95

Leu Asp Ala Ser Gln Thr Arg Trp Phe Arg Ala Arg Phe Asn Pro Glu
```

-continued

```
            100                 105                 110

Ile Glu Pro Val Trp Thr Gln Ser Ala Leu Glu Ile Asp Tyr Leu Val
        115                 120                 125

Tyr Asp Trp Trp Leu Ser Leu Gln Ser Ser Glu Ala Glu Asn Leu Asp
    130                 135                 140

Lys Thr Phe Glu Ala Leu Tyr Lys Glu Gly Val Pro Arg Lys Asp Pro
145                 150                 155                 160

Phe Ala Arg Leu Thr His Asp Arg Glu Ala Gly Cys Arg Ser Cys Ala
                165                 170                 175

Val Val Gly Asn Ser Gly Asn Ile Leu Asn Ser Asn Tyr Gly Asn Val
            180                 185                 190

Ile Asp Gly His Asp Phe Val Ile Arg Met Asn Lys Gly Pro Thr Tyr
        195                 200                 205

Asn Tyr Glu Asn Asp Val Gly Ser Lys Thr Thr His Arg Phe Met Tyr
    210                 215                 220

Pro Thr Thr Ala Ala Ser Ser Leu Pro Gln Gly Val Ser Leu Val Leu
225                 230                 235                 240

Val Pro Phe Gln Pro Leu Asp Ile Lys Trp Leu Leu Ser Ala Leu Thr
                245                 250                 255

Thr Gly Glu Ile Thr Arg Thr Tyr Gln Pro Leu Val Arg Arg Val Thr
            260                 265                 270

Cys Asp Lys Ser Lys Ile Thr Ile Ile Ser Pro Thr Phe Ile Arg Tyr
        275                 280                 285

Val His Asp Arg Trp Thr Gln His His Gly Arg Tyr Pro Ser Thr Gly
    290                 295                 300

Leu Leu Ala Leu Ile Tyr Ala Leu His Glu Cys Asp Glu Val Asp Val
305                 310                 315                 320

Tyr Gly Phe Gly Ala Asn Arg Ala Gly Asn Trp His His Tyr Trp Glu
                325                 330                 335

Asp Leu Pro Pro His Val Ala Gly Ala Phe Arg Lys Thr Gly Val His
            340                 345                 350

Asp Ser Ala Gln Glu Asn Glu Ile Ile Asp Gln Leu His Ile His Gly
        355                 360                 365

Leu Leu Arg Val His Arg Ser Glu Gln Ser Ser
    370                 375
```